United States Patent
Gregory et al.

(10) Patent No.: US 9,452,185 B2
(45) Date of Patent: Sep. 27, 2016

(54) MESENCHYMAL STEM CELLS AND SUPPORTS FOR TISSUE REGENERATION, REPAIR AND RECONSTRUCTION

(75) Inventors: Carl A. Gregory, Temple, TX (US); Ulf C. Krause, Temple, TX (US); Bret H. Clough, Temple, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 2 days.

(21) Appl. No.: 13/288,719

(22) Filed: Nov. 3, 2011

(65) Prior Publication Data

US 2012/0100114 A1 Apr. 26, 2012

Related U.S. Application Data

(63) Continuation-in-part of application No. 12/730,022, filed on Mar. 23, 2010.

(60) Provisional application No. 61/210,764, filed on Mar. 23, 2009.

(51) Int. Cl.

| | |
|---|---|
| *A01N 63/00* | (2006.01) |
| *A01N 65/00* | (2009.01) |
| *A61K 35/28* | (2015.01) |
| *C12N 5/0775* | (2010.01) |
| *A61K 35/12* | (2015.01) |

(52) U.S. Cl.
CPC ............. *A61K 35/28* (2013.01); *C12N 5/0663* (2013.01); *A61K 2035/124* (2013.01); *C12N 2501/385* (2013.01); *C12N 2501/415* (2013.01)

(58) Field of Classification Search
None
See application file for complete search history.

(56) References Cited

U.S. PATENT DOCUMENTS

| | | |
|---|---|---|
| 4,352,883 A | 10/1982 | Lim |
| 4,353,888 A | 10/1982 | Sefton |
| 4,678,470 A | 7/1987 | Nashef et al. |
| 4,968,733 A | 11/1990 | Muller et al. |
| 4,976,859 A | 12/1990 | Wechs |
| 5,041,138 A | 8/1991 | Vacanti et al. |
| 5,082,670 A | 1/1992 | Gage et al. |
| 5,084,350 A | 1/1992 | Chang et al. |
| 5,144,016 A | 9/1992 | Skjak-Braek et al. |
| 5,158,881 A | 10/1992 | Aebischer et al. |
| 5,284,761 A | 2/1994 | Aebischer et al. |
| 5,516,532 A | 5/1996 | Atala et al. |
| 5,536,656 A | 7/1996 | Kemp et al. |
| 5,571,083 A | 11/1996 | Lemelson |
| 5,618,531 A | 4/1997 | Cherksey |
| 5,709,854 A | 1/1998 | Griffith-Cima et al. |
| 5,723,331 A | 3/1998 | Tubo et al. |
| 5,736,372 A | 4/1998 | Vacanti et al. |
| 5,741,685 A | 4/1998 | Vacanti |
| 5,759,830 A | 6/1998 | Vacanti et al. |
| 5,770,193 A | 6/1998 | Vacanti et al. |
| 5,770,417 A | 6/1998 | Vacanti et al. |
| 5,804,178 A | 9/1998 | Vacanti et al. |
| 5,855,610 A | 1/1999 | Vacanti et al. |
| 5,863,531 A | 1/1999 | Naughton et al. |
| 5,902,741 A | 5/1999 | Purchio et al. |
| 5,944,754 A | 8/1999 | Vacanti |
| 6,027,744 A | 2/2000 | Vacanti et al. |
| 6,123,727 A | 9/2000 | Vacanti et al. |
| 6,139,574 A | 10/2000 | Vacanti et al. |
| 6,143,501 A | 11/2000 | Sittinger et al. |
| 6,498,018 B1 | 12/2002 | Carpenter |
| 7,175,839 B1 | 2/2007 | Hiserodt |
| 2002/0054901 A1 | 5/2002 | Gainey et al. |
| 2004/0175366 A1* | 9/2004 | Badylak ........................ 424/93.7 |
| 2004/0176855 A1* | 9/2004 | Badylak ...................... 623/23.72 |
| 2005/0013870 A1* | 1/2005 | Freyman et al. ............. 424/520 |
| 2005/0013872 A1* | 1/2005 | Freyman ....................... 424/549 |
| 2005/0025838 A1* | 2/2005 | Badylak ........................ 424/551 |
| 2005/0043819 A1* | 2/2005 | Schmidt et al. ........... 623/23.72 |
| 2005/0054663 A1 | 3/2005 | Bennett et al. |
| 2005/0084494 A1 | 4/2005 | Prockop et al. |
| 2005/0181016 A1* | 8/2005 | Freyman et al. ............. 424/426 |
| 2005/0203636 A1* | 9/2005 | McFetridge ............... 623/23.72 |
| 2005/0256588 A1* | 11/2005 | Sawa et al. ................ 623/23.72 |

(Continued)

FOREIGN PATENT DOCUMENTS

| | | |
|---|---|---|
| WO | WO-92/19195 A1 | 11/1992 |
| WO | WO-95/05452 A2 | 2/1995 |

OTHER PUBLICATIONS

Datta et al., Biomater., 26:971-977 (2005).*
Castano-Izquierdo et al., J. Biomed. Mater. Res. A, 82(1):129-138 (2007).*
Gregory et al., Drug News Pers., 19(8):445-452 (2006).*
van den Dolder et al., J. Biomed. Mater. Res. 62(3):350-358 (2002).*
Cool et al, Stem Cells Devel., 14:632-645 (2005).*
Sampath et al., PNAS, 78(12):7599-7603 (1981).*
Rodriquez et al., JCB, 79:557-565 (2000).*
Dominia et al., Tsitologila, 30(3): 299-304 (1988), abstract.*
Sigma Technical Bulletin (2005).*
Allen et al., JCB, 43:43-57 (1990).*
Vlodaysky et al., PNAS, 84:2292-2296 (1987).*
Badylak, Cell Devel. Biol., 13:377-383 (2002).*
Chastain et al., J. Biomed. Mater. Res. A, 78(1): 73-85 (2006).*
Datta et al., PNAS, 103(8):2488-2493 (2006).*
Holtorf et al., Biomater., 26:6208-6216 (2005).*
Pham et al., Biomater., 29:2729-2739 (2008).*

(Continued)

*Primary Examiner* — Thomas J Visone
(74) *Attorney, Agent, or Firm* — Gardere Wynne Sewell LLP

(57) ABSTRACT

Materials and methods for preparing mesenchymal stem cells are described such that the mesenchymal stem cells remain for a longer period of time than would normally be found at a site of tissue healing. The mesenchymal stem cells are pretreated to exhibit osteogenic characteristics and, when combined with extracellular matrix components produced from the pretreated cells, improve tissue healing. Co-administration of the pretreated cells and their secreted extracellular matrix components at an injured site or defect allowed the mesenchymal stem cells to co-localize at or near the injured or defect site for a longer period. The combination improves overall repair of the tissue by extending the retention signal of mesenchymal stem cells. A three-dimensional scaffold containing the pretreated cells with or without addition of the secreted extracellular matrix is also described. The conditioned scaffold is suitable for use in vivo and may be preserved cryogenically prior to use.

16 Claims, 49 Drawing Sheets

(56) References Cited

U.S. PATENT DOCUMENTS

| | | |
|---|---|---|
| 2005/0261181 A1 | 11/2005 | Wu et al. |
| 2006/0147433 A1* | 7/2006 | Hiles .......................... 424/93.7 |
| 2009/0054963 A1 | 2/2009 | Osypka |
| 2010/0247494 A1 | 9/2010 | Gregory et al. |

OTHER PUBLICATIONS

Quarles et al., 7(6):683-692 (1992).*
Shin et al., Biomater., 26:3645-3654 (2005).*
Datta et al (Biomater., 36:971-977 (2005).*
Castano-Izquierdo et al (J. Biomedic. Mater. Res. A, 129-138(2007).*
Gregory et al (Drug News Perspect., 19(8):445-452 (2006).*
Farrell et al (Tiss. Eng., 12(3):459-468 (2006).*
Marston et al (Diabetes Care, 26:1701-1705 (2003).*
Temenoff, et al. "In vitro osteogenic differentiation of marrow stromal cells encapsulated in biodegradable hydrogels," Wiley InterScience, pp. 235-244 (2004).
Aho, A., et al., Incorporation and Clinical Results of Large Allografts of the Extremities and Pelvis, 1994, Clinical Orthopaedics and Related Research, 307: 200-213.
Akune et al., PPARgamma insufficiency enhances osteogenesis through osteoblast formation from bone marrow progenitors; The Journal of Clinical Investigation, vol. 113, No. 6, Mar. 2004, pp. 846-855.
Alexopoulos, L., et al., Developmental and Osteoarthritic Changes in Col6a1 Knockout Mice: The Biomechanics of Collagen VI in the Cartilage Pericellular Matrix, 2009, National Institute of Health Public Access, 60: 771-779.
Aro, H., et al., Clinical Use of Bone Allografts, 1993, Annals of Medicine, 25: 403-412.
Asahina, I., et al., Human Osteogenic Protein-1 Induces Chondroblastic, Osteoblastic, and/or Adipocytic Differentiation of Clonal Murine Target Cells, 1996, Experimental Cell Research, 222: 38-47.
Austin, T., et al., Blood A Role for the Wnt Gene Family in Hematopoiesis: Expansion of Multilineage Progenitor Cells, 1997, American Society of Hematology, 89: 3624-3635.
Azizi, S., et al., Engraftment and migration of human bone marrow stromal cells implanted in the brains of albino rats-similarities to astrocyte grafts, 1998, Proceedings of the National Academy of Sciences USA, 95: 3908-3913.
Bain, Gerard et al., Activated beta-catenin induces osteoblast differentiation of C3H10T 1/2 cells and participates in BMP2 mediated signal transduction; Biochemical and Biophysical Research Communications vol. 301, 2003, pp. 84-91.
Bateman, J., et al., A Frameshift Mutation Results in a Truncated Nonfunctional Carboxyl-terminal Prod(1) Propeptide of Type I Collagen in Osteogenesis Imperfects, 1989, The Journal of Biological Chemistry, 264: 10960-10964.
Bateman, J., et al., Abnormal type I collagen metabolism by cultured fibroblasts in lethal perinatal osteogenesis imperfecta, 1984, The Journal of Biological Chemistry, 217: 103-115.
Becker, J., et al., Immunohistochemical Distribution of Collagens Types IV, V, and VI and of Pro-collagens Types I and III in Human Alveolar Bone and Dentine, 1986, The Journal of Histochemistry and Cytochemistry, 34: 1417-1429.
Bennett, C., et al., Regulation of Wnt Signaling during Adipogenesis, 2002, The Journal of Biological Chemistry, 277: 30998-31004.
Boland, Genevieve M. et al., Wnt 3a promotes proliferation and suppresses osteogenic differentiation of adult human mesenchymal stem cells; Journal of Cellular Biochemistry, vol. 93, 2004, pp. 1210-1230.
Boyden, Lynn M. et al., High bone density due to a mutation in LDL-receptor-related protein 5; The New England Journal of Medicine, vol. 346, No. 20, May 16, 2002, pp. 1513-1521.
Carraro, G., et al., Similar Sequence-Free Amplification of Human Glyceraldehyde-3-Phosphate Dehydrogenase for Real Time RT-PCR Applications, 2005, Molecular and Cellular Probes, 19: 181-186 (Jun. 2005).

Chen, T., et al., Bone Morphogenetic Protein-2b Stimulation of Growth and Osteogenic Phenotypes in Rat Osteoblast-like Cells: Comparison with TGF-β, 1991, Journal of Bone and Mineral Research, 6: 1387-1390.
Chou, M., et al., Genomic Organization and Characterization of the Human Type XXI Collagen (COL21A1) Gene, 2002, Genomics, 79: 395-401.
Clement-Lacroix, P., et al., Lrp5-independent activation of Wnt signaling by lithium chloride increases bone formation and bone mass in mice, 2005, Proceedings of the National Academy of Sciences, 102: 17406-17411.
Colter, D., et al., Rapid expansion of recycling stem cells in cultures of plastic-adherent cells from human bone marrow, 2000, Proceedings of the National Academy of Sciences, 97: 3213-3218.
Cuomo, A., et al., Mesenchymal Stem Cell Concentration and Bone Repair: Potential Pitfalls from Bench to Bedside, 2009, The Journal of Bone and Joint Surgery, Incorporated, 91: 1073-1083.
Damiens, Eve et al., Anti-mitotic properties of indirubin-3'-monoxime, a CDK/GSK-3 inhibitor: induction of endoreplication following prophase arrest; Oncogene, 2001 vol. 20, pp. 3786-3797.
De Bari, C., et al., Multipotent Mesenchymal Stem Cells From Adult Human Synovial Membrane, 2001, Arthritis & Rheumatism, American College of Rheumatology Published by Wiley-Liss, Inc., 44: 1928-1942.
De Boer, et al., "Wnt signaling inhibits osteogenic differentiation of human mesenchymal stem cells," Elsevier, Bone, 34: 818-826 (2004).
De Boer, H., The History of Bone Grafts, 1988, Clinical Orthopaedics and Related Research, 226: 292-297.
Deng, W., et al., In Vitro Differentiation of Human Marrow Stromal Cells into Early Progenitors of Neural Cells by Conditions That Increase Intracellular Cyclic AMP, 2001, Biochemical and Biophysical Research Communications, 282: 148-152.
Derubeis, A., et al., Bone Marrow Stromal Cells (BMSCs) in Bone Engineering: Limitations and Recent Advances, 2004, Annals of Biomedical Engineering, 32: 160-165.
Dexter, T., et al., Haemopoietic Stem Cells and the Problem of Self-renewal, 1984, Blood Cells, 10: 315-322.
Dishowitz, M., et al., Notch Signaling Components Are Upregulated during Both Endochondral and Intramembranous Bone Regeneration, 2011, Journal of Orthopaedic Research, 30: 296-303.
Doi, M., et al., Genome-wide Screening by cDNA Microarray of Genes Associated with Matrix Mineralization by Human Mesenchymal Stem Cells in Vitro,2002, Biochemical and Biophysical Research Communications, 290: 381-390.
Dominici, M., et al., Minimal criteria for defining multipotent mesenchymal stromal cells. The International Society for Cellular Therapy position statement, 2006, Cytotherapy, 8: 315-317.
Eaves, C., et al., Characterization of Human Hematopoietic Cells with Short-Lived in Vivo Repopulating Activity, 2001, Annals New York Academy of Sciences, 2002, 938: 63-71.
Edgar. R., et al., Gene Expression Omnibus: NCBI gene expression and hybridization array data repository, 2002, Nucleic Acids Research, 30, 207-210.
Einhorn, T., The Cell and Molecular Biology of Fracture Healing, 1998, Clinical Orthopaedics and Related Research, 355S, S7-S21.
Falster, A., et al., Physical Examination of Caffeine's Effects on the Enamel Surface of First Molar in New-Born Rats, 1992, Archives of Oral Biology, 37: 111-118.
Farmer, S.R., Regulation of PPAR activity during adipogenesis; International Journal of Obesity; 2005, 29:S13-16.
Fitzgerald, J., et al., A new FACIT of the collagen family: COL21A1, 2001, Federation of European Biochemical Societies Lett 505: 275-280.
Friedenstein, A., et al., Bone marrow osteogenic stem cells: in vitro cultivation and transplantation in diffusion chambers, 1987, Cell and Tissue Kinetics, 20: 263-272.
Friedenstein, A., et al., Fibroblast Precursors in Normal and Irradiated Mouse Hematopoietic Organs, 1976, Experimental Hematology 4: 267-274.
Fukuda, K., et al., Stem Cells as a Source of Regenerative Cardiomyocytes, 2006, Circulation Research Journal of the American Heart Association, 98: 1002-1013.

(56) References Cited

OTHER PUBLICATIONS

Gong, Yaoqin et al., LDL receptor-related protein 5 (LRP5) affects bone accrual and eye development; Cell, vol. 107, Nov. 16, 2001; pp. 513-523.

Gregory, C. A., Prockop, D. J., Fundamentals of Culture and Characterization of Mesenchymal Stem/Progenitor Cells (MSCs) from Bone Marrow Stroma; Culture of Human Stem Cells, 2007, pp. 207-232.

Gregory, C., Chapter 2 "Mesenchymal Stem Cells: From Culture to Clinic" of Stem Cell Repair and Regeneration., H. Levicar N., N.A., Gordon, M.Y., Dimarakis, I., Ed., 2008, Imperial College Press, London, vol. 3, pp. 21-43.

Gregory, C., et al., Adult Bone Marrow Stem/Progenitor Cells (MSCs) Are Preconditioned by Microenvironmental "Niches" in Culture: A Two-Stage Hypothesis for Regulation of MSC Fate, 2005, Science's STKE 294/pe37: 1-4.

Gregory, C., et al., An Alizarin red-based assay of mineralization by adherent cells in culture: comparison with cetylpyridinium chloride extraction, 2004, Analytical Biochemistry, 329: 77-84.

Gregory, C., et al., Developmental Distribution of Collagen Type XII in Cartilage: Association with Articular Cartilage and the Growth Plate, 2001, Journal of Bone and Mineral Research, 16: 2005-2016.

Gregory, C., et al., Enhanced Engraftment of Mesenchymal Stem Cells in a Cutaneous Wound Model by Culture in Allogenic Species-Specific Serum and Administration in Fibrin Constructs, 2006, Stem Cells, 24: 2232-2243.

Gregory, C., et al., Wnt Signaling Affects Bone Repair by Messenchymal Stem Cells from the Bone Marrow, 2005, Ann. N.Y. Acad. Sci., 1049: 97-106.

Gregory, C., et al., Non-hematopoietic bone marrow stem cells: Molecular control of expansion and differentiation, 2005, Experimental Cell Research, 306: 330-335.

Gregory, C., et al., The Wnt Signaling Inhibitor Dickkopf-1 Is Required for Reentry into the Cell Cycle of Human Adult Stem Cells from Bone Marrow, 2003, The Journal of Biological Chemistry, 278: 28067-28078.

Gregory, et al. dkk-1-derived Synthetic Peptides and Lithium Choloride for the Control and Recovery of Adult Stem Cells from Bone Marrow; published Jun. 4, 2004; Journal of Biological Chemistry, vol. 280, No. 3, pp. 2309-2323.

Gronthos, S., et al., Integrin Expression and Function on Human Osteoblast-like Cells, 1997, Journal of Bone and Mineral Research, 12: 1189-1197.

Guilak, F., et al., Adipose-derived adult stem cells for cartilage tissue engineering, 2004, Biorheology, 41: 389-399.

Gunn, W., et al., A Crosstalk Between Myeloma Cells and Marrow Stromal Cells Stimulates Production of DKK1 and Interleukin-6: A Potential Role in the Development of Lytic Bone Disease and Tumor Progression in Multiple Myeloma, 2005, Stem Cells 24:986-991.

Hadjiargyrou, M., et al., Transcriptional Profiling of Bone Regeneration Insight Into the Molecular Complexity of Wound Repair, 2002, The Journal of Biological Chemistry, 277: 30177-30182.

Hak, D. J., Removal of Broken Hardware, Journal of the American Academy of Orthopaedic Surgeons, vol. 16, No. 2, Feb. 2008, pp. 113-120.

Hofstetter, C., et al., Marrow stromal cells form guiding strands in the injured spinal cord and promote recovery, 2002, Proceedings of the National Academy of Sciences USA, 99: 2199-2204.

Hong, J., et al., TAZ, a Transcriptional Modulator of Mesenchymal Stem Cell Differentiation, 2005, Science, 309: 1074-1078.

Horwitz, E., et al., Clinical responses to bone marrow transplantation in children with severe osteogenesis imperfecta, 2001, Blood, 97: 1227-1231.

Horwitz, et al., Transplantability and therapeutic effects of bone marrow-derived mesenchymal cells in children with osteogenesis imperfecta, 1999, Nature America Inc., 5: 309-313.

Imamura, Y., et al., The Pro-a3(V) Collagen Chain Complete primary structure, expression domains in adult and developing tissues, and comparison to the structures and expression domains of the other types V and XI procollagen chains, 2000, The Journal of Biological Chemistry, 275, 8749-8759.

Ingham, E., et al., Biological reactions to wear debris in total joint replacement, 2000, Proc Inst Mech Eng H., 214: 21-37.

International Search Report for PCT Application No. PCT/US2010/028332 Mailed May 20, 2010.

Issack et al., Role of Wnt Signaling in Bone Remodeling and Repair; Hospital for Special Surgical Journal (2008) 4: 66-70, published online Dec. 8, 2007.

Iwaki, A., et al., Localization and Quantification of Proliferating Cells During Rat Fracture Repair: Detection of Proliferating Cell Nuclear Antigen by Immunohistochemistry, 1997, The Journal of Biological Chemistry, 12: 96-102.

Jiang, Y., et al., Pluripotency of mesenchymal stem cells derived from adult marrow, 2002, Nature, 418: 41-49.

Jokoby, William B., and Pastan, Ira H., Cell Culture, Methods in Enzymology, vol. LVIII, published by Academic Press, Inc., pp. 62-72.

Jope, R., Lithium and GSK-3: one inhibitor, two inhibitory actions, multiple outcomes, 2003, Trends in Pharmacological Sciences, 24: 441-443.

Kao, S., et al., A Review of Bone Substitutes, 2007, Oral and Maxillofacial Surgery Clinics, 19: 513-521.

Keene, D., et al., Human Bone Contains Type III Collagen, Type VI Collagen, and Fibrillin: Type III Collagen is Present on Specific Fibers That May Mediate Attachment of Tendons, Ligaments, and Periosteum to Calcified Bone Cortex, 1991, The Journal of Histochemistry and Cytochemistry, 39: 59-69.

Kehrel, B., et al., Platelets Deficient in Glycoprotein IIIb Aggregate Normally to Collagens Type I and I11 But Not to Collagen Type V, 1993, Blood, 82: 3364-3370.

Khillan, J., et al., Transgenic Mice That Express a Mini-gene Version of the Human Gene for Type I Procollagen (COLIAI) Develop a Phenotype Resembling a Lethal Form of Osteogenesis Imperfects, 1991, The Journal of Biological Chemistry, 266: 23373-23379.

Kim, S., et al., Neural differentiation potential of peripheral blood- and bone-marrow-derived precursor cells, 2006, Brain Research, 1123: 27-33.

Koc., O., et al., Allogeneic mesenchymal stem cell infusion for treatment of metachromatic leukodystrophy (MLD) and Hurler syndrome (MPSIH), 2002, Bone Marrow Transplantation, 30: 215-222.

Kopen, G., et al., Marrow stromal cells migrate throughout forebrain and cerebellum, and they differentiate into astrocytes after injection into neonatal mouse brains, 1999, Proceedings of the National Academy of Sciences USA, 96: 10711-10716.

Kota, B., et al., An overview on biological mechanisms of PPARs, 2005, Pharmacological Research, 51: 85-94.

Krampera, M., et al., Mesenchymal stem cells: from biology to clinical use, 2007, Blood Transfus, 5: 120-129.

Krause, D., et al., Multi-Organ, Multi-Lineage Engraftment by a Single Bone Marrow-Derived Stem Cell, 2001, Cell, 105: 369-377.

Krause, Ulf et al., Pharmaceutical modulation of canonical Wnt signaling in multipotent stromal cells for improved osteoinductive therapy, Proceedings of the National Academy of Sciences, Mar. 2, 2010, vol. 107, No. 9, pp. 4147-4152.

Krause, U., et al., Assays of Osteogenic Differentiation by Cultured Human Mesenchymal Stem Cells, 2011, Methods in Molecular Biology, 698: 215-230.

Krause, U., et al., Potential of Modulating Wnt Signaling Pathway Toward the Development of Bone Anabolic Agent, 2011, Current Molecular Pharmacology, 5: 1-10.

Kulkarni, N., et al., Orally Bioavailable GSK-3α/β Dual Inhibitor Increases Markers of Cellular Differentiation In Vitro and Bone Mass In Vivo, 2006, Journal of Bone and Mineral Research, 21: 910-920.

Kuznetsov, S., et al., Circulating Skeletal Stem Cells, 2001, The Journal of Cell Biology, 153: 1133-1139.

Larson, B., et al., Human Multipotent Stromal Cells Undergo Sharp Transition from Division to Development in Culture, 2008, Stem Cells, 26: 193-201.

(56) References Cited

OTHER PUBLICATIONS

Lisignoli, G., et al., Gene Array Profile Identifies Collagen Type XV as a Novel Human Osteoblast-Secreted Matrix Protein, 2009, Journal of Cellular Physiology, 220: 401-409.
Liu, Guizhong et al., Canonical Wnts function as potent regulators of osteogenesis by human mesenchymal stem cells; The Journal of Cell Biology, vol. 185, 2009, pp. 67-75.
Liu, Jiajian, et al., Regulating the balance between peroxisome proliferator-activated receptor gamma and beta-catenin signaling during adipogenesis. The Journal of Biological Chemistry, vol. 279, No. 43, Oct. 22, 2004; pp. 45020-45027.
Lucki, N., et al, Multiple Roles for Sphingolipids in Steroid Hormone Biosynthesis, 2008, Lipids in Health and Disease, Subcellular Biochemistry, vol. 49: pp. 387-412.
Mareschi, K., et al., Expansion of Mesenchymal Stem Cells Isolated From Pediatric and Adult Donor Bone Marrow, 2006, Journal of Biological Chemistry, 97: 744-754.
Marsell., R., et al., The biology of fracture healing, 2011, Injury, 42: 551-555.
Marsh, D., Concepts of Fracture Union, Delayed Union, and Nonunion, 1998, Clinical Orthopaedics and Related Research, 355S: S22-S30.
Marvulli, D., et al., Spatial and Expression Temporal Changes of Type VI Collagen During Mouse Development; 1996, Developmental Dynamics 206: 447-454.
Mauney, J., et al., Role of Adult Mesenchymal Stem Cells in Bone Tissue-Engineering Applications: Current Status and Future Prospects, 2005, Tissue Engineering, 11: 787-802.
Meijer, Laurent et al., GSK-3-selective inhibitors derived from Tyrian purple indirubins; Chemistry & Biology, vol. 10, Dec. 2003, pp. 1255-1266.
Moldes, M., et al., Peroxisome-proliferator-activated receptor $\gamma$ suppresses Wnt/$\beta$-catenin signaling during adipogenesis, 2003, Biochem J. 376: 607-613.
Morris, N., et al., Developmentally Regulated Alternative Splicing of the $\alpha$1(XI) Collagen Chain: Spatial and Temporal Segregation of Isoforms in the Cartilage of Fetal Rat Long Bones, 2000, The Journal of Histochemistry and Cytochemistry, 48: 725-741.
Morvan, F., et al., Deletion of a Single Allele of the Dkk1 Gene Leads to an Increase in Bone Formation and Bone Mass, 2006, Journal of Bone and Mineral Research, 21: 934-945.
Nagaya, N., et al., Transplantation of Mesenchymal Stem Cells Improves Cardiac Function in a Rat Model of Dilated Cardiomyopathy, Circulation: Journal of the American Heart Association, 112: 1128-1135.
Nedergaard, J., et al., PPAR$\gamma$ in the control of brown adipocyte differentiation, 2005, Biochimica et Biophysica Acta, 1740: 293-304.
Nemoto, T., et al., Differential induction of collagens by mechanical stress in human periodontal ligament cells, 2010, Archives of Oral Biology, 55: 981-97.
Niyibizi, C., et al., Identification of the cartilage al(X1) chain in type V collagen from bovine bone, 1989, FEBS Letters, 242: 314-318.
Ode, A., et al., Toward biomimetic materials in bone regeneration: Functional behavior of mesenchymal stem cells on a broad spectrum of extracellular matrix components, 2010, The Journal of Biomedical Materials Research, 95A: 1114-1124.
Pattyn, F., et al., RTPrimerDB: the Real-Time PCR primer and probe database, 2003, Nucleic Acids Research, 31: 122-123.
Pereira, R., et al., Cultured adherent cells from marrow can serve as long-lasting precursor cells for bone, cartilage, and lung in irradiated mice, 1995, Proceedings of the National Academy of Sciences USA, 92: 4857-4861.
Phinney, D., Biochemical Heterogeneity of Mesenchymal Stem Cell Populations Clues to their Therapeutic Efficacy, 2007, Cell Cycle, 6: 2884-2289.
Phinney, D., et al., Concise Review: Mesenchymal Stem/Multipotent Stromal Cells: The State of Transdifferentiation and Modes of Tissue Repair-Current Views, 2007, Stem Cells, 25: 2896-2902.
Phinney, D., et al., Donor Variation in the Growth Properties and Osteogenic Potential of Human Marrow Stromal Cells, 1999, Journal of Cellular Biochemistry, 75: 424-436.
Phinney, D., et al., Plastic Adherent Stromal Cells From the Bone Marrow of Commonly Used Strains of Inbred Mice: Variations in Yield, Growth, and Differentiation, 1999, Journal of Cellular Biochemistry, 72: 570-585.
Pinnell, S., Regulation of Collagen Biosynthesis by Ascorbic Acid: A Review, 1985, The Yale Journal of Biology and Medicine, 58: 553-559.
Pittenger, M., et al., Multilineage Potential of Adult Human Mesenchymal Stem Cells, 1999, Science, 284: 143-147.
Prockop, D., Marrow Stromal Cells as Stem Cells for Nonhematopoietic Tissues, 1997, Science 276:711-74.
Rawadi, Georges et al., BMP-2 controls alkaline phosphatase expression and osteoblast mineralization by a Wnt autocrine loop; Journal of Bone and Mineral Research, vol. 18, No. 10, 2003; pp. 1842-1853.
Rihn, J., et al., Graft Options in Posterolateral and Posterior Interbody Lumbar Fusion, 2010, Spine, 35: 1629-1639.
Rosada, C., et al., The Human Umbilical Cord Blood: A Potential Source for Osteoblast Progenitor Cells, 2003, Calcified Tissue International, 72: 135-142.
Rosemont, I. L., Chapter 6 from United States Bone and Joint Decade: The burden of musculoskeletal diseases and musculoskeletal injuries; American Academy of Orthopedic Surgeons, 2008, pp. 123-162.
Rosen, E., et al., PPAR$\gamma$ Is Required for the Differentiation of Adipose Tissue In Vivo and In Vitro, 1999, Molecular Cell, 4: 611-677.
Roulet, M., et al., A comprehensive study of the spatial and temporal expression of the col5a1 gene in mouse embryos: a clue for understanding collagen V function in developing connective tissues, 2007, Cell Tissue Res 327, 323-332.
Rubery, P., Enhancing Allograft Bone Healing Through Gene Therapy, 2010, Spine, 35: 1640-1647.
Sampath, T., et al., Recombinant Human Osteogenic Protein- 1 (hOP- 1) Induces New Bone Formation in Vivo with a Specific Activity Comparablew ith Natural Bovine Osteogenic Protein and Stimulates Osteoblast Proliferation and Differentiation in Vitro, 1992, The Journal of Biological Chemistry 267: 20352-20362.
Schindeler, A., et al., Seminars in Cell & Developmental Biology, 2008, Seminars in Cell & Developmental Biology, 19: 423.
Schmidt, A., et al., TGF-$\beta$1 generates a specific multicomponent extracellular matrix in human coronary SMC, 2006, European Journal of Clinical Investigation, 36: 473-482.
Schwarz, E., et al., Bone implant interface, osteolysis and potential therapies, 2004, J Musculoskel Neuron Interact, 4: 390-392.
Sekiya, I., et al., Adipogenic Differentiation of Human Adult Stem Cells From Bone Marrow Stroma (MSCs), 2004, Journal of Bone and Mineral Research, 19: 256-264.
Sekiya, I., et al., BMP-6 Enhances Chondrogenesis in a Subpopulation of Human Marrow Stromal Cells, 2001, Biochemical and Biophysical Research Communications, 284: 411-418.
Sekiya, I., et al., Expansion of Human Adult Stem Cells from Bone Marrow Stroma: Conditions that Maximize the Yields of Early Progenitors and Evaluate Their Quality, 2002, Stem Cells, 20: 530-541.
Sekiya, I., et al., In vitro cartilage formation by human adult stem cells from bone marrow stroma defines the sequence of cellular and molecular events during chondrogenesis, 2002, Proceedings of the National Academy of Sciences USA, 99: 4397-4402.
Seo, M., et al., Differentiation of human adipose stromal cells into hepatic lineage in vitro and in vivo, 2005, Biochemical and Biophysical Research Communications, 328: 258-264.
Shapiro, F., Bone Development and Its Relation to Fracture Repair. The Role of Mesenchymal Osteoblasts and Surface Osteobla, 2008, European Cells and Materials, 15: 53-76.
Shegarfi, H., et al., Review article: Bone transplantation and immune response, 2009, Journal of Orthopaedic Surgery, 17: 206-211.

(56) References Cited

OTHER PUBLICATIONS

Sikavitsas, et al. Pre-culture period of mesenchymal stem cells in osteogenic media influences their in vivo bone forming potential, Journal of Biomedical Materials Research Part A, Published Jan. 31, 2007, vol. 82, pp. 129-138.

Spees., et al., Internalized Antigens Must Be Removed to Prepare Hypoimmunogenic Mesenchymal Stem Cells for Cell and Gene Therapy, 1989, Molecular Therapy, 9: 747-756.

Sugrue, S., et al., Immunoidentification of Type XII Collagen in Embryonic Tissues, 1989, The Journal of Cell Biology, 109: 939-945.

Takuwa, Y., et al., Bone Morphogenetic Protein-2 Stimulates Alkaline Phosphatase Activity and Collagen Synthesis in Cultured Osteoblastic Cells, MC3T3-E1, 1991, Biochemical and Biophysical Research Communications, 174: 96-101.

Tian, Erning et al., The role of the Wnt-signaling antagonist DKK1 in the development of osteolytic lesions in multiple myeloma; The New England Journal of Medicine, vol. 349, No. 26, Dec. 25, 2003, pp. 2483-2494.

Van Den Berg, D., et al., Role of Members of the *Wnt* Gene Family in Human Hematopoiesis, 1998, Blood, 92: 3189-3202.

Van Der Horst, Geertje et al., Downregulation of Wnt signaling by increased expression of Dickkopf-1 and -2 is a prerequisite for late-stage osteoblast differentiation of KS483 cells; 2005, Journal of Bone and Mineral Research, vol. 20, No. 10, published online Jun. 26, 2005, pp. 1867-1877.

Wakitani, S., et al., Myogenic Cells Derived from Rat Bone Marrow Mesenchymal Stem Cells Exposed to 5-Azacytidine, 1995, Muscle & Nerve, 18: 1417-1426.

Walchli, C., et al., Tissue-specific expression of the fibril-associated collagens XII and XIV, 1994, Journal of Cell Science, 107: 669-681.

Wei, et al., "Canonical Wnt Signaling Induces Skin Fibrosis and Subcutaneous Lipoatrophy," Arthritis & Rheumatism, 63(6), 1707-1717 (2011).

Woodbury, D., et al., Adult Rat and Human Bone Marrow Stromal Cells Differentiate Into Neurons, 2000, Journal of Neuroscience Research, 61: 364-370.

Worgall, T., Regulation of Lipid Metabolism by Sphingolipids, 2008, Subcellular Biochemistry, Lipids in Health and Disease, vol. 49, pp. 371-385.

Wozney, J., et al., Novel Regulators of Bone Formation: Molecular Clones and Activities, 1988, Science, 242: 1528-1534.

Yamaguchi, K., et al., Pro-a3(V) collagen chain is expressed in bone and its basic N-terminal peptide adheres to osteosarcoma cells, 2005, Matrix Biology, 24: 283-294.

Yamazaki, M., et al., Spatial and Temporal Expression of Fibril-Forming Minor Collagen Genes (Types V and XI) during Fracture Healing, 1997, Journal of Orthopaedic Research, 1997, 757-764.

Notice of Allowance in U.S. Appl. No. 12/730,022 mailed Jul. 27, 2016 (29 pgs).

\* cited by examiner

FIG. 5
a. matrix only          GW-hMSCs only          composite
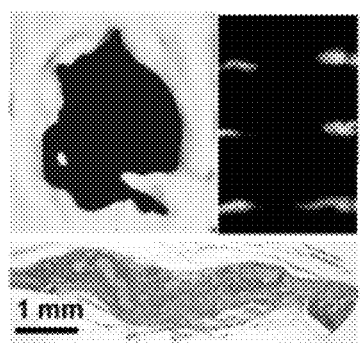 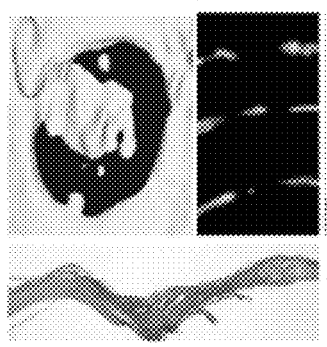 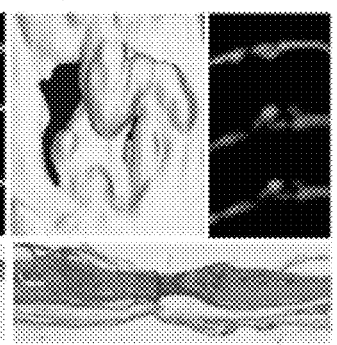
b. 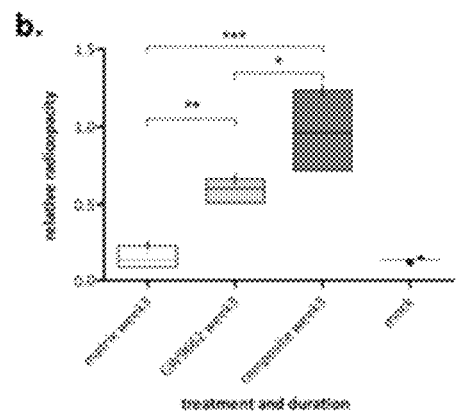    c. 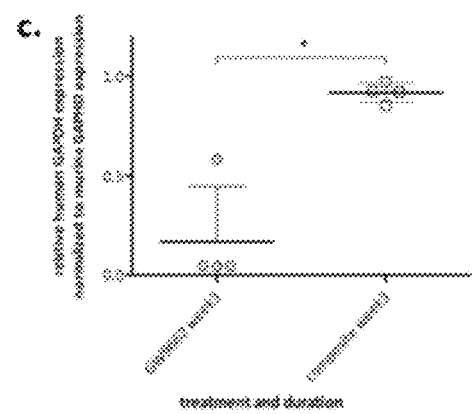
d. cells only          composite
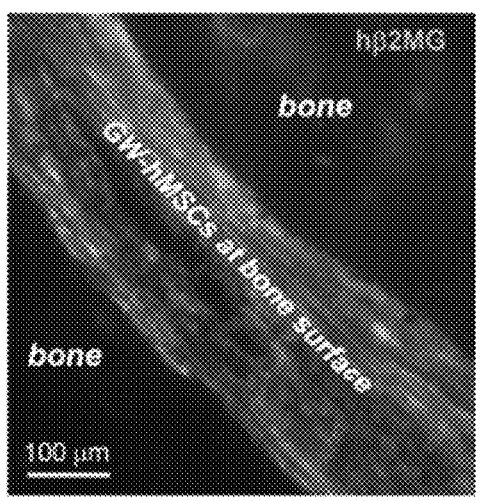 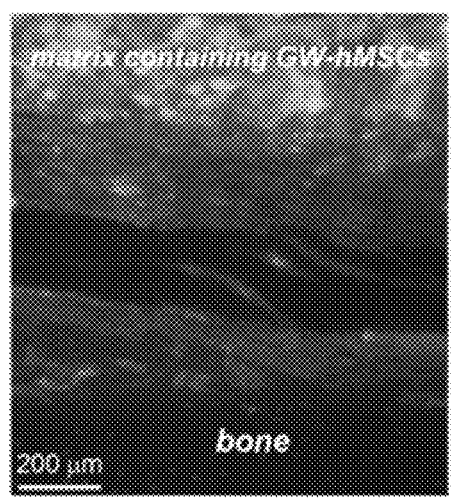

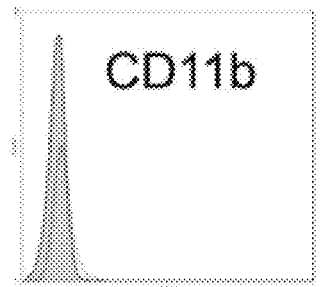
FIG. 7A CD11b
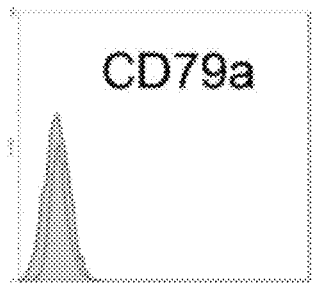
FIG. 7B CD79a
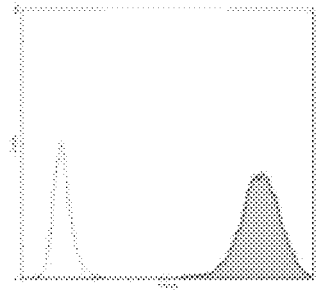
FIG. 7C CD29
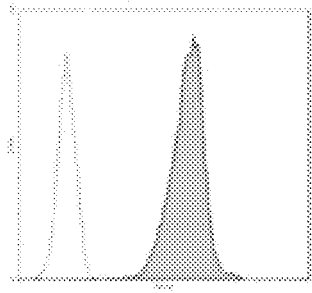
FIG. 7D CD44
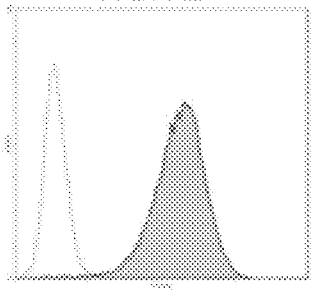
FIG. 7E CD146
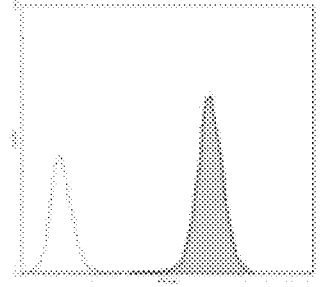
FIG. 7F CD166
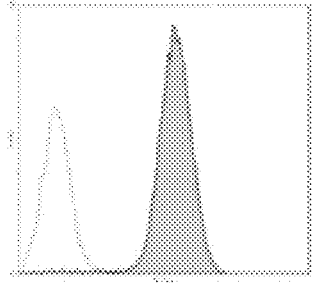
FIG. 7G HLA ABC

FIG. 10A

| Affimetrix Accession | Gene code | Transcript | Entrez Accession | Fold up-regulation |
|---|---|---|---|---|
| *208096_s_at | COL21A1 | collagen, type XXI, alpha 1 | NM_030820 | 4.6353 |
| 218918_at | MAN1C1 | mannosidase, alpha, class 1C, member 1 | NM_020379 | 4.1228 |
| 1554741_s_at | FGF7 KGFLP1 KGFLP2 | fibroblast growth factor 7 (keratinocyte growth factor) /// keratinocyte growth | NM_002009 /// NR_003670 /// NR_003674 | 4.0838 |
| 209395_at | CHI3L1 | chitinase 3-like 1 (cartilage glycoprotein-39) | NM_001276 | 4.0095 |
| 209396_s_at | CHI3L1 | chitinase 3-like 1 (cartilage glycoprotein-39) | NM_001276 | 3.9341 |
| *37892_at | COL11A1 | collagen, type XI, alpha 1 | NM_001854 /// NM_080629 /// NM_080630 | 3.754 |
| 213791_at | PENK | proenkephalin | NM_006211 | 3.7017 |
| 209596_at | MXRA5 | matrix-remodelling associated 5 | NM_015419 | 3.4674 |
| 205782_at | FGF7 | fibroblast growth factor 7 (keratinocyte growth factor) | NM_002009 | 3.4308 |
| *204320_at | COL11A1 | collagen, type XI, alpha 1 | NM_001854 /// NM_080629 /// NM_080630 | 3.3171 |
| 240509_s_at | GREM2 | gremlin 2, cysteine knot superfamily, homolog (Xenopus laevis) | NM_022469 | 3.2038 |
| 243140_at | ACTA2 | Actin, alpha 2, smooth muscle, aorta | NM_001613 | 3.1363 |
| 207761_s_at | METTL7A | methyltransferase like 7A | NM_014033 | 2.9856 |
| *203477_at | COL15A1 | collagen, type XV, alpha 1 | NM_001855 | 2.9769 |
| 208396_s_at | PDE1A | phosphodiesterase 1A, calmodulin-dependent | NM_001003683 NM_005019 | 2.9331 |
| 220540_at | KCNK15 | potassium channel, subfamily K, member 15 | NM_022358 | 2.9049 |
| 209392_at | ENPP2 | ectonucleotide pyrophosphatase/phosphodiesterase 2 | NM_001040092 NM_001130863 NM_006209 | 2.8759 |
| 232914_s_at | SYTL2 | synaptotagmin-like 2 | NM_032379 /// NM_032943 /// NM_206927 /// NM_206928 /// NM_206929 /// NM_206930 | 2.8679 |
| 205475_at | SCRG1 | scrapie responsive protein 1 | NM_007281 | 2.8483 |
| 205792_at | WISP2 | WNT1 inducible signaling pathway protein 2 | NM_003881 | 2.7649 |
| 238178_at | --- | --- | --- | 2.7157 |
| 243431_at | --- | --- | --- | 2.6719 |
| 239907_at | --- | --- | --- | 2.5924 |

FIG. 10B

| Affimetrix Accession | Gene code | Transcript | Entrez Accession | Fold up-regulation |
|---|---|---|---|---|
| 225720_at | SYNPO2 | synaptopodin 2 | NM_001128933 NM_001128934 NM_133477 | 2.571 |
| 238623_at | --- | --- | --- | 2.5685 |
| 206167_s_at | ARHGAP6 | Rho GTPase activating protein 6 | NM_001174 /// NM_006125 /// NM_013422 /// NM_013423 /// NM_013427 | 2.5653 |
| 206101_at | ECM2 | extracellular matrix protein 2, female organ and adipocyte specific | NM_001393 | 2.5561 |
| 206201_s_at | MEOX2 | mesenchyme homeobox 2 | NM_005924 | 2.5237 |
| 223541_at | HAS3 | hyaluronan synthase 3 | NM_005329 /// NM_138612 | 2.4805 |
| 241981_at | FAM20A | family with sequence similarity 20, member A | NM_017565 | 2.4716 |
| *231766_s_at | COL12A1 | collagen, type XII, alpha 1 | NM_004370 /// NM_080645 | 2.4679 |
| 223475_at | CRISPLD1 | cysteine-rich secretory protein LCCL domain containing 1 | NM_031461 | 2.4565 |
| 202532_s_at | DHFR | dihydrofolate reductase | NM_000791 | 2.452 |
| 206932_at | CH25H | cholesterol 25-hydroxylase | NM_003956 | 2.4517 |
| 232538_at | --- | --- | --- | 2.4404 |
| 225895_at | SYNPO2 | synaptopodin 2 | NM_001128933 NM_001128934 NM_133477 | 2.4075 |
| 1569323_at | PTPRG | protein tyrosine phosphatase, receptor type, G | NM_002841 | 2.4064 |
| 1555852_at | --- | --- | --- | 2.3998 |
| 202350_s_at | MATN2 | matrilin 2 | NM_002380 /// NM_030583 | 2.39 |
| *225664_at | COL12A1 | collagen, type XII, alpha 1 | NM_004370 /// NM_080645 | 2.3755 |
| 1552455_at | PRUNE2 | prune homolog 2 (Drosophila) | NM_015225 /// NM_138818 | 2.3733 |
| 203638_s_at | FGFR2 | fibroblast growth factor receptor 2 | NM_000141 /// NM_022970 | 2.3645 |
| 231031_at | KGFLP2 | keratinocyte growth factor-like protein 2 | NR_003670 | 2.3632 |
| 210839_s_at | ENPP2 | ectonucleotide pyrophosphatase/phosphodiesterase 2 | NM_001040092 NM_001130863 NM_006209 | 2.3545 |
| 219087_at | ASPN | asporin | NM_017680 | 2.3531 |
| 227662_at | SYNPO2 | synaptopodin 2 | NM_001128933 NM_001128934 NM_133477 | 2.3517 |

FIG. 10C

| Affimetrix Accession | Gene code | Transcript | Entrez Accession | Fold up-regulation |
|---|---|---|---|---|
| 224559_at | MALAT1 | metastasis associated lung adenocarcinoma transcript 1 (non-protein coding) | NR_002819 | 2.3385 |
| 228750_at | --- | --- | --- | 2.3374 |
| 204072_s_at | FRY | furry homolog (Drosophila) | NM_023037 | 2.3333 |
| 235821_at | --- | --- | --- | 2.3267 |
| 229802_at | --- | --- | --- | 2.3213 |
| 37512_at | HSD17B6 | hydroxysteroid (17-beta) dehydrogenase 6 homolog (mouse) | NM_003725 | 2.3211 |
| 205609_at | ANGPT1 | angiopoietin 1 | NM_001146 | 2.3146 |
| 204984_at | GPC4 | glypican 4 | NM_001448 | 2.313 |
| 209960_at | HGF | hepatocyte growth factor (hepapoietin A; scatter factor) | NM_000601 /// NM_001010931 NM_001010932 NM_001010933 NM_001010934 | 2.3081 |
| 227419_x_at | PLAC9 | placenta-specific 9 | NM_001012973 | 2.3017 |
| 210997_at | HGF | hepatocyte growth factor (hepapoietin A; scatter factor) | NM_000601 /// NM_001010931 NM_001010932 NM_001010933 NM_001010934 | 2.2886 |
| 240282_at | WDR1 | WD repeat domain 1 | NM_005112 /// NM_017491 | 2.2805 |
| 222253_s_at | DKFZP434P211 | POM121-like protein | NR_003714 | 2.2732 |
| 205713_s_at | COMP | cartilage oligomeric matrix protein | NM_000095 | 2.2649 |
| 206070_s_at | EPHA3 | EPH receptor A3 | NM_005233 /// NM_182644 | 2.2648 |
| 222379_at | KCNE4 | potassium voltage-gated channel, Isk-related family, member 4 | NM_080671 | 2.2513 |
| 1565706_at | --- | --- | --- | 2.2456 |
| 1559391_s_at | --- | --- | --- | 2.2435 |
| 241734_at | SRFBP1 | serum response factor binding protein 1 | NM_152546 | 2.2306 |
| *212865_s_at | COL14A1 | collagen, type XIV, alpha 1 | NM_021110 | 2.23 |
| *229271_x_at | COL11A1 | collagen, type XI, alpha 1 | NM_001854 /// NM_080629 /// NM_080630 | 2.2261 |
| 219789_at | NPR3 | natriuretic peptide receptor C/guanylate cyclase C (atrionatriuretic peptide rec | NM_000908 | 2.2233 |
| 240277_at | --- | --- | --- | 2.2192 |
| 232298_at | hCG_1806964 | hCG1806964 | XR_041581 /// XR_041582 /// XR_041583 | 2.2154 |
| 229554_at | --- | --- | --- | 2.2139 |
| 227265_at | FGL2 | fibrinogen-like 2 | NM_006682 | 2.212 |
| 242110_at | --- | --- | --- | 2.2057 |

FIG. 10D

| Affimetrix Accession | Gene code | Transcript | Entrez Accession | Fold up-regulation |
|---|---|---|---|---|
| 216147_at | --- | --- | --- | 2.2053 |
| 225975_at | PCDH18 | protocadherin 18 | NM_019035 | 2.205 |
| 209894_at | LEPR | leptin receptor | NM_001003679 NM_001003680 NM_002303 | 2.2043 |
| 241789_at | --- | --- | --- | 2.1941 |
| 205907_s_at | OMD | osteomodulin | NM_005014 | 2.1878 |
| 228218_at | --- | --- | --- | 2.1728 |
| 239614_x_at | --- | --- | --- | 2.1653 |
| 231067_s_at | --- | --- | --- | 2.162 |
| 220076_at | ANKH | ankylosis, progressive homolog (mouse) | NM_054027 | 2.1592 |
| 243495_s_at | --- | --- | --- | 2.1562 |
| 241780_at | --- | --- | --- | 2.1554 |
| 203854_at | CFI | complement factor I | NM_000204 | 2.1501 |
| 236325_at | KIAA1377 | KIAA1377 | NM_020802 | 2.1457 |
| 226930_at | FNDC1 | fibronectin type III domain containing 1 | NM_032532 | 2.1401 |
| 202437_s_at | CYP1B1 | cytochrome P450, family 1, subfamily B, polypeptide 1 | NM_000104 | 2.1399 |
| 212230_at | PPAP2B | phosphatidic acid phosphatase type 2B | NM_003713 /// NM_177414 | 2.1367 |
| 208015_at | SMAD1 | SMAD family member 1 | NM_001003688 NM_005900 | 2.1321 |
| 202234_s_at | SLC16A1 | solute carrier family 16, member 1 (monocarboxylic acid transporter 1) | NM_003051 | 2.1296 |
| 232768_at | CCNB2 | Cyclin B2 | NM_004701 | 2.1289 |
| 1557487_at | --- | --- | --- | 2.1284 |
| 229479_at | --- | --- | --- | 2.1206 |
| 204120_s_at | ADK | adenosine kinase | NM_001123 /// NM_006721 | 2.1171 |
| 203813_s_at | SLIT3 | slit homolog 3 (Drosophila) | NM_003062 | 2.114 |
| 243864_at | CCDC80 | coiled-coil domain containing 80 | NM_199511 /// NM_199512 | 2.1122 |
| 235611_at | --- | --- | --- | 2.1096 |
| 1552701_a_at | COP1 | caspase-1 dominant-negative inhibitor pseudo-ICE | NM_001017534 NM_052889 | 2.1087 |
| 227300_at | TMEM119 | transmembrane protein 119 | NM_181724 | 2.1076 |
| 235603_at | HNRNPU | heterogeneous nuclear ribonucleoprotein U (scaffold attachment factor A) | NM_004501 /// NM_031844 | 2.1065 |
| 242300_at | --- | --- | --- | 2.0996 |
| 219054_at | C5orf23 | chromosome 5 open reading frame 23 | NM_024563 | 2.0991 |
| 1557437_a_at | --- | --- | --- | 2.0973 |
| 223797_at | PRO2852 | hypothetical protein PRO2852 | --- | 2.095 |

FIG. 10E

| Affimetrix Accession | Gene code | Transcript | Entrez Accession | Fold up-regulation |
|---|---|---|---|---|
| 209335_at | DCN | decorin | NM_001920 /// NM_133503 /// NM_133504 /// NM_133505 /// NM_133506 /// NM_133507 | 2.0913 |
| 243904_at | --- | --- | --- | 2.0901 |
| 230147_at | F2RL2 | coagulation factor II (thrombin) receptor-like 2 | NM_004101 | 2.0895 |
| 236046_at | FLJ44896 | FLJ44896 protein | XR_041619 /// XR_041620 /// XR_041621 | 2.0875 |
| 204051_s_at | SFRP4 | secreted frizzled-related protein 4 | NM_003014 | 2.0821 |
| 202436_s_at | CYP1B1 | cytochrome P450, family 1, subfamily B, polypeptide 1 | NM_000104 | 2.0799 |
| 205498_at | GHR | growth hormone receptor | NM_000163 | 2.0787 |
| 229121_at | --- | --- | --- | 2.0719 |
| 1554547_at | FAM13C1 | family with sequence similarity 13, member C1 | NM_001001971 NM_198215 | 2.0714 |
| 239582_at | PML | promyelocytic leukemia | NM_002675 /// NM_033238 /// NM_033239 /// NM_033240 /// NM_033244 /// NM_033246 | 2.0669 |
| 202435_s_at | CYP1B1 | cytochrome P450, family 1, subfamily B, polypeptide 1 | NM_000104 | 2.0551 |
| 239449_at | --- | --- | --- | 2.0496 |
| 227236_at | TSPAN2 | tetraspanin 2 | NM_005725 | 2.049 |
| 235371_at | GLT8D4 | glycosyltransferase 8 domain containing 4 | NM_001080393 | 2.0488 |
| 218559_s_at | MAFB | v-maf musculoaponeurotic fibrosarcoma oncogene homolog B (avian) | NM_005461 | 2.0484 |
| 227198_at | AFF3 | AF4/FMR2 family, member 3 | NM_001025108 NM_002285 | 2.0442 |
| 201369_s_at | ZFP36L2 | zinc finger protein 36, C3H type-like 2 | NM_006887 | 2.0429 |
| 228754_at | SLC6A6 | solute carrier family 6 (neurotransmitter transporter, taurine), member 6 | NM_001134367 NM_001134368 NM_003043 | 2.0417 |
| 228180_at | --- | --- | --- | 2.0377 |
| 235702_at | --- | --- | --- | 2.0359 |
| 212226_s_at | PPAP2B | phosphatidic acid phosphatase type 2B | NM_003713 /// NM_177414 | 2.0343 |
| 235171_at | --- | --- | --- | 2.0335 |
| 239286_at | CDH11 | cadherin 11, type 2, OB-cadherin (osteoblast) | NM_001797 | 2.0332 |
| 243982_at | KLHL28 | Kelch-like 28 (Drosophila) | NM_017658 | 2.0328 |

FIG. 10F

| Affimetrix Accession | Gene code | Transcript | Entrez Accession | Fold up-regulation |
|---|---|---|---|---|
| 218128_at | NFYB | nuclear transcription factor Y, beta | NM_006166 | 2.0327 |
| 244010_at | --- | --- | --- | 2.0282 |
| 240307_at | --- | --- | --- | 2.0184 |
| 215175_at | PCNX | pecanex homolog (Drosophila) | NM_014982 | 2.0172 |
| 232060_at | ROR1 | receptor tyrosine kinase-like orphan receptor 1 | NM_001083592 NM_005012 | 2.0156 |
| 237483_at | --- | --- | --- | 2.015 |
| 201010_s_at | TXNIP | thioredoxin interacting protein | NM_006472 | 2.0146 |
| 212989_at | SGMS1 | sphingomyelin synthase 1 | NM_147156 | 2.0135 |
| 235337_at | --- | --- | --- | 2.0086 |
| 243352_at | ALPK1 | alpha-kinase 1 | NM_001102406 NM_025144 | 2.008 |
| 242532_at | --- | --- | --- | 2.0077 |
| 204963_at | SSPN | sarcospan (Kras oncogene-associated gene) | NM_005086 | 2.0042 |

FIG. 11A

| Affimetrix Accession | Gene code | Transcript | Entrez Accession | Fold up-regulation |
|---|---|---|---|---|
| *37892_at | COL11A1 | collagen, type XI, alpha 1 | NM_001854 /// NM_080629 /// NM_080630 | 4.1561 |
| *208096_s_at | COL21A1 | collagen, type XXI, alpha 1 | NM_030820 | 4.1456 |
| *204320_at | COL11A1 | collagen, type XI, alpha 1 | NM_001854 /// NM_080629 /// NM_080630 | 3.9556 |
| 209395_at | CHI3L1 | chitinase 3-like 1 (cartilage glycoprotein-39) | NM_001276 | 3.549 |
| 213791_at | PENK | proenkephalin | NM_006211 | 3.251 |
| 209396_s_at | CHI3L1 | chitinase 3-like 1 (cartilage glycoprotein-39) | NM_001276 | 3.2317 |
| 205475_at | SCRG1 | scrapie responsive protein 1 | NM_007281 | 3.1565 |
| *229271_x_at | COL11A1 | collagen, type XI, alpha 1 | NM_001854 /// NM_080629 /// NM_080630 | 3.1322 |
| *203477_at | COL15A1 | collagen, type XV, alpha 1 | NM_001855 | 3.0279 |
| 218918_at | MAN1C1 | mannosidase, alpha, class 1C, member 1 | NM_020379 | 2.7777 |
| 1554741_s_at | FGF7 /// KGFLP1 /// KGFLP2 | fibroblast growth factor 7 (keratinocyte growth factor) keratinocyte growth factor | NM_002009 /// NR_003670 /// NR_003674 | 2.6439 |
| 209596_at | MXRA5 | matrix-remodelling associated 5 | NM_015419 | 2.5198 |
| 205200_at | CLEC3B | C-type lectin domain family 3, member B | NM_003278 | 2.4373 |
| 228325_at | KIAA0146 | KIAA0146 | NM_001080394 | 2.3891 |
| 228707_at | CLDN23 | claudin 23 | NM_194284 | 2.3831 |
| 238178_at | --- | --- | --- | -2.3807 |
| 205782_at | FGF7 | fibroblast growth factor 7 (keratinocyte growth factor) | NM_002009 | 2.3672 |
| 205713_s_at | COMP | cartilage oligomeric matrix protein | NM_000095 | 2.3656 |
| 222614_at | RWDD2B | RWD domain containing 2B | NM_016940 | 2.3538 |
| 209392_at | ENPP2 | ectonucleotide pyrophosphatase/phosphodiesterase 2 | NM_001040092 NM_001130863 NM_006209 | 2.3511 |
| 205792_at | WISP2 | WNT1 inducible signaling pathway protein 2 | NM_003881 | -2.3288 |
| 206932_at | CH25H | cholesterol 25-hydroxylase | NM_003956 | 2.3214 |
| 236224_at | RIT1 | Ras-like without CAAX 1 | NM_006912 | 2.2742 |

FIG. 11B

| Affimetrix Accession | Gene code | Transcript | Entrez Accession | Fold up-regulation |
|---|---|---|---|---|
| 210997_at | HGF | hepatocyte growth factor (hepapoietin A; scatter factor) | NM_000601 /// NM_001010931 NM_001010932 NM_001010933 NM_001010934 | 2.2652 |
| 241981_at | FAM20A | family with sequence similarity 20, member A | NM_017565 | 2.2571 |
| 204051_s_at | SFRP4 | secreted frizzled-related protein 4 | NM_003014 | 2.2505 |
| 227300_at | TMEM119 | transmembrane protein 119 | NM_181724 | 2.2483 |
| 201010_s_at | TXNIP | thioredoxin interacting protein | NM_006472 | 2.2335 |
| 235666_at | --- | --- | --- | 2.1944 |
| 209351_at | KRT14 | keratin 14 (epidermolysis bullosa simplex, Dowling-Meara, Koebner) | NM_000526 | 2.1938 |
| 203812_at | --- | --- | --- | 2.174 |
| 240509_s_at | GREM2 | gremlin 2, cysteine knot superfamily, homolog (Xenopus laevis) | NM_022469 | 2.1702 |
| 228834_at | TOB1 | transducer of ERBB2, 1 | NM_005749 | 2.164 |
| 244187_at | APOOL | Apolipoprotein O-like | NM_198450 | 2.1621 |
| 223044_at | SLC40A1 | solute carrier family 40 (iron-regulated transporter), member 1 | NM_014585 | 2.1351 |
| 231031_at | KGFLP2 | keratinocyte growth factor-like protein 2 | NR_003670 | 2.1279 |
| 202575_at | CRABP2 | cellular retinoic acid binding protein 2 | NM_001878 | 2.1207 |
| 1565666_s_at | LOC100133432 LOC100133761 MUC6 | similar to Mucin-6 precursor (Gastric mucin-6) /// similar to Mucin-6 precursor | NM_005961 /// XM_001714734 XM_001718792 | 2.1197 |
| 227478_at | SETBP1 | SET binding protein 1 | NM_001130110 NM_015559 | 2.0973 |
| 208396_s_at | PDE1A | phosphodiesterase 1A, calmodulin-dependent | NM_001003683 NM_005019 | 2.0825 |
| 228750_at | --- | --- | --- | 2.0801 |
| 243495_s_at | --- | --- | --- | 2.0675 |
| *225664_at | COL12A1 | collagen, type XII, alpha 1 | NM_004370 /// NM_080645 | 2.0668 |
| 213872_at | --- | --- | --- | 2.0653 |
| 232224_at | MASP1 | mannan-binding lectin serine peptidase 1 (C4/C2 activating component of Ra-react | NM_001031849 NM_001879 /// NM_139125 | -2.0594 |
| 227236_at | TSPAN2 | tetraspanin 2 | NM_005725 | 2.0511 |
| 229121_at | --- | --- | --- | 2.0474 |
| 238778_at | MPP7 | membrane protein, palmitoylated 7 (MAGUK p55 subfamily member 7) | NM_173496 | 2.045 |

FIG. 11C

| Affimetrix Accession | Gene code | Transcript | Entrez Accession | Fold up-regulation |
|---|---|---|---|---|
| 203638_s_at | FGFR2 | fibroblast growth factor receptor 2 | NM_000141 /// NM_022970 | 2.0273 |
| 204052_s_at | SFRP4 | secreted frizzled-related protein 4 | NM_003014 | -2.0267 |
| 206101_at | ECM2 | extracellular matrix protein 2, female organ and adipocyte specific | NM_001393 | 2.0248 |
| 1561398_at | LOC644620 | Similar to hCG2041997 | XM_001716736 XM_001717475 XM_001718226 | 2.008 |
| 230291_s_at | NFIB | Nuclear factor I/B | NM_005596 | 2.0002 |

FIG. 12

| Target | Sequence | Conditions |
|---|---|---|
| human GAPDH | FOR gagccacatcgctcagaca<br>REV cctcttcaagggtctac | 95°C(30s),<br>50°C (30s),<br>72°C (60s) |
| murine GAPDH | FOR tcgtccgtagacaaaatg<br>REV ttattatggggtctgg | 95°C(30s),<br>50°C (30s),<br>72°C (60s) |
| human GAPDH | FOR ctctctgctcctcctgttcgac<br>REV tgagcgatgtggctcggct | SYBR-green 60°C |
| murine GAPDH | FOR catggccttccgtgttccta<br>REV gcggcacgtcagatcca | SYBR-green 60°C |
| human collagen I | FOR gaacgcgtgtcatcccttgt<br>REV gaacgaggtagtctttcagcaaca | SYBR-green 60°C |
| human collagen III | FOR gggaacaacttgatggtgctact<br>REV tcagacatgagagtgtttgtgcaa | SYBR-green 60°C |
| human collagen V | FOR cacaacttgcctgatggaataaca<br>REV gcagggtacagctgcttggt | SYBR-green 60°C |
| Human collagen VI | FOR ccatcgtgcgcagcc<br>REV tgcgcgactcgtgc | SYBR-green 60°C |
| human collagen XI | FOR gactatcccctcttcagaactgttaac<br>REV cttctatcaagtggtttcgtggttt | SYBR-green 60°C |
| human collagen XII | FOR cttccattgaggcagaagtt<br>REV agacacaagagcagcaatga | SYBR-green 60°C |
| human collagen XV | FOR cgtgttagagatggctgga<br>REV gtttggtggaggcagaag | SYBR-green 60°C |
| human collagen XIV | FOR tccgaggaatggtataaccgg<br>REV tggaccaggaacactgacagg | SYBR-green 60°C |
| human collagen XXI | FOR gcgcaggtcttgctcgggtt<br>REV ctggtgctccggggcaggat | SYBR-green 60°C |

FIG. 21
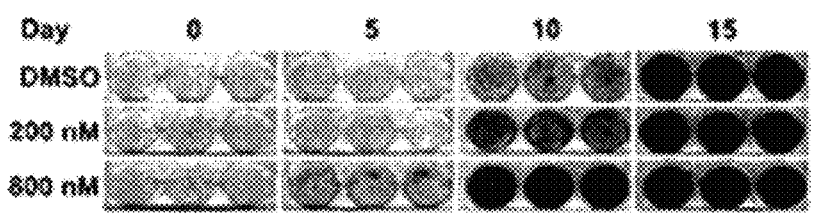
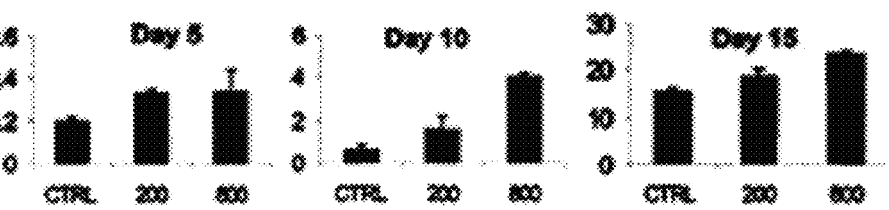
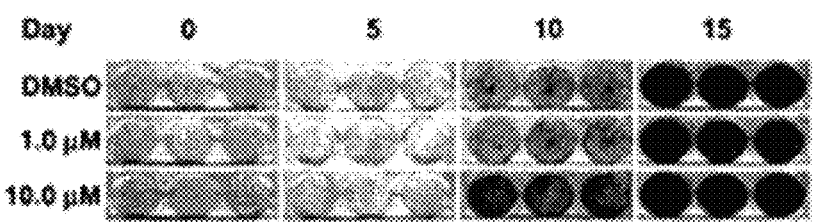
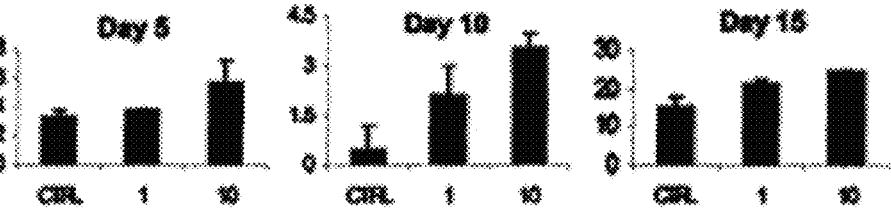

FIG. 26
a.
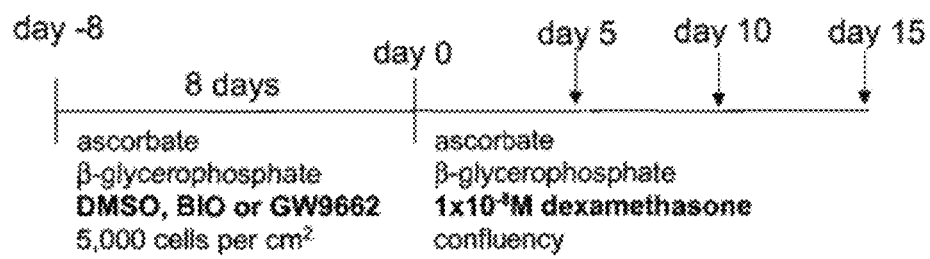
b.
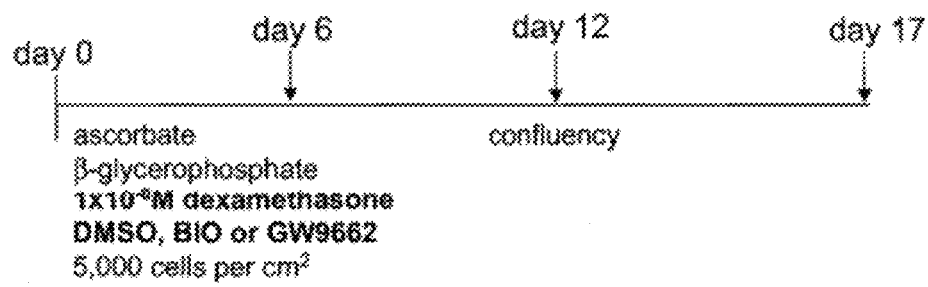
c.
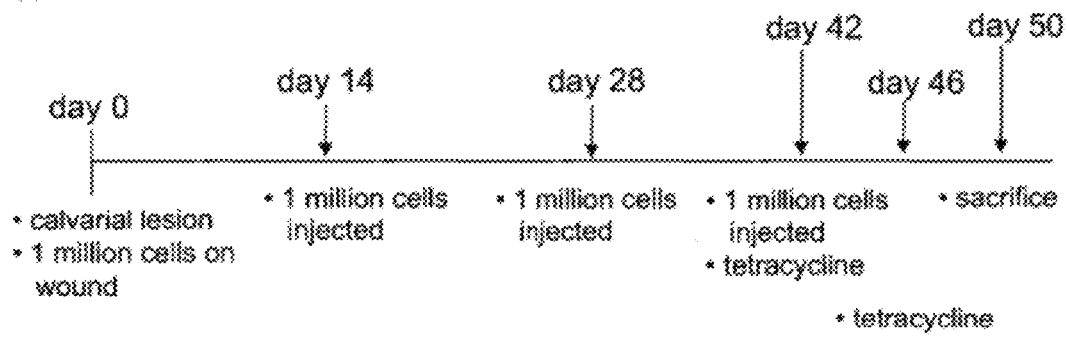

FIG. 35A

| Function | Score |
|---|---|
| Membrane part | 27.5164 |
| Intrinsic to membrane | 26.0127 |
| Integral to membrane | 23.6473 |
| RNA binding | 20.2434 |
| RNA processing | 19.4775 |
| RNA metabolic process | 18.9374 |
| mRNA processing | 18.3833 |
| Membrane | 17.8623 |
| Receptor activity | 16.8981 |
| mRNA metabolic process | 16.1989 |
| Nuclear body | 16.0694 |
| Intracellular part | 15.3947 |
| Transmembrane receptor activity | 15.2885 |
| Regulation of Ras GTPase activity | 15.2184 |
| Regulation of GTPase activity | 14.6939 |
| Nucleoplasm part | 14.2069 |
| Nuclear part | 13.7139 |
| Intracellular organelle | 13.5684 |
| RNA splicing | 13.4278 |
| Signal transducer activity | 13.3653 |
| Molecular transducer activity | 13.3653 |
| Nuclear mRNA splicing, via spliceosome | 13.3446 |
| Regulation of ARF GTPase activity | 13.3796 |
| Nucleotide binding | 13.1939 |
| Collagen | 13.1052 |
| GTPase activator activity | 12.9198 |
| ARF GTPase activator activity | 12.7744 |
| G protein coupled receptor protein signaling pathway | 12.0761 |
| Protein localization | 12.0587 |
| GTPase regulator activity | 11.8790 |
| Response to stimulus | 11.8577 |
| G protein coupled receptor activity | 11.7330 |
| Macromolecule localization | 11.4625 |
| Cellular macromolecule metabolic process | 11.3837 |
| Nuclear speck | 11.3583 |
| Nucleus | 11.3502 |
| Ras GTPase activator activity | 11.0715 |
| Plasma membrane | 11.0056 |
| Immune response | 10.9738 |
| Cytoplasm | 10.8964 |
| Muscle thin filament tropomyosin | 10.7408 |
| Protein binding | 10.7210 |
| Intrinsic to plasma membrane | 10.7024 |
| Protein farnesyltransferase activity | 10.3374 |
| Protein amino acid farnesylation | 10.3374 |
| Hemidesmosome | 10.3374 |
| Integral to plasma membrane | 10.3207 |
| Cellular protein metabolic process | 10.1387 |
| Biopolymer metabolic process | 9.86304 |
| Rhodopsin-like receptor activity | 9.82835 |
| Extracellular region | 9.67791 |
| Intracellular membrane-bounded organelle | 9.62580 |
| Macromolecule metabolic process | 9.45201 |
| Protein modification process | 9.20919 |
| Plasma membrane part | 9.08948 |
| Intracellular transport | 9.01389 |
| Ubiquitin-protein ligase activity | 8.89770 |
| Acid-amino acid ligase activity | 8.72389 |
| Zinc ion binding | 8.68187 |
| Small conjugating protein ligase activity | 8.47253 |
| Neuromuscular junction development | 8.26483 |
| Cellular_component | 8.15432 |

FIG. 35B

| Function | Score |
|---|---|
| Transmembrane transporter activity | 8.14914 |
| NADPH:quinone reductase activity | 8.11148 |
| Polytene chromosome chromocenter | 8.11148 |
| Negative regulation of Rho protein signal transduction | 8.11148 |
| Establishment of localization in cell | 8.01233 |
| ATP-dependent helicase activity | 7.89262 |
| Binding | 7.74701 |
| Transporter activity | 7.71191 |
| Heterogeneous nuclear ribonucleoprotein complex | 7.57409 |
| Golgi to endosome transport | 7.36078 |
| Wnt receptor signaling pathway through beta-catenin | 7.36078 |
| Nucleic acid binding | 7.21703 |
| Posttranslational protein modification | 7.18282 |
| Regulation of small GTPase mediated signal transduction | 7.13643 |
| Metal ion transport | 7.13251 |
| Ligase activity, forming carbon-nitrogen bonds | 7.00821 |
| Localization | 6.80309 |
| Mediator complex | 6.78123 |
| Transition metal ion binding | 6.77774 |
| Ubiquitin-dependent protein catabolic process | 6.74139 |
| Extracellular space | 6.64369 |
| Double-stranded DNA binding | 6.62313 |
| Polynucleotide adenylyltransferase activity | 6.61480 |
| Farnesyltranstransferase activity | 6.61480 |
| Receptor tyrosine kinase binding | 6.61480 |
| Beta-N-acetylhexosaminidase activity | 6.61480 |
| Vesicle | 6.61480 |
| Organelle | 6.61480 |
| Protein import into mitochondrial matrix | 6.61480 |
| Fibrillar collagen | 6.60614 |
| Camera-type eye morphogenesis | 6.60614 |
| Modification-dependent protein catabolic process | 6.54899 |
| Multicellular organismal process | 6.49879 |
| Channel activity | 6.48427 |

Enrichment scores are derived from P values ($10^{enrichment\ score}$ = P value against the probability that a given gene clustered based on chance alone).

FIG. 36

| Protein | Gene | Accession No. | Fold changes BIO200 | BIO800 | GW1 | GW10 | Major location/function |
|---|---|---|---|---|---|---|---|
| *Collagen Iα1* | *COL1A1* | 217430_x_at | 2.75 | 2.79 | 2 | 3 | Abundant in bone |
| *Collagen Iα1* | *COL1A1* | 202311_s_at | 2.38 | 2.2 | 2.05 | 2.25 | |
| *Collagen Iα2* | *COL1A2* | 225664_at | 2.38 | 1.88 | 1.79 | 3.93 | Abundant in bone |
| *Collagen IIIα1* | *COL3A1* | 232458_at | 3.12 | 1.22 | 10.4 | 2.8 | Present in bone |
| Collagen IVα5 | COL4A5 | 213110_s_at | −2.05 | −2.65 | −1.84 | −1.29 | Low/absent in bone |
| Collagen Vα3 | COL5A3 | 53255_s_at | 1.91 | 1.12 | 1.52 | 3.34 | Present/low in bone |
| *Collagen VI α1* | *COL6A1* | 212091_s_at | 1.92 | 1.66 | 1.85 | 3.23 | Present in bone |
| *Collagen VI α1* | *COL6A1* | 212940_s_at | 2.05 | 1.66 | 1.14 | 2.99 | |
| *Collagen VI α2* | *COL6A2* | 209156_s_at | 1.96 | 1.31 | 2.38 | 2.71 | Present in bone |
| Collagen VIIIα1 | COL8A1 | 221152_at | 1.43 | 1.12 | 4.07 | 1.57 | Low in bone |
| Collagen VIIIα2 | COL8A2 | 52651_at | 2.12 | 2.43 | 1.14 | 1.24 | Low in bone |
| Collagen Xα1 | COL10A1 | 217428_s_at | 1.65 | 2.18 | 1.37 | 1.47 | Present in mature bone |
| Collagen XIα1 | COL11A1 | 229271_x_at | −1.94 | −1.02 | 2.38 | 5.01 | Cartilage restricted |
| Collagen XIα1 | COL11A1 | 37982_at | −2.2 | −3.29 | 5.57 | 4.02 | |
| *Collagen XIIα1* | *COL12A1* | 231766_s_at | 2.38 | 1.88 | 1.79 | 3.93 | Present in bone |
| *Collagen XIIα1* | *COL12A1* | 225664_at | 1.5 | 1.29 | 1.23 | 2.79 | |
| *Collagen XIIα1* | *COL12A1* | 231879_at | 2.11 | 1.62 | 1.13 | 4 | |
| Collagen XIVα1 | COL14A1 | 212865_s_at | −3.47 | −4.59 | −2.28 | 2.2 | Marrow stroma |
| Collagen XVα1 | COL15A1 | 203477_at | −1.83 | −2.25 | 2.03 | 2.04 | Some osteoblasts |
| Aggrecan | ACAN | 217161_x_at | 1.09 | 1.2 | 1.3 | 2.7 | Cartilage restricted |
| Fibronectin | FN1 | 1558199_at | 1.88 | 1.87 | 7.29 | 2.6 | Synthesizing bone |

Bone-related collagens are italicized in the first two columns; high abundance bone-related collagens are bold. Significant fold increases are presented in bold in columns 4–6; significant fold decreases are presented in italic.

FIG. 37

| Function | Score |
|---|---|
| Highly down-regulated in BIO-treated MSCs, moderately down-regulated in GW9662-treated MSCs. | |
| Thrombin receptor activity | 28.0695 |
| Trans-1,2-dihydrobenzene-1,2-diol dehydrogenase activity | 28.0695 |
| 3-Alpha-hydroxysteroid dehydrogenase (A-specific) activity | 22.5322 |
| Prostanoid metabolic process | 17.3850 |
| Prostaglandin metabolic process | 17.3850 |
| Phospholipid scrambling | 14.8662 |
| Phospholipid scramblase activity | 14.8662 |
| Bile acid binding | 14.8662 |
| Acetylgalactosaminyltransferase activity | 13.6365 |
| Platelet-derived growth factor receptor activity | 12.6591 |
| Response to dsRNA | 12.6591 |
| Prostaglandin E receptor activity | 12.6591 |
| Indole and derivative metabolic process | 12.6591 |
| Indole derivative metabolic process | 12.6591 |
| Regulation of ossification | 11.3625 |
| Carboxylic acid binding | 10.9963 |
| 3',5'-Cyclic-nucleotide phosphodiesterase activity | 10.7854 |
| Steroid dehydrogenase activity, acting on the CH-OH group of donors, NAD or NADP as acceptor | 10.3329 |
| Cyclic-nucleotide phosphodiesterase activity | 10.3329 |
| Adenylate kinase activity | 9.89717 |
| Integrin complex | 8.79613 |
| Highly down-regulated in GW9662 treated MSCs, moderately down-regulated in BIO treated MSCs | |
| Sphingomyelin biosynthetic process | 21.4244 |
| Extracellular region | 18.6676 |
| Sphingomyelin synthase activity | 16.4884 |
| Ceramide cholinephosphotransferase activity | 16.4884 |
| Cytoplasmic part | 16.1806 |
| Stearoyl-CoA 9-desaturase activity | 12.2139 |
| Intracellular part | 11.1996 |
| Intracellular organelle part | 10.5470 |
| Y-form DNA binding | 9.63809 |
| Transcription, RNA-dependent | 9.63809 |
| Negative regulation of retroviral genome replication | 9.63809 |
| Ubiquitin-dependent protein catabolic process | 9.59400 |
| Endoplasmic reticulum | 9.49858 |
| Modification-dependent protein catabolic process | 9.35670 |
| Golgi-associated vesicle | 8.89415 |
| Signal transduction | 8.86723 |
| Extracellular region part | 8.62576 |
| Nucleosome assembly | 8.59450 |
| Protein import | 8.48881 |
| Nucleosome | 8.18840 |
| Regulation of defense response to virus by host | 8.02484 |
| Extracellular space | 7.99858 |

Enrichment scores are derived from P values (10^(enrichment score × -1) = P value against the probability that a given gene clustered based on chance alone).

FIG. 38

| Function | Score |
|---|---|
| Positive regulation of epidermal growth factor receptor activity | 83.2623 |
| Neutrophil chemotaxis | 79.0106 |
| G protein-coupled receptor binding | 68.7486 |
| Chemokine activity | 67.9314 |
| Fever | 65.5733 |
| Chemokine receptor binding | 65.4490 |
| Regulation of protein secretion | 58.0544 |
| Epidermal growth factor receptor activating ligand activity | 52.4821 |
| Leukocyte chemotaxis | 50.0283 |
| Epidermal growth factor receptor binding | 48.2312 |
| Response to wounding | 44.179 |
| Respiratory burst | 43.7386 |
| Heat generation | 43.7386 |
| Positive regulation of phosphorylation | 43.7127 |
| Positive regulation of cell cycle | 42.6954 |
| Leukocyte migration | 40.3008 |
| Inflammatory response | 40.1391 |
| Positive regulation of phosphate metabolic process | 38.4481 |
| Regulation of interleukin-6 biosynthetic process | 38.3896 |
| Plasminogen activator activity | 37.4817 |
| Positive regulation of interleukin-6 biosynthetic process | 37.4817 |
| Macrophage chemotaxis | 37.4817 |
| Lymphocyte chemotaxis | 37.4817 |
| Induction of programmed cell death in response to chemical stimulus | 33.7693 |
| Regulation of short-term neuronal synaptic plasticity | 33.7693 |

Enrichment scores are derived from $P$ values ($10^{-enrichment\ score}$ = $P$ value against the probability that a given gene clustered based on chance alone).

FIG. 39

| Protein | Gene | Accession | Fold Changes | | | | Major known function | Ligand confirmed |
|---|---|---|---|---|---|---|---|---|
| | | | BIO200 | BIO800 | GW1 | GW10 | | |
| Interleukin 1A | IL1A | 210118_s_at | 2.33 | 2.88 | -2.87 | -2.15 | Pro-inflammatory | n.d. |
| Interleukin 1B | IL1B | 205067_at | 3.07 | 2.42 | -3.15 | -4.40 | Pro-inflammatory | Yes |
| Interleukin 8 | IL8 | 20842_s_at | 2.8 | 6.38 | -5.23 | -6.70 | Pro-inflammatory | Yes |
| Interleukin 8 | IL8 | 202859_s_at | 1.56 | 2.99 | -6.48 | -18.97 | | |
| CXC ligand 1 (GROα) | CXCL1 | 204470_at | 1.58 | 2.85 | -5.83 | -8.27 | Neutrophil attractant | Yes |
| CXC ligand 2 | CXCL2 | 209774_x_at | -1.23 | 1.31 | -4.49 | -5.63 | Leukocyte attractant | No |
| CXC ligand 5 (ENA-78) | CXCL5 | 214974_x_at | 1.03 | 3.6 | -1.08 | -1.16 | Neutrophil attractant | Yes |
| CXC ligand 6 (GCP-2) | CXCL6 | 206336_at | -1.25 | 1.49 | -3.33 | -5.12 | Neutrophil attractant | Yes |
| Interleukin 7 | IL7 | 206693_at | -3.3 | -3.19 | -3.38 | -3.29 | Lymphoid mitogen | n.d. |

Significant fold increases are presented in bold in columns 4-6; significant fold decreases are presented in italic; n.d. = not detected

FIG. 40

| Ligand | DMSO* | GW1.0* | GW10.0* | BIO300 | BIO600 |
|---|---|---|---|---|---|
| IL-1 beta† | $4.5 \times 10^{-5}$ | $4.5 \times 10^{-6}$ | BDL | NC | NC |
| IL-8† | $1.6 \times 10^{-5}$ | $3.5 \times 10^{-6}$ | $6.8 \times 10^{-7}$ | NC | NC |
| CXCL1§ | 0.01 | 0.001 | $7.2 \times 10^{-6}$ | NC | NC |
| CXCL2† | 0.01 | 0.0016 | $5.8 \times 10^{-4}$ | NC | NC |
| CXCL6‡ | 0.07 | 0.005 | BDL | NC | NC |

BDL, below detectable levels; NC, no significant change.
*Nanograms secreted per cell per 48 h.
†ELISA intra-assay variation <7.5%.
§ELISA intra-assay variation <5%.
‡ELISA intra-assay variation <10%.

FIG. 41

| Treatment | Animal number | | | Mean | SD | P (Student's t test) |
|---|---|---|---|---|---|---|
| | 1 | 2 | 3 | | | |
| DMSO | 235 | 141 | 206 | 194 | 48.13 | Versus DMSO |
| BIO200 | 12 | 52 | 0 | 21.33 | 27.23 | 0.0057 |
| BIO800 | 11 | 0 | 31 | 14 | 15.72 | 0.003 |
| GW1.0 | 362 | 198 | 347 | 260.67 | 90.47 | ns |
| GW10.0 | 341 | 215 | 232 | 262.67 | 68.36 | ns | ns, not significant.

MESENCHYMAL STEM CELLS AND SUPPORTS FOR TISSUE REGENERATION, REPAIR AND RECONSTRUCTION

CROSS-REFERENCE TO RELATED APPLICATION

This application claims the benefit of U.S. patent application Ser. No. 12/730,022 filed Mar. 23, 2010, which claims the benefit of U.S. Provisional Application No. 61/210,764, filed Mar. 23, 2009; each of which are hereby incorporated by reference in their entirety and to the fullest extent allowable.

STATEMENT REGARDING FEDERALLY SPONSORED RESEARCH OR DEVELOPMENT

The disclosed was made with government support under R21 DK071780 and P20RR020152-01 awarded by the National Institutes of Health. The government has certain rights in limited circumstances.

TECHNICAL FIELD

As disclosed herein are supporting materials and method of making said biocompatible materials for in vivo and in situ applications.

BACKGROUND

Tissue repair and reconstruction requires the reconstructive material to be biocompatible with its host. In addition, said material must also cooperate with the regenerative and repair processes in order for new tissue to suitably form in three-dimensions with adequate strength and stability. Unfortunately, many current materials are often poorly suited for proper support of regenerative cells required for reconstruction. In addition, many regenerative processes are inadequate and end up with failure or require further surgical time, which leads to higher cost and increased complications.

SUMMARY

Described herein are materials and methods for reconstruction of one or more tissue types, including bone tissue.

Further described herein are materials and methods for conditioning a solid material for use with said one or more tissue types.

Still further, described herein are materials and methods for providing a solid material in a cryogenic state, thus cryogenically preserved and suitable for use at point of care.

Even further as described herein are one or more cellular materials for reconstruction of a tissue, said cellular material capable of being cryogenically preserved for later use at point of care;

In one or more forms are described a composition comprising mesenchymal stem cells (MSCs) initially pre-treated for differentiation into osteogenic cells and an extracellular matrix mixture comprising components produced by mesenchymal stem cells pre-treated for differentiation into osteogenic cells. The mesenchymal stem cells are pretreated with an inhibitor of peroxisome proliferator-activated receptor gamma. The mesenchymal stem cells may be pretreated with 2-chloro-5-nitro-N-phenyl-benzamide. The mesenchymal stem cells are generally pre-treated for five days to 2 weeks. The mesenchymal stem cells exhibit increased alkaline phosphatase activity after pre-treatment. The mesenchymal stem cells produce calcium after pre-treatment. The mesenchymal stem cells produce extracellular matrix nodules after pre-treatment and an upregulation in gene expression for collagen types I, III, V, VI, XI, XII, XIV, XV and XXI as compared with extracellular matrix produced by mesenchymal stem cells not pre-treated for differentiation into osteogenic progenitor cells. The extracellular matrix mixture exhibits is rich in collagens associated with an increased lysine level and a reduced hydroxyproline as compared with extracellular matrix produced by mesenchymal stem cells not pre-treated for differentiation into osteogenic progenitor cells. The extracellular matrix mixture includes collagens that play role in skeletal development and/or accelerated osteoblast activity as well as one that is highest in highly vascularized tissues such as heart, stomach and placenta. The extracellular matrix is generally recovered from the MSCs by lyses, enzymatic digestion(s), solvent extraction(s) and washing(s) to remove the cells and other contaminating proteins while maintaining certain components, including collagen-rich components of the ECM. After processing, the extracellular matrix mixture may have a fibrous appearance at low magnification and have distinct, regularly oriented fibrils when examined by scanning electron microscopy. The extracellular matrix mixture may be produced by independent mesenchymal stem cells and extracted and separated from the independent mesenchymal stem before incorporating into the composition. The composition when administered to a bone tissue defect enhances retention signals for mesenchymal stem cells to remain at or near the bone tissue defect during a remodeling phase of healing.

Also described is a composition comprising a three-dimensional scaffold for repair or reconstruction of bone tissue, an extracellular matrix mixture in contact with the three-dimensional scaffold, the extracellular matrix mixture comprising components produced and extracted from mesenchymal stem cells pre-treated for differentiation into osteogenic cells, and optionally comprising mesenchymal stem cells initially pre-treated for differentiation into osteogenic cells and in contact with the three-dimensional scaffold. The extracellular matrix mixture prior to contact the three-dimensional scaffold is extracted from mesenchymal stem cells after pretreatment with an inhibitor of peroxisome proliferator-activated receptor gamma. The extracellular matrix mixture is rich in collagen types I, III, V, VI, XI, XII, XIV, XV and XXI. The extracellular matrix mixture is in contact with the three dimensional scaffold by incubating mesenchymal stem cells with the three dimensional scaffold for at least one week in the presence of an inhibitor of peroxisome proliferator-activated receptor gamma. The cells may be further incubated for a period of time with media containing supplement(s) that promote mineralization. The mesenchymal stem cells are removed prior to use of the composition for repair or reconstruction of bone tissue. The composition may be cryogenically preserved. The composition may be decellularized and then re-seeded with new mesenchymal stem cells that have been initially pre-treated for differentiation into osteogenic cells prior to use of the composition for repair or reconstruction of bone tissue.

In addition embodiments are described a composition comprising a three-dimensional scaffold for repair or reconstruction of bone tissue and an extracellular matrix mixture in contact with the three-dimensional scaffold, the extracellular matrix mixture comprising components produced and extracted from mesenchymal stem cells pre-treated for differentiation into osteogenic cells, wherein the composition is capable of cryogenic preservation with or without decellularization. Prior to use and/or after cryogenic preservation the scaffold may be reseeded with mesenchymal stem cells pre-treated for differentiation into osteogenic cells. The extracellular matrix mixture is in contact with the three-dimensional scaffold after initially culturing with the mesenchymal stem cells and then decellularizing the three-dimensional scaffold with a series of enzyme treatments and washes

BRIEF DESCRIPTION OF THE DRAWINGS

Various embodiments will be explained in more detail with reference to the drawings in which:

FIGS. 5A-5D depict representative examples in vivo after defect repair and reconstruction as described herein, in which groups during surgery received only pretreated hMSCs, only ECM (recovered from pretreated hMSCs) or both and all were re-administered with pretreated cells at 1 and at 2 weeks post surgery, such that after 3 weeks, the defects were analyzed by microCT (FIG. 5A, top), by H&E stained (FIG. 5A, bottom), by radio-opacity of the lesions as in FIG. 2D (FIG. 5B), by relative calvarial human GAPDH expression as in FIG. 2B (FIG. 5C, n=4), and by immunostaining of specimens with human β2-microglobulin (green) demonstrating the presence of elongated clusters of hMSCs at the surface of the bone when only pretreated cells were administered the absence of ECM (FIG. 5D, left) as compared with numerous cells exclusively within the matrix upon co-administration of pretreated cells and ECM (FIG. 5D, right);

FIGS. 7A-7G depict another representative immunophenotypic analyses of a cell type described herein;

FIG. 10, comprising FIGS. 10A through 10F, depicts representative identification of genes one week after treatment as described herein, in which up-regulated collagen transcripts are identified by "*";

FIG. 11, comprising FIGS. 11A through 11C, depicts a representative identification of genes two weeks after treatment as described herein;

FIG. 12 illustrates representative primer sets used as described herein;

FIGS. 15A and 15B depicts a series of illustrations depicting the effect of Dkk-1 (FIG. 15A) or the PPARγ agonist, troglitazone (FIG. 15B) on alkaline phosphatase (ALP) activity and osteoprotegerin (OPG) secretion. ALP activity was visualized by staining and measured by colorimetric assay. OPG was measured from the medium by ELISA. Values were normalized to cell number. Data are means±SD (n=6), $p<0.05^*$, $p<0.01^{**}$.

FIG. 16A includes 3 bar graphs depicting monolayers of hMSCs from 3 donors (A, B, and C) exposed to complete media (CCM, see none), CCM with osteogenic base supplements, 5 mM β-glycerophosphate and 50 μg·mL-1 ascorbic acid (osteogenic base media, see OBM), OBM with various concentrations (in ng·mL-1) of either bone morphogenic protein 2 (BMP2, see BMP100 or BMP200), or dexamethasone ($10^{-8}$ M, see dex). Note that the ALP levels are substantially raised by OBM treatment and can be improved further by high concentrations of BMP2 (n=3). FIG. 16B depicts the effect of 50 μM of various PPARγ agonists on ALP activity measured by colorimetric assay. All values were normalized to cell number. Data are expressed as means with standard deviations (n=6). Pioglitazone (pio), rosiglitazone (ros), ciglitazone (cig), and troglitazone (trog) were used. FIG. 16C includes two images demonstrating that in the presence of high concentrations of PPARγ agonists, osteogenic cultures of hMSCs initiate adipogenesis rather than osteogenesis. After 20 days of differentiation in OBM containing $10^{-8}$ M dex and 10 μM troglitazone, cultures show Oil Red 0-positive lipid islands (left) and only weak mineralization (Alizarin red S [ARS] staining, right).

FIGS. 17A through 17D, depicts a series of images depicting the effects of BIO and GW. FIG. 17A demonstrates that BIO and GW are predicted to up-regulate Wnt signaling by direct inhibition of GSK3β or by ablating PPARγ mediated negative crosstalk respectively. FIG. 17B is an image of a fluorescent microscopy of hMSCs with counterstained nuclei (pico-green, left) or cy-3 labeled anti-β-catenin stained nuclei (right). FIG. 17C depicts immunoblots of cytosolic GSK3β (C GSK3(β), nuclear β-catenin (N (β-cat) and nuclear PPARγ (N-PPARγ) on extracts of hMSCs treated with BIO or GW. Blots were normalized for cytosolic proteins with GAPDH(C GAPDH) and for nuclear proteins by silver stain. FIG. 17D depicts immunoblots of whole cell and cytosolic extracts of hMSCs.

FIGS. 18A and 18B depicts a series of images depicting cell cycle analysis of vehicle, BIO-, and GW-treated cells after 8 days in culture. FIG. 18A is an image depicting DNA content measured by propidium iodide incorporation, followed by fluorescent activated cell sorting. All cultures had similar cell cycle profiles, with the predominant population in $G_1$, suggesting a degree of contact inhibition. Although cells treated with 800 nM BIO were semiconfluent, the cell cycle status of these hMSCs was similar to the other groups, suggesting cell cycle inhibition that was not related to culture density. Representative cultures of control, BIO-, and GW-treated cells counterstained with eosin are presented with the cell cycle profiles to demonstrate the relative culture densities. FIG. 18B is an image depicting immunoblots of cleaved caspase-3 (Asp175) on whole cell extracts of hMSCs treated with BIO or GW. There is no evidence of caspase 3 processing. Note the potential cross reactivity with procaspase 3. Blots were normalized with GAPDH.

FIGS. 19A through 19D depicts a series of images depicting hMSCs incubated in osteogenic media with BIO or GW. After 8 days of culture, ALP activity was measured (FIG. 19A) and normalized to cell number (FIG. 19D). OPG and Dkk-1 was measured from the media by ELISA (FIGS. 19B and 19C). Data are means±SD (n=6), p-values $p<0.05^*$, $p<0.01^{**}$.

FIG. 21 comprising FIGS. 21A and 21B depicts a series of images depicting hMSCs incubated in osteogenic media containing BIO or GW for 8 days. The cultures then received dex containing osteogenic media for a further 15 days (FIG. 26A). Cultures were stained for calcium with ARS. For semi-quantification, the stain was re-extracted and measured spectrophotometrically. Both BIO (FIG. 21A) and GW (FIG. 21B) pre-treatment enhanced mineralization.

FIGS. 22A and 22B depicts a series of imaged depicting osteoinductive properties of clotted human plasma. Confluent cultures were partially overlaid with clotted plasma. FIG. 22A is an image depicting osteogenic medium containing dex or control medium, and differentiation proceeded for 10-20 days. FIG. 22B is an image demonstrating that after 10 days, cultures were stained with ARS to visualize calcium. When treated for 10 days, only the hMSCs in contact with the plasma mineralized.

FIGS. 23A and 23B depicts a series of images depicting cultures incubated in osteogenic media containing dex and BIO or GW (FIG. 26B). After 17 days, monolayers were stained for calcium with ARS (FIG. 23A).

Figure 23:
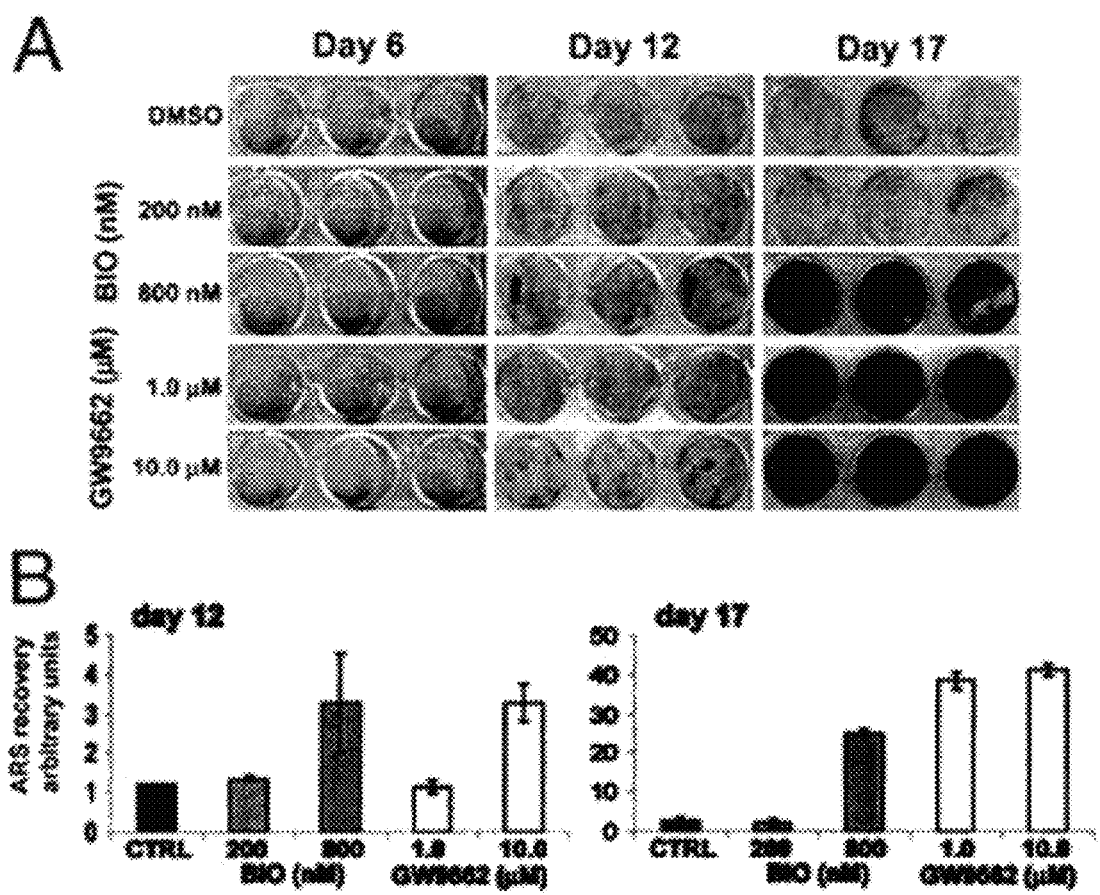
FIG. 23 comprising

For semi-quantification, the stain was re-extracted and measured spectrophotometrically (FIG. 23B).

Figure 24:
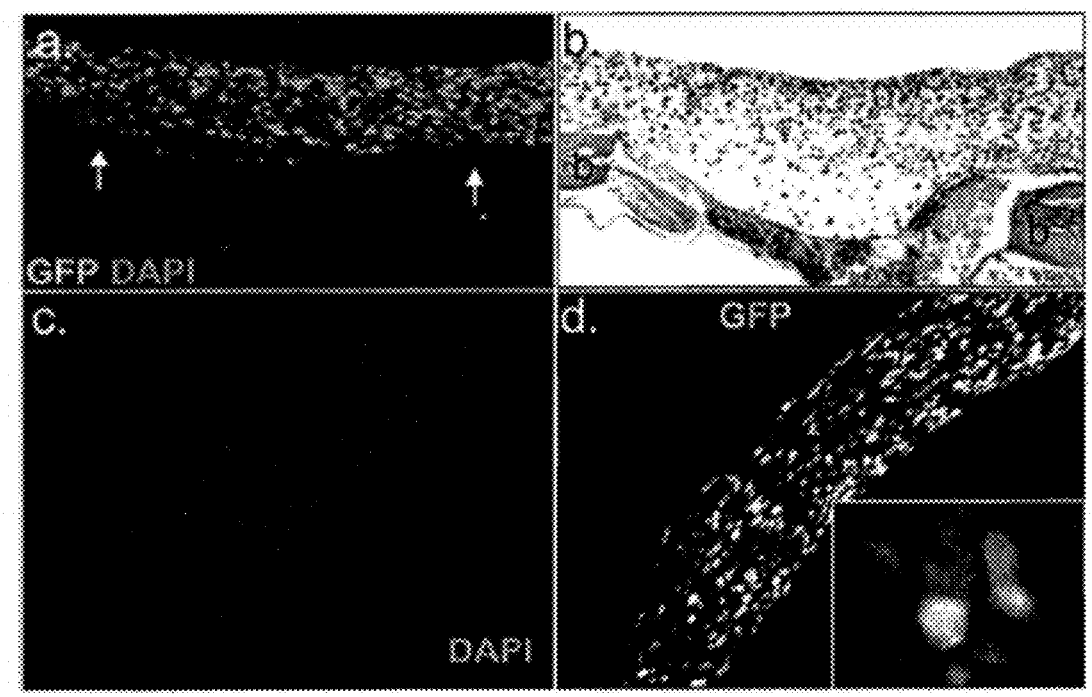

FIG. 24 comprising FIGS. 24A through 24D depicts a series of images depicting immunohistochemistry of 24-h-old calvarial lesions loaded with GFP-labeled hMSCS. (24A and 24B) GFP-labeled hMSCs administered above the lesion (arrowed). (24C and 24D) Immunocytochemistry for hMSCs by using an anti-humanβ-2 microglobulin antibody. The staining is localized exclusively to the GFPlabeled hMSCs, with the expected membranous distribution (24D Inset).

Figure 25:
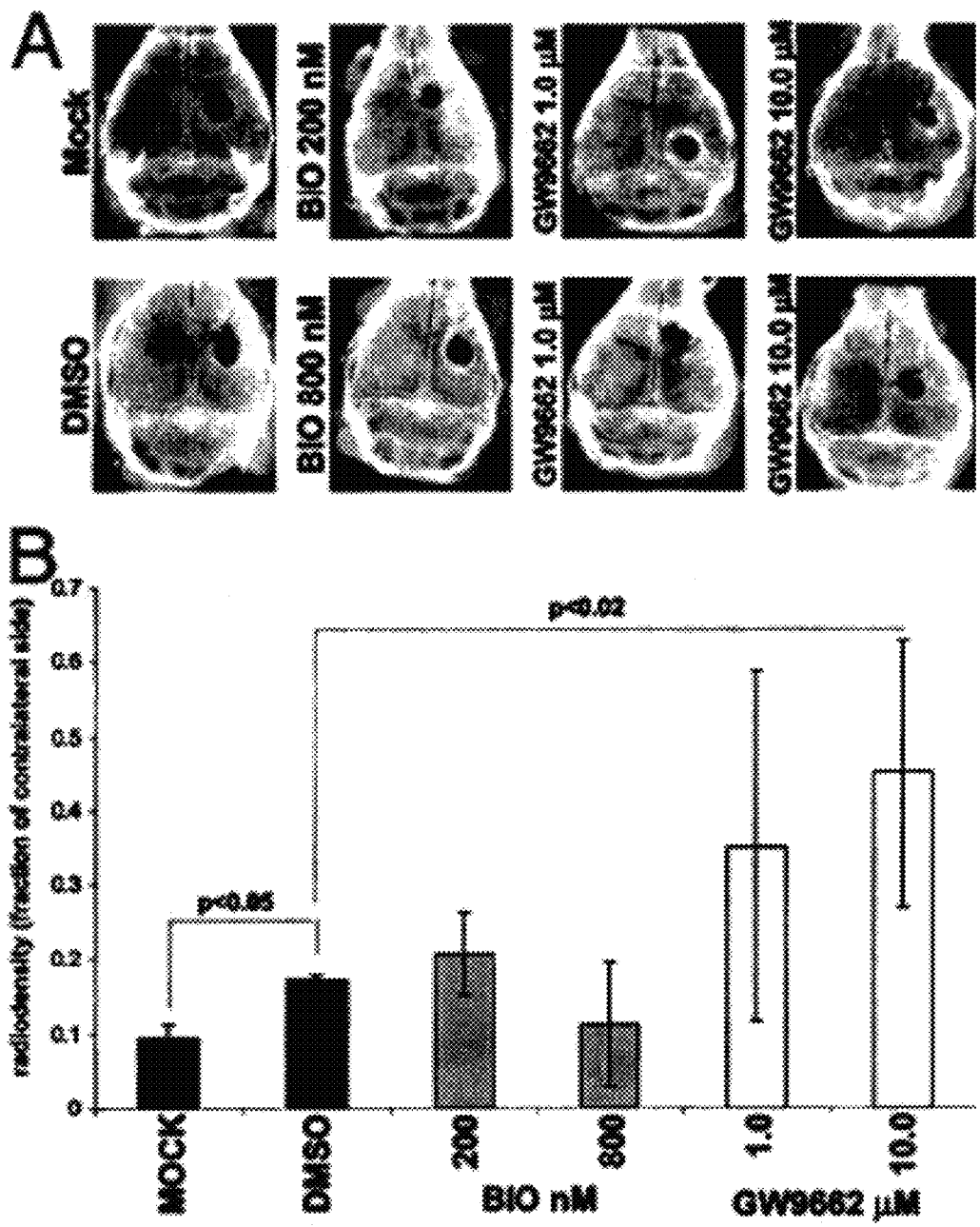

FIG. 25 comprising FIGS. 25A and 25B depicts a series of images depicting 3 mm diameter calvarial defects induced in nude mice. One million hMSCs pretreated with BIO or GW were mixed with plasma and administered to the bone lesion. Subsequent doses were injected at 14 day intervals until day 50 (FIG. 26C). FIG. 25A depicts x-rays of explanted crania. For the GW group, specimens representing the range of the standard deviations are presented. FIG. 25B depicts the ratio of lesioned to contralateral (intact side) radio-opacity calculated by image analysis software. Data are means±SD (n=6, n=5 for mock) p-values *<0.05, **<0.01.

FIG. 26 comprising FIGS. 26A-26C depicts a series of imaged depicting experimental timelines. FIG. 26A depicts an assay of BIO and GW pretreatment on late-stage osteogenesis. FIG. 26B is an assay simultaneous BIO and GW treatment on late-stage osteogenesis. FIG. 26C is an assay of in vivo bone repair.

Figure 27:
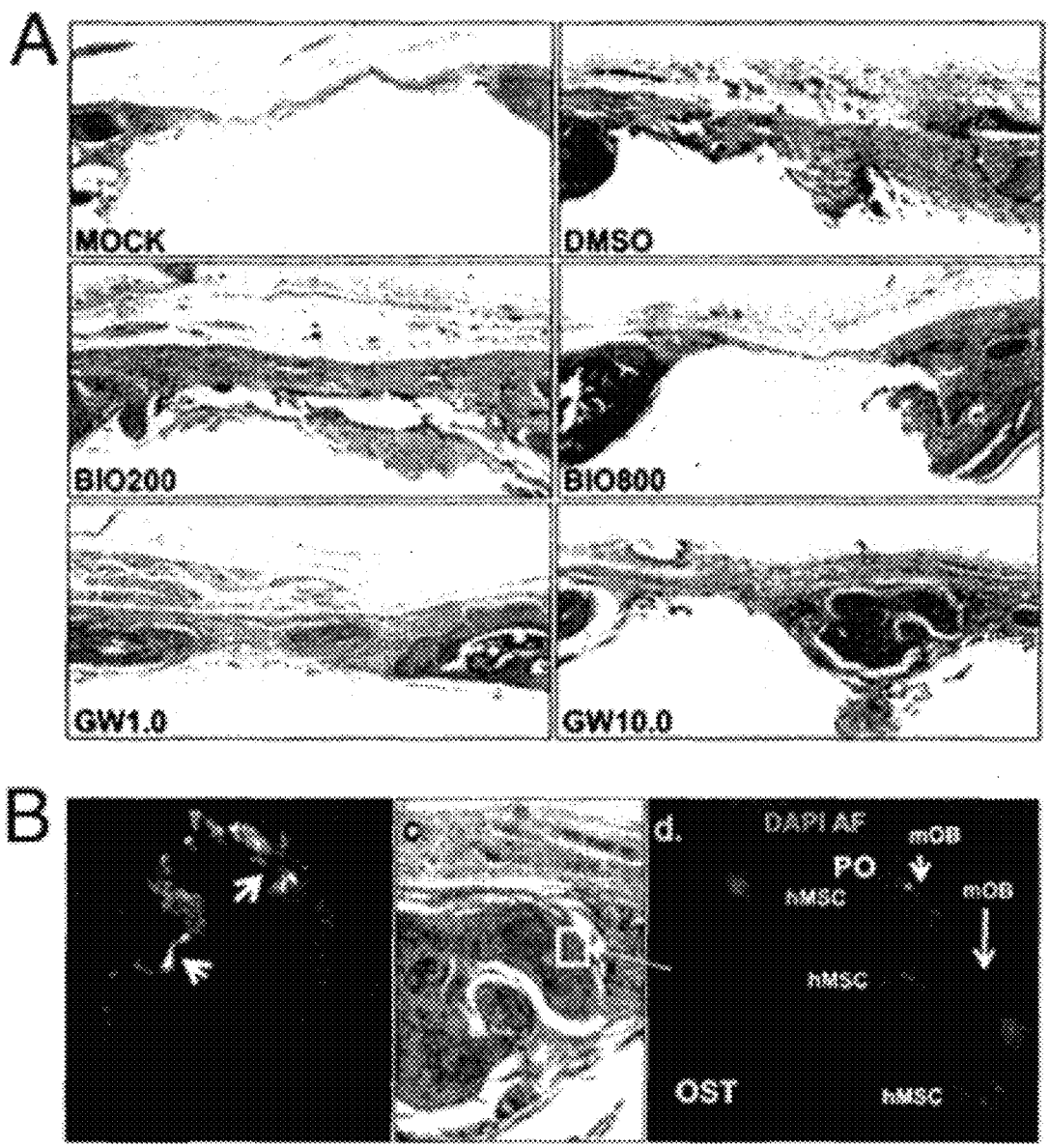

FIG. 27 comprising FIGS. 27A-27D depicts a series of images depicting new bone formation in the GW treated groups. FIG. 27A is an image depicting a hematoxylin and eosin (H&E) stained longitudinal sections at the diameter of the lesions. New bone can be observed in the GW treated injuries. FIG. 27B is an image depicting an ultraviolet microscopy of transverse sections for tetracycline (new bone) deposition (arrowed). FIGS. 27C and 27D show a series of images depicting immuno-histochemical staining of hMSCs embedded in new bone of the GW treated calvaria. Unstained murine osteoblasts (mOB) are also visible.

Figure 28:
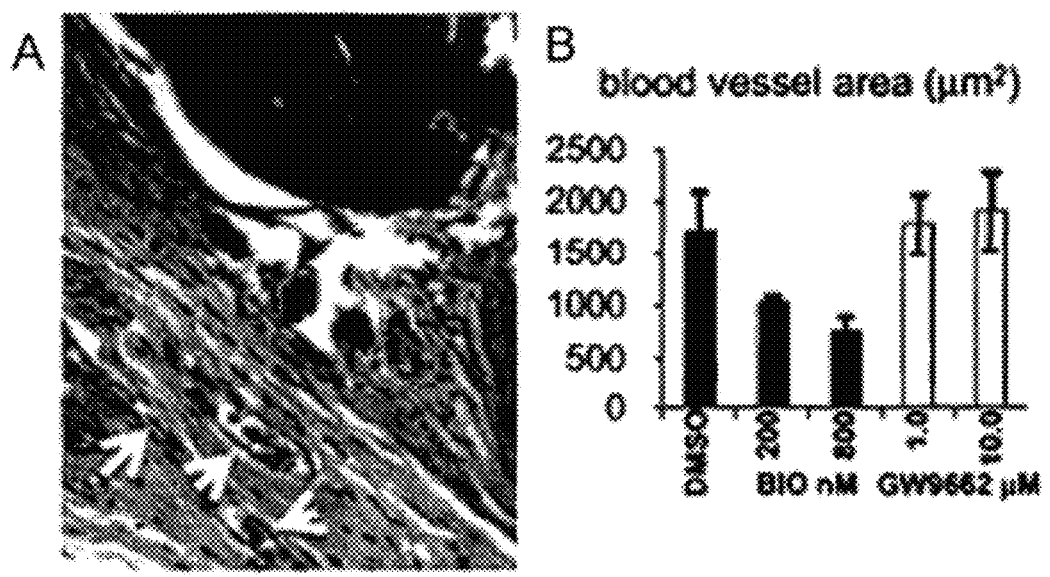

FIG. 28 comprising FIGS. 28A and 28B depicts a series of images demonstrating that GW treatment did not affect the ability of MSCs to initiate angiogenesis at trauma sites. FIG. 28A is an image demonstrating that blood vessels were identified on hematoxylin/eosin-stained sections (arrowed) corresponding to 0.5 mm either side of the diameter of the lesion. FIG. 28B is an image depicting six μm sections that were surveyed every 30 μm and blood vessel area was calculated. Data are means±SD (n=3 animals).

Figure 29:

FIG. 29 is a schematic of a representative extraction process for the extraction of a biocompatible lattice from hMSCs.

Figures 30A, 30B, 30C, 30D:
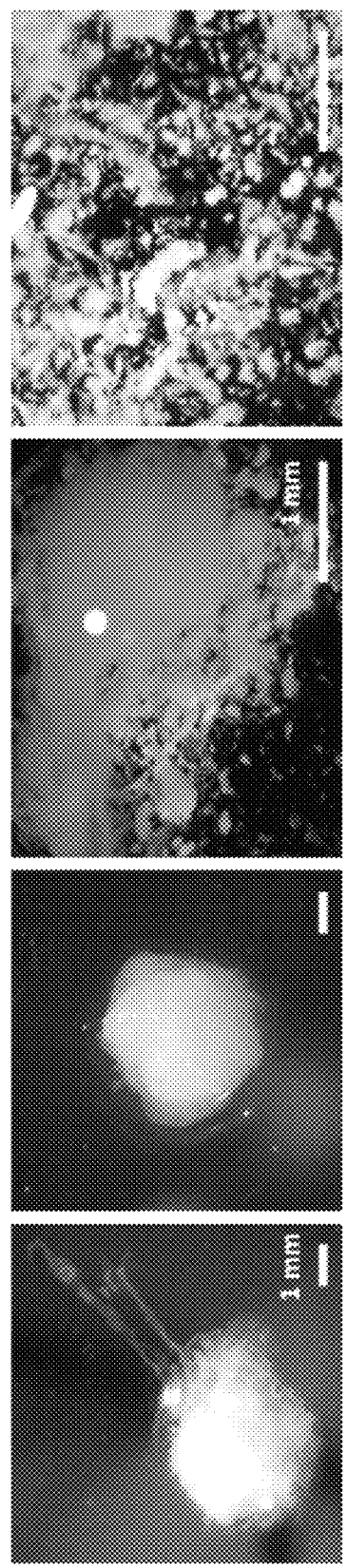

FIG. 30 comprising FIGS. 30A-30D depicts a series of images of Extracellular Matrix (ECM) that was extracted from MSC's after three or six weeks of osteogenic differentiation following the protocol shown in FIG. 29. Short-term culture produces malleable constructs (FIGS. 30A, 30B), whereas increased calcification after long-term culture creates more brittle material (FIG. 30C, 30D). Trypsin-treated ECM (FIG. 30A, 30C) is more fibrous than untreated ECM (FIG. 30B, 30D). Bar=1 mm.

Figure 31:
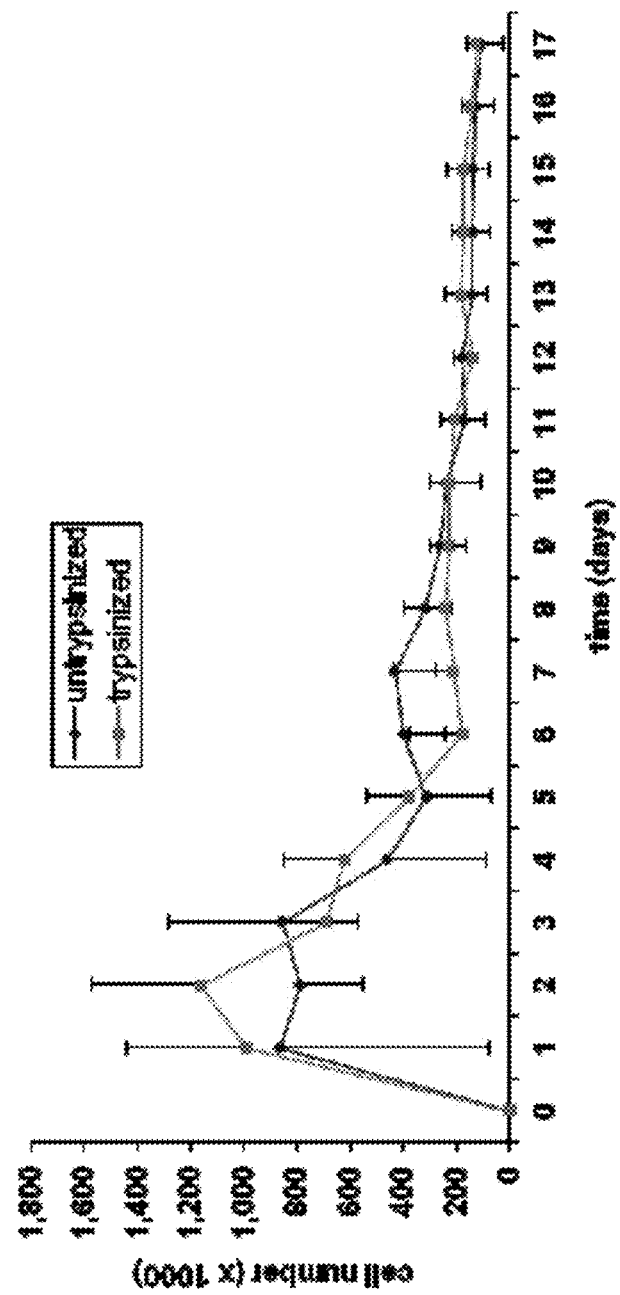

FIG. 31 is a chart demonstrating that both untreated and trypsin-treated matrices were able to sustain cell viability. One million GFP-positive MSC's were seeded onto matrices in CCM. After four days, cultures were changed to osteogenic medium. Cell numbers stabilized after osteogenic differentiation (n=5 or 4, respectively).

Figure 32:
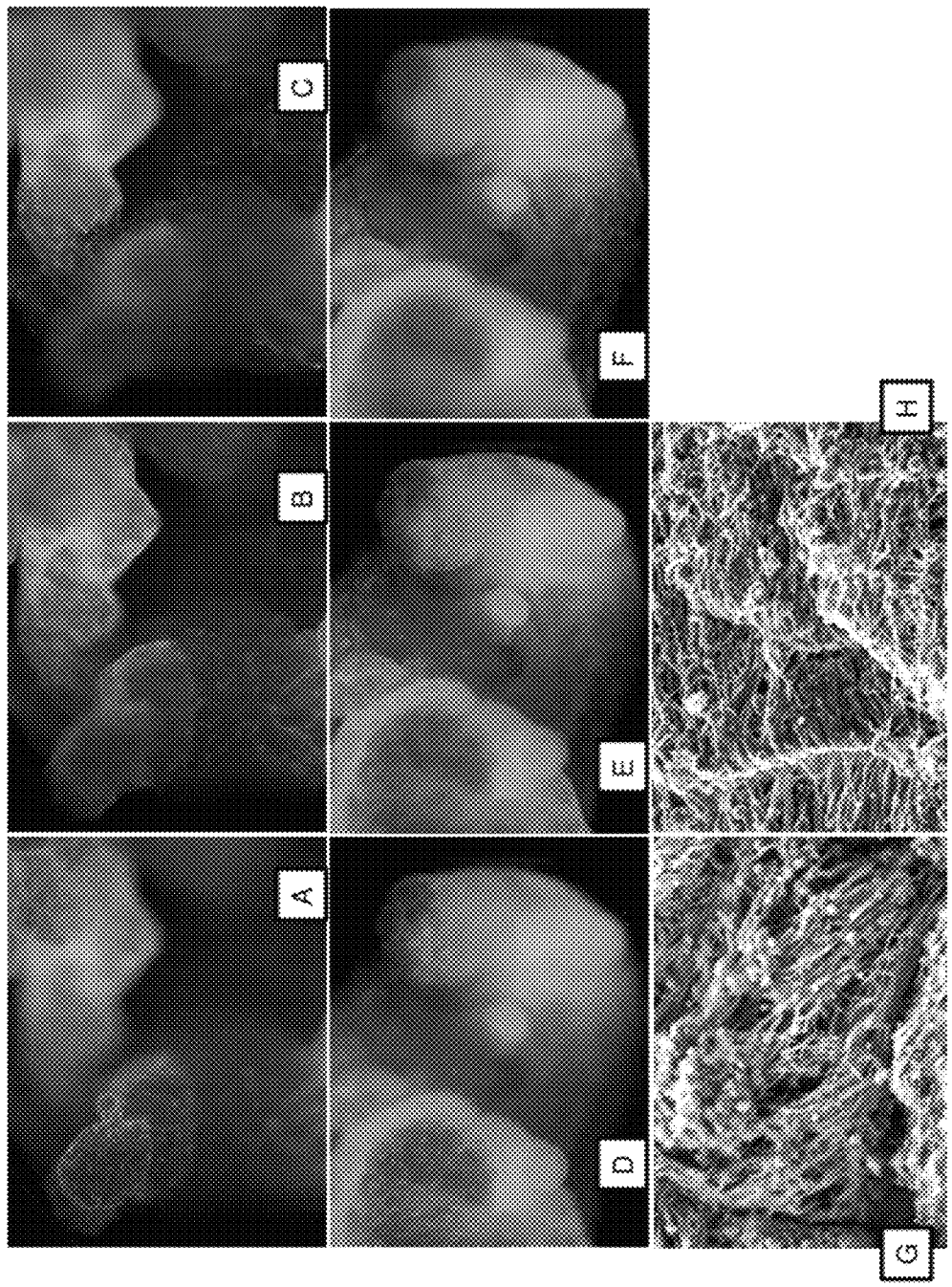

FIG. 32 comprising FIGS. 32A-32H depicts a series of images depicting fluorescence microscopy of constructs seeded with GFP-positive MSC's showing even population of the surface of untreated (FIGS. 32A-32C) and trypsin-treated matrices (FIGS. 32D-32F, 40×). Electron microscopy showed the presence of regular fibrils in untreated (FIG. 32G) and treated matrices (FIG. 32H, original magnification: 5000×).

Figure 33C:
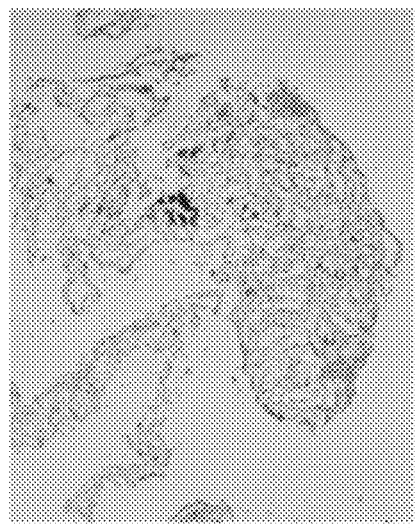
Figure 33B:
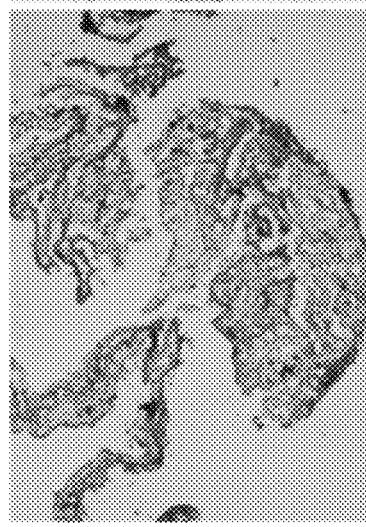
Figure 33A:
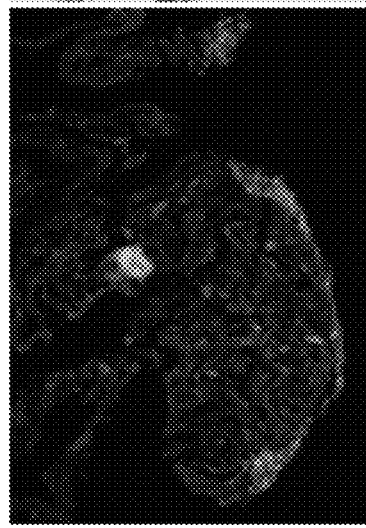
Figure 33F:
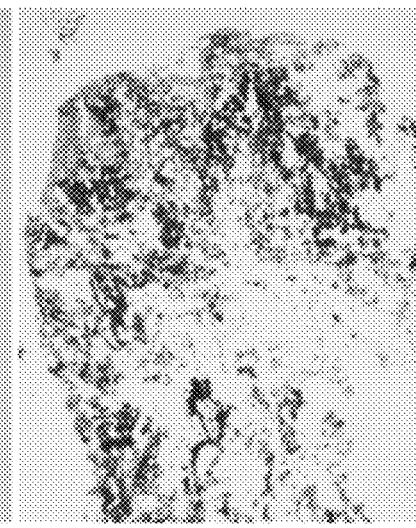
Figure 33E:
Figure 33D:
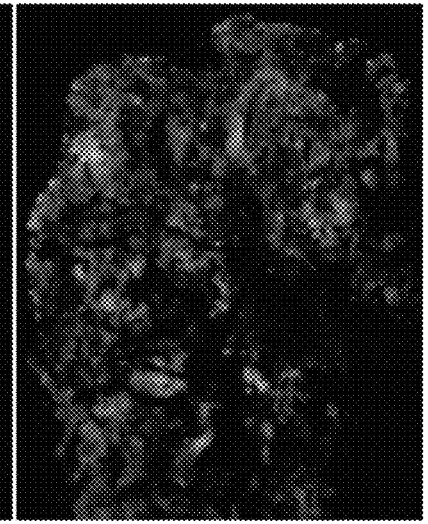

FIG. 33 comprising FIGS. 33A-33F, depicts a series of images depicting fluorescence imaging confirming presence of GFP-positive MSC's after 17 days of co-culture on untreated (FIG. 33A) or trypsin-treated matrices (FIG. 33D). Alkaline phosphatase (ALP) staining of constructs revealed ALP activity on the matrices (FIG. 33B and FIG. 33E) when compared to non-stained controls (FIG. 33C and FIG. 33F). Note the higher density of the trypsin-treated samples (FIG. 33D-FIG. 33F) when compared to the untreated samples (FIG. 33A-FIG. 33C, original magnification: 100×).

Figure 34:
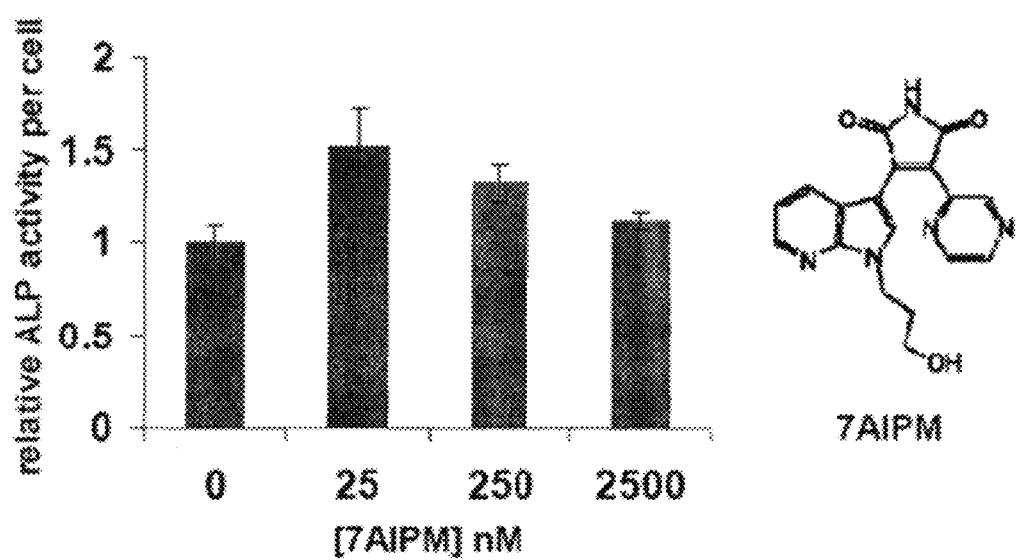

FIG. 34 is a chart depicting the influence of the Wnt modulator 7AIPM on osteogenic differentiation was examined by treating monolayers of MSC's with osteogenic medium containing increasing doses of the compound or vehicle. After four days, ALP activity and cell numbers were measured. A typical biphasic dose dependant effect was observed.

FIG. 35 comprising FIGS. 35A and 35B is a series of images depicting the gene ontology categorization of up-regulated genes in GW9662- and BIO-treated hMSCs.

FIG. 36 is a chart summarizing the differential expression of collagens and extracellular matrix components in hMSCs following treatment with GW9662 or BIO.

FIG. 37 is a chart depicting gene ontology categorization of down-regulated genes in GW9662- and BIO-treated hMSCs.

FIG. 38 is a chart depicting gene ontology categorization of up-regulated genes in BIO-treated hMSCs.

FIG. 39 is a chart depicting inflammatory cytokine expression in hMSCs treated with GW9662 or BIO;

FIG. 40 is a chart depicting confirmation of GW9662 microarray data by ELISA; and FIG. 41 is a chart depicting cell counts from lesioned calvaria after 59 days of treatment.

DETAILED DESCRIPTION

Although making and using various embodiments are discussed in detail below, it should be appreciated that as described herein are provided many inventive concepts that may be embodied in a wide variety of contexts. Embodiments discussed herein are merely representative and do not limit the scope of the invention.

Tissue repair remains costly and with many tissue repair may often fail. Failure may require the use of a synthetic implant that, too, may fail if not properly stabilized or is not accompanied by adequate healing or cellular and tissue responses. Such failure is, then, often permanent and can be debilitating. Rapid and reliable healing after repair should prevent complications and a need to perform further reconstruction of the tissue.

In certain tissue, such as bone, large defects may be bridged by grafting autologous bone (e.g., bone that is explanted from elsewhere and implanted at the injured site). While effective, autologous bone is very limited and requires an additional surgery combined with additional surgical complications. Tissue substitutes have been used to replace autologous tissue (e.g., synthetic material or decellularized tissue or bone). Unfortunately, these substitutes offer additional complications, such as poor cell adhesion, immunological rejection, and the inability to be as conductive (or conductive at all) as compared with the original tissue. Tissue substitutes are also often unable to support further and necessary cellular processes, such as angiogenesis, proliferation, and adequate cell nutrition. In addition, tissue substitutes are seldom contiguous with the host tissue. Moreover, long term exposure to foreign materials often cause complications associated with the foreign material in addition to deterioration of the foreign substitute itself. In short, many tissue substitutes remain incompatible over time. There is therefore, a need for safer and more biologically compatible bone repair alternatives, as are described herein.

There also remains a need for providing biologically compatible (biocompatible) tissue substitutes or implants that interact with surrounding tissue, achieve suitable homeostasis with the host tissue in a short period of time, and offer suitable support. This is particularly important for substitutes used with bone, fibrous or cartilaginous tissue repair.

Described herein is a biocompatible tissue substitute that meets requirements identified above.

Figure 6:
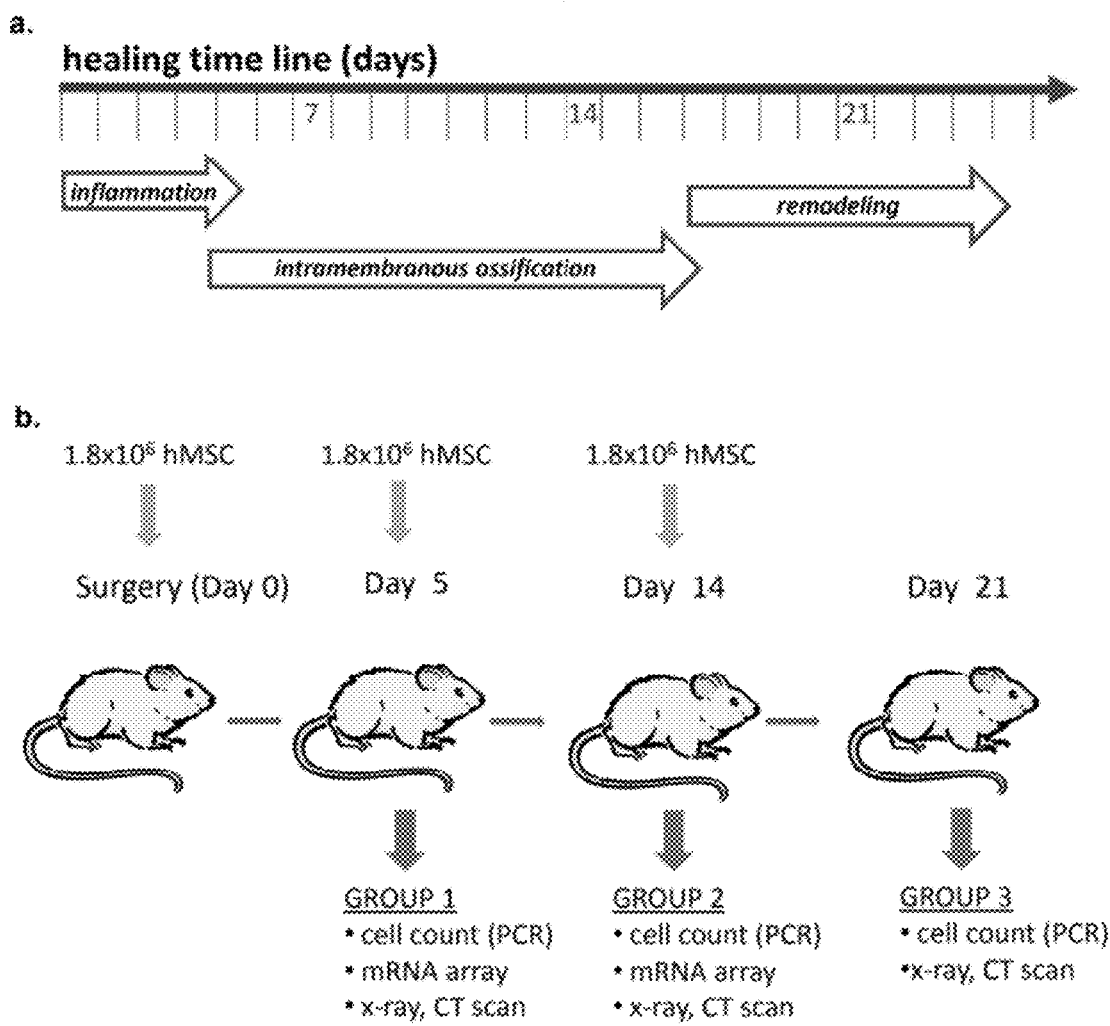
FIG. 6A illustrates a representative timeline for healing of bone.
FIG. 6B depicts a representative outline for a method described herein.

Human mesenchymal stem cells (MSCs) from bone marrow are disclosed in which regulation of adipogenesis is inhibited. In one form, the inhibition is through inhibition of peroxisome proliferator-activated receptor-γ (PPARγ). A suitable inhibitor of this receptor is 2-chloro-5-nitro-N-phenyl-benzamide or GW9662. Inhibition of PPARγ enhances osteogenic expression of hMSCs. The inhibition of PPARγ, allows Wnt signaling and promotion of osteogenic gene expression. Thus, with inhibition of the receptor in MSCs, osteogenic differentiation arises. With the addition of osteogenic additives, said pluripotent stem cells resemble osteoblast progenitor cells capable of mineralizing and secreting a bone tissue type extracellular matrix. As described, when MSCs were treated with an inhibitor of PPARγ, GW9662, and applied to a bone defect (i.e., calvaria bone defect) there was a 2-3 fold improvement in healing as compared with controls having untreated bone defects. With only about 60% of the lesion healing after 50 days of repeated cell administration, the addition of treated MSCs appear to be most beneficial at one or more specific stages of healing. FIG. 6A shows representatively, a timeline for healing of bone over a 3½ week period, which includes an inflammatory phase, a regenerative phase and a remodeling phase.

Described further herein are materials and methods for improving and/or accelerating tissue healing, such as the healing of bone and, particularly, the ability of said materials and methods to heal tissue at a preferred period of time during tissue healing.

For example, as further described herein, tissue repair capacity of MSCs as described are extended and the enhancement extends the overall healing phase in bone, particularly in the so-called rapid osteogenic phase that occurs after resolution of inflammation.

Generally, tissue repair capacity of MSCs in non-treated bone is less at later stages, including the later regenerative and remodeling phases as signals are lost and MSC-mediated healing (that of MSCs not treated as described herein) is disrupted because the cells are no longer retained at the site of healing. To extend healing, as described herein is a process for retaining MSCs at the lesion site as well as materials that include MSCs and a mixture having MSC-derived extracellular matrix (ECM) components. The ECM components include heterotypic collagen fibrils (distinct from steady-state bone tissue because it also includes additional collagens associated with developing or regenerating bone). It was found that co-administering MSCs with the ECM mixture to a site of tissue injury, such as bone tissue, in addition to pretreating the MSCs with a PPARγ inhibitor provided a support for the pretreated MSCs; the pretreated MSCs were retained at the site of injury well into the remodeling phase. The methods and materials described herein provided reproducible repair and healing of the tissue. Moreover, repair and healing of the tissue at the defect site was complete. Accordingly, described herein are also composites that include the MSC-derived ECM mixture and pretreated MSCs (pretreated with a PPARγ inhibitor) for substantially and reproducibly improving repair of tissue, such as bone, cartilaginous and fibrous tissue.

Figure 1:
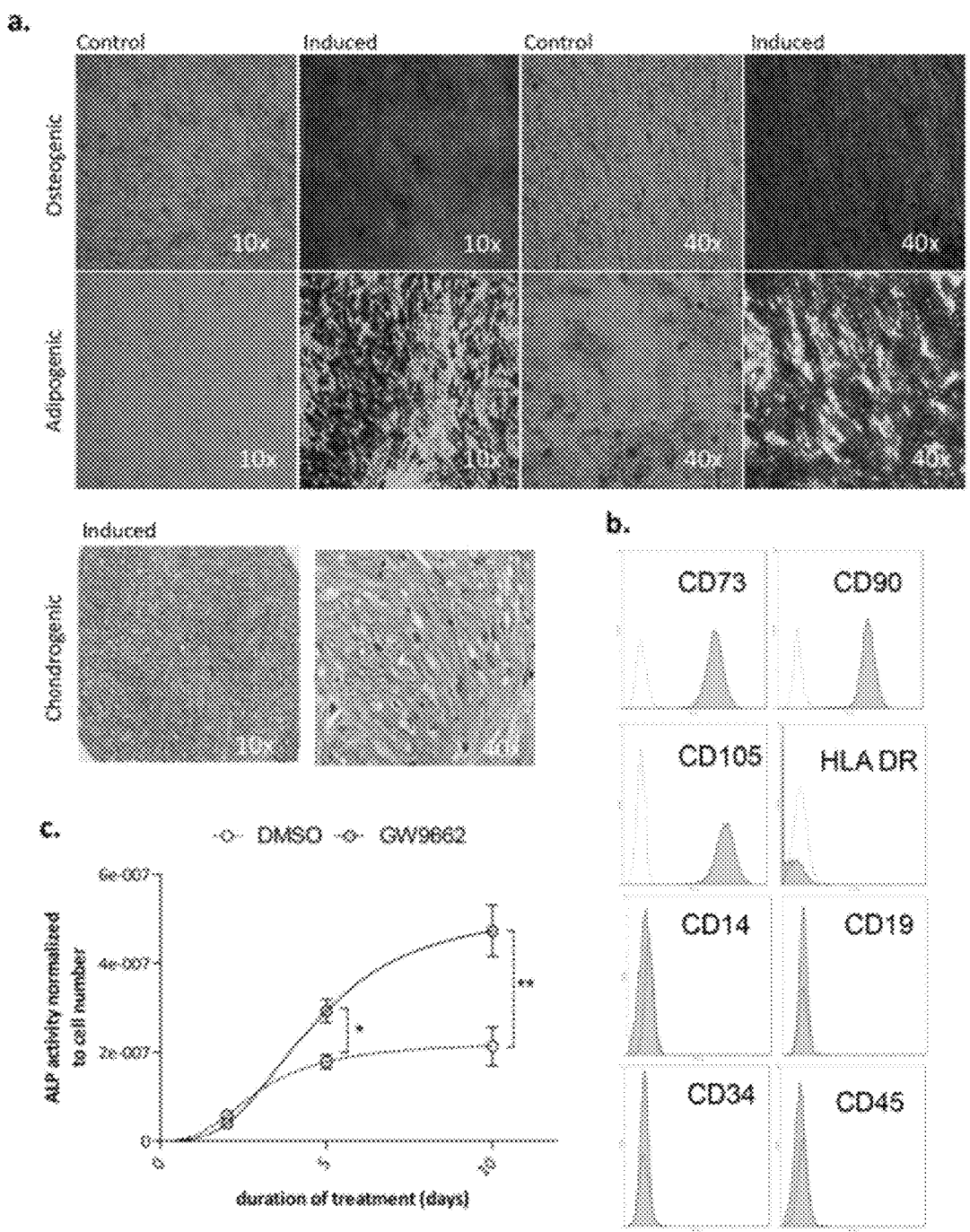
FIG. 1A depicts representative MSC differentiation into different cell types as described herein, wherein top row (low power, left and high power, right) shows contrast micrographs of osteogenic cultures stained for calcium with Alizarin Red S, middle row (low power, left and high power, right) shows adipogenic cultures stained for lipid vacuoles with oil red O and bottom row (low power, left and high power, right) shows micrographs of chondrocytes stained with toludine blue (purple)
FIG. 1B depicts a representative immunophenotypic analyses as described herein.
FIG. 1C depicts representative alkaline phosphatase (ALP) activity of hMSCs described herein after culturing in osteogenic media in the presence or absence of 10 mM GW9662.

The MSCs were initially analyzed and identified using standard in vitro assays of differentiation and flow cytometry. The MSC were found to exhibit the appropriate immunophenotype and capable of differentiation into osteoblasts, adipocytes and chondrocytes in vitro (FIG. 1A, B, FIG. 7) in accordance with standard procedures for evaluating this cell type. With pretreatment via inhibition of PPARγ (using, e.g., GW9662 in suitable media containing suitable osteogenic supplementation described elsewhere), alkaline phosphatase (ALP) activity was increased (FIG. 1C), which established osteogenic differentiation of the MSC, such that the cells were akin to osteogenic progenitor cells. In one example, human MSCs (hMSC) were prepared from 2 mL posterior iliac crest bone marrow aspirates. Cells were cultured according to standard conditions (37° C., 5% (v/v) $CO_2$) in complete culture medium (CCM), consisting of alpha minimal essential medium (alpha-MEM) containing 20% (v/v) fetal bovine serum (FBS), 2 mM L-glutamine, 100 units $ml^{-1}$ penicillin and 100 μg $ml^{-1}$ streptomycin. Media were changed every 48 hr. For each passage, cells were seeded at about 100 $cm^{-2}$. Cells were then recovered by trypsinization followed by cryopreservation in alpha-MEM containing 50% (v/v) FBS and 5% (v/v) dimethyl sulphoxide in the vapour of liquid nitrogen. Passage 1 cells were used in lentiviral labeling experiments and passage 3 or 4 cells were used in all other experiments. Phase contrast and fluorescent microscopy of live cultures was performed using an inverted microscope fitted with a digital camera.

Further description regarding analysis of and pre-treatment of hMSC has been described in co-pending patent application Ser. No. 12/730,022, herein incorporated by reference in its entirety.

An in vivo model for tissue healing was employed using mice subjected to a calvarial defect. In general, after fracture of long bones, there is rapid reorganization of the tissue architecture with initiation of inflammation. Shortly after, angiogenesis is initiated, feeding the lesion with nutrients and necessary cytokines. Thereafter, simultaneous processes of intramembranous ossification (IO) and endochondral ossification occur (EO). IO occurs at the periosteum, where mesenchymal progenitors differentiate directly to osteoblasts. This process involves the prompt deposition of a bony "hard callus" adjacent to cortical bone, but the process is generally attenuated after two weeks resulting in a relatively low volume of new tissue and limited range in terms of gap closure. EO is initiated by rapid expansion of mesenchymal cells adjacent to the fracture that differentiate into chondrocytes, forming a cartilaginous "soft callus" rich in type II collagen, and over a few weeks the callus is calcified to bone. When cultured MSCs are induced to generate a mineralized matrix, they do so by a process that resembles IO in that the cells differentiate directly to mineralizing osteoblast-like cells in the absence of an intermediate chondrocytic phase. A model of rodent calvarial healing that occurs exclusively by IO was useful herein to examine potential stage-wise effects of hMSC-mediated osteo-repair. This model also recapitulates the inflammatory, rapid osteogenic and remodeling phases without a chondrogenic stage characteristic of EO.

Figure 2:
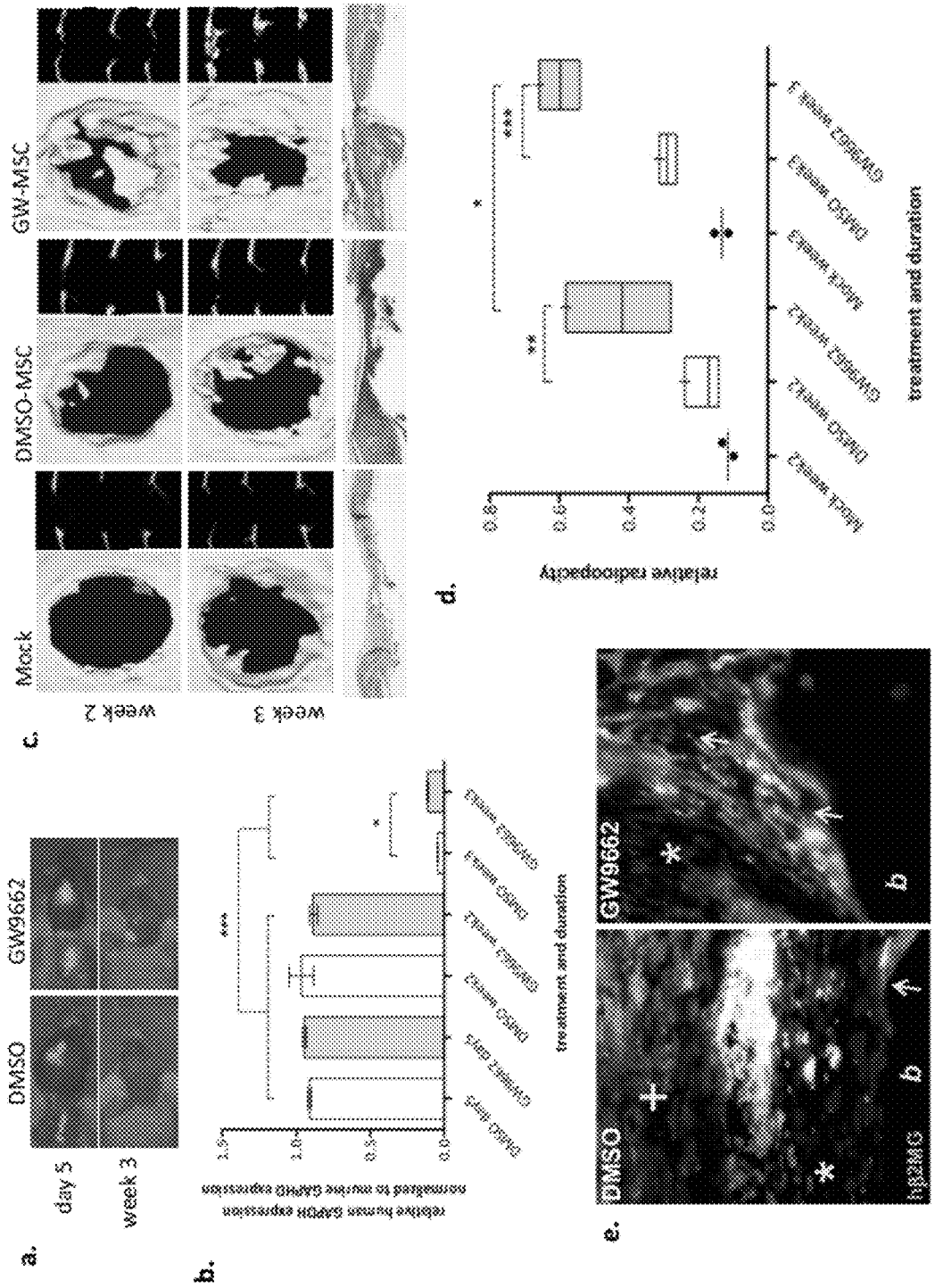
FIG. 2A shows a representative image of hMSCs detected one week (top) and 3 weeks (bottom) after reconstruction as described herein, wherein one million green fluorescent protein (GFP) positive hMSCs were pretreated by osteogenically culturing with 10 µM GW9662 or vehicle and then administered to calvarial defects at time zero and again 1 week and 2 weeks post surgery.
FIG. 2B shows a representative cell type expression of a protein after reconstruction for the procedure described with FIG. 2A, wherein relative calvarial human GAPDH expression is shown as normalized to murine GAPDH expression (n=4)
FIG. 2C shows representative cell and tissue changes after reconstruction as microCT of lesions in crania (left) and axial reconstructions (right) at 2 and 3 weeks for the procedure described with FIG. 2A.
FIG. 2D shows a representative relative radioopacity of tissue after reconstruction as described with FIG. 2A, wherein radio-opacity was measured by digital radiology followed by densitometry and healing indices were the ratio of lesioned to contra-lateral radio-opacity where complete healing is designated 1 and air is designated zero and bar plots represent range and mean (n=4) while mock assays (n=2) are shown independently with the median.
FIG. 2E shows a representative immunostaining of cell types after reconstruction as described herein, wherein the magnification, 40×, of calvaria shows human β2-microglobulin (green) from week 2 with a greater number of GW-hMSCs (see arrows, right image) engrafting adjacent to bone tissue (b) when compared with controls (left image), in which a murine cell layer (*) separated the main population of hMSCs (+) from the bone.
Figure 8:
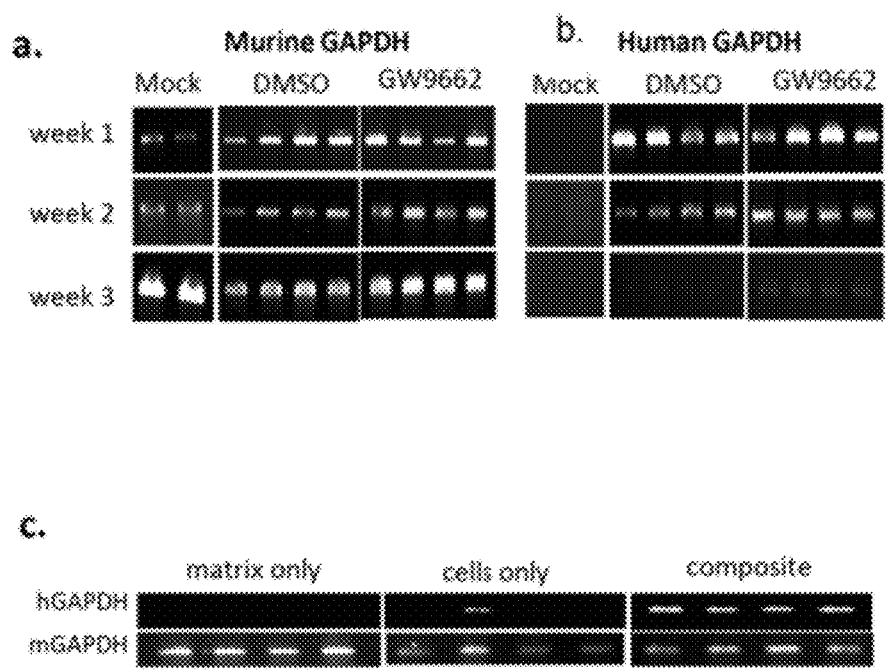
FIGS. 8A-8C depict representative images of mRNA expression after repair and reconstruction as described herein, wherein RT-PCR assays of human and murine GAPDH transcription were performed on explanted calvaria of FIG. 2A (FIG. 8A, 8B) and FIG. 5B (FIG. 8C)
Figure 9:
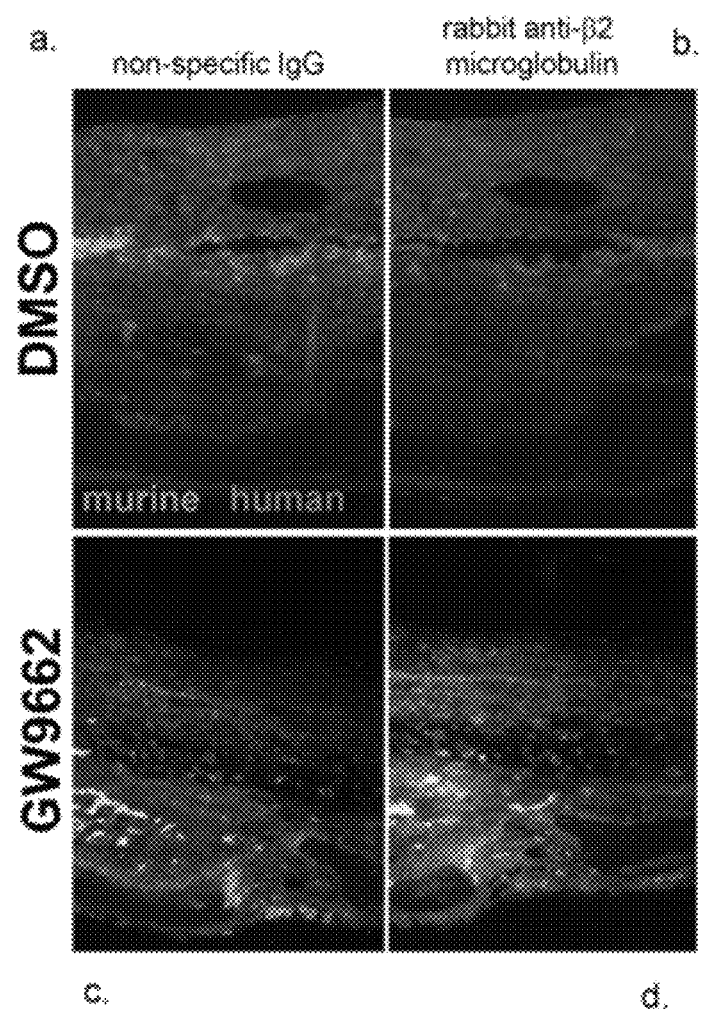
FIGS. 9A-9D depict representative images of immunostained tissue after treatment as performed with FIG. 2E, showing micrographs of immunostained human β-2 microglobulin engrafted in calvarial bones after 2 weeks of healing (right) and immunoglobulin controls (left)

Peri-surgical administration of either pre-treated hMSCs or non-treated (control) hMSCs were followed by weekly local injections as outlined in FIG. 6B. Groups of mice were then euthanized at 5 days, 14 days and 21 days post surgery. The 5-day period corresponded with and approximated the resolution of inflammation, in which closing of the lesion had not commenced but cells were clearly detectable at the bone defect and at the skin incision by fluorescent imaging (FIG. 2A upper images). RNA was recovered for analysis and quantitative RT-PCR, which indicated that approximately 200,000 hMSCs (11% of the original dose) were present at the lesion site (FIG. 2B, FIG. 8). At week 2, cell engraftment continued and the calvarial lesions had initiated healing as determined by densitometric radiography and microCT (µCT) scanning (FIG. 2C upper images, FIG. 2D). As expected, administration of PPARγ-inhibitor treated hMSCs (or GW-hMSCs) significantly improved the rate of healing as compared with control (vehicle or DMSO) treated hMSCs (FIGS. 2C, D). After 3 weeks, approximately 60% of the lesion had healed in the group receiving GW-hMSCs compared to approximately 30% in the controls. When cell engraftment was assayed at week 3 however, a drastic reduction in cell number was observed for both the control and GW-hMSC groups with about 0.5% and 1% of the original dose engrafted, respectively (FIG. 2B, FIG. 8). Therefore, conditions maintaining viability and/or cell-retention at the lesion site over the prior 2 weeks were reduced. Although overall engraftment at week 3 was substantially lower, significantly more GW-hMSCs had remained at the lesion compared with the control-treated cells. Immunocytochemistry of the explanted calvaria from week 2 specimens revealed that there was a split distribution of hMSCs at the lesion site with populations of cells remaining above the lesion (labeled "+" in FIG. 2E) and also cells adjacent to the bone (FIG. 9; arrowed in FIG. 2E). The two populations were separated by an approximately 10-cell thick layer of murine fibroblast-like cells (labeled "*" in FIG. 2E). Calvarial explants that received GW-hMSCs had substantially more cells interacting directly with the bone compared with sporadic bone-surface distribution in the controls (FIG. 2E, arrowed areas). GW-hMSCs had a greater affinity for bone tissue and could be contributing directly to bone repair.

For immunophenotyping, MSCs were recovered by brief trypsinization and incubated with one or more fluorophore-tagged antibodies or respective isotype controls for 30 min in a phosphate-buffered saline (PBS) containing 2% (v/v) FBS. After about three washes, a minimum of 20,000 cells were analyzed on a flow cytometer and data processed using machine-compatible software. Antibodies against the following cell surface antigens were used, including CD11b (clone BEAR1), CD14 (RM052), CD19 (J3-119), CD29 (MAR4), CD34 (581), CD36 (FA6.152), CD44 (G44-26), CD45 (J.33), CD49a (SR84), CD49b (Gi9), CD49c (C3 II.1), CD49e (IIA1), CD51 (23C6), CD73 (AD2), CD79a (HM47), CD90 (Thy-1/310), CD105 (IG2), CD146 (TEA1/34), CD166 (3A6), HLA-A,B,C (G46-2.6), HLA-DP,DQ, DR (Tu39).

For mineralizing osteogenic differentiation, confluent monolayers of hMSCs were incubated in CCM supplemented with $10^{-8}$ M dexamethasone, 50 $\mu mL^{-1}$ ascorbic acid and 5 mM β-glycerol phosphate for 21 days with changes every 2 days. The monolayers were then stained with 40 mM Alizarin Red S pH 4.0 for 30 min and washed 4 times with distilled water. Micrographs were taken using an inverted microscope fitted with a digital camera.

For non-mineralizing osteogenic differentiation, hMSCs were plated in 12-well plates at 100 cells $cm^{-2}$. Upon reaching about 70% confluency, the media was changed to osteogenic base media (OBM) containing 50 µg $mL^{-1}$ ascorbic acid and 5 mM β-glycerol phosphate and either GW9662 or DMSO. Media was changed every 2 days for 8-10 days following measurement of ALP activity. For this purpose, the monolayer was washed with PBS and then with ALP reaction buffer (100 mM Tris-HCl, pH 9, containing 100 mM KCl and 1 mM $MgCl_2$). One half mL of ALP buffer then 0.5 mL p-nitrophenol phosphate (PNPP) was rapidly added to the wells. ALP activity was measured as the rate of PNPP conversion to p-nitrophenolate by monitoring the absorbance at 405 nm every 30 seconds for 9 minutes using a plate reader. The rates were normalized against cell number and statistically analyzed using one-way analysis of variance (ANOVA) and Tukey post test for multiple comparisons or by Student's t-test, for single, unrelated comparisons.

For adipogenic differentiation, confluent monolayers of hMSCs were incubated in CCM supplemented with 0.5 µM dexamethasone, $5 \times 10^{-8}$ M isobutylmethylxanthine, and $5 \times 10^{-7}$ M indomethacin. Media were changed every 2 days. After 21 days, the adipogenic cultures were fixed in 10% (v/v) formalin for 15 min and stained with fresh 0.5% (w/v) oil red-O solution in 30% (v/v) isopropanol in phosphate buffered saline (PBS) for 20 min. The dishes were washed with excess PBS and visualized using an inverted microscope.

For chondrogenic differentiation, about 50,000 cells were pelleted. Briefly, pellets were incubated in high glucose DMEM containing $10^{-7}$ M dexamethasone, 50 µg $mL^{-1}$ ascorbate-2-phosphate, 40 µg $mL^{-1}$ proline, 100 µg $mL^{-1}$ pyruvate and 2×ITS plus premix with media changes every 3 days. After 21 days of differentiation, the pellets were washed in PBS and fixed in 4% (v/v) paraformaldehyde, embedded in paraffin, sectioned, and then stained with toluidine blue to visualize sulphated proteoglycans and chondrocyte lacunae.

In some cases, hMSCs were sparsely populated and could be recovered as a single cell suspension, permitting a rapid quantification protocol. In cases where monolayers were dense, associated with high levels of extracellular matrix and could not be recovered as a single cell suspension, an extended processing protocol was employed. For the rapid protocol, hMSCs were recovered by trypsinisation, pelleted by centrifugation and resuspended in hMSC lysis buffer consisting of PBS containing 1 mM $MgCl_2$ and 0.1 (w/v) % Triton X100. The lysate was mixed by passing multiple times through a 200 µL micropipette tip and transferred to an equal volume of cell proliferation assay buffer containing a dye for measuring cell proliferation (e.g., CyQuant®, a trademark of Molecular Probes, Inc., Eugene, Oreg.). One hundred-µL aliquots of the suspension were transferred to wells of an opaque black micro-titer plate and read fluorometrically with excitation/emission set to 485/520 nm. Fluorescence intensity was compared with a linear set of known standards to ascertain cell numbers. For the extended protocol, plates harboring monolayers were incubated in a humidified chamber in the presence of the hMSC lysis buffer containing 1 unit per mL of EcoRI and HindIII at 37° C. with rocking. After 16 hours, lysates were transferred to microcentrifuge tubes, pelleted at 8,000 G for 15 minutes and aliquots of supernatant containing a clarified solution of DNA fragments were quantified as in the rapid protocol described above. Cell standards processed in the same manner were used to generate standard curves.

For treatment of hMSC, GFP-positive, passage 3 or 4 hMSCs were plated at 100 cm$^2$, then cultured in CCM until 80% confluency was achieved (approximately 10-15,000 cells per cm$^2$). The GFP positive cells harbor a lentivirally introduced gene expressing the protein. To osteogenically enhance these hMSCs, 25 mL OBM media was added containing 10 µM GW9662 in DMSO. GW9662 was added freshly from a frozen 1000× stock in DMSO. Controls received DMSO only. Media was changes every 2 days for 8 days and cells were recovered on the day of surgery by trypsinization, washed in PBS and suspended in Hank's buffered salt solution containing 2% (v/v) FBS on ice until administration. At the point of administration, cells were pelleted by short centrifugation at 1000 G, suspended in cold 45 µL human plasma, added the same volume of cold 2× thromboplastin C and immediately pipetted onto the lesion. Subsequent doses were prepared in the same manner and injected under the scalp while mice were anesthetized.

In brief, the calvarial lesion model was performed with two month old female Nu/J mice. Under anesthesia, and with whole body warming at 34° C., a 4 mm diameter circular lesion in the frontal calvarial bone was generated 1-2 mm from the sagittal and coronal sutures using a 3 mm osteotomy burr. In each case, the depth and extent of the lesion was checked by gentle probing around the circumference of the cut so as to ensure the hole was the entire depth of the calvarial bone. After irrigation with PBS, cells (untreated or treated as described herein) were administered. Once there was clotting, the scalp was sutured closed and mice were allowed to recover from anesthesia with additional warming and oxygen for 2-3 minutes. For 2 days post surgery, saline and an analgesia was administered subcutaneously. When cells were administered with the addition of an ECM mixture, ECM mixture was placed in the lesion and cells were over-layed.

For discussions regarding bone extractions and processing, mice were humanely processed in accordance with Institutional Animal Care and Use Committee procedures. In brief, animals were euthanized and cranial bones were cut away using a rotary tool fitted with a 10 mm diameter diamond cutting wheel. Top of the skull was gently removed, washed in PBS, and cleared of excess connective tissue. For RNA extractions, the tissue was flash-frozen in liquid nitrogen and for histology, calvaria were fixed in 10% (v/v neutral buffered formalin).

For RNA extraction, total RNA was extracted from the cranial bones using a suitable total RNA isolation kit. Bones were incubated in RNA extraction buffer at ambient temperature for 4 hr and processed in accordance with the protocol. Yields were in the range of 20-50 µg per sample and 260/280 nm ratios ranged between 1.7-1.9. The RNA recovery from mock specimens was generally low (approximately 5 µg) due to the amount of live tissue associated with calvarial bones, but sufficient RNA was recovered for control PCR reactions. In consideration of the yield discrepancy between samples that received cells and the mock controls 75-90% of the RNA is likely to be of hMSC origin.

For microarray assays, about 2.0 µg of pooled RNA from a specimen used for assaying. Briefly, double-stranded cDNA was synthesized using a suitable one-cycle cDNA synthesis kit and cleaned. Biotin-labeled cRNA was synthesized using a genechip labeling kit, cleaned, and quantified spectrophotometrically. Generally, 20 µg of biotin-labeled cRNA was hybridized to each suitable hybridization array (e.g., GeneChip Human Genome U133 Plus 2.0 array from Affymetrix, Inc.). After 16 hours of hybridization, the arrays were washed and stained using a suitable genechip hybridization sash and stain kit. The arrays were then scanned using the genechip scanner. Appropriate software was used to run the instruments and perform quality control measurements. Control and treated arrays were compared with the assumption that murine cross-hybridization would be constant throughout the samples and thus be subtracted from the analysis. Transcipts of interest generated from the array data were confirmed using conventional, species-specific real time PCR (RT-PCR).

For standard and real time quantitative reverse transcription, generally one-µg of total RNA was used to synthesize cDNA. For conventional PCR, 0.5 µg of cDNA was amplified in a 25 µL reaction using PCR-master mix on a standard thermocycler. Amplified DNA was visualized by agarose gel electrophoresis. For quantitative RT-PCR (qRT-PCR), 0.5 µg of cDNA was amplified in a 25 µL reaction containing a cyanine dye, such as SYBR-green, and a suitable PCR master mix on a thermocycler fitted with a real time module. GAPDH data were calculated using a 2-delta CT method and presented as a ratio of murine to human signal. Data were statistically analyzed by one way analysis of variance (ANOVA) on arcsine transformed data and post-analysed by Tukey's method using GraphPad Prism. Collagen expression data were calculated using the 2-delta CT method using human GAPDH as a reference. Some PCR conditions and primers are provided in FIG. 12. Data was statistically analyzed using one-sided ANOVA.

Healing of calvaria was quantified using a 2D densitometry based on the transmittance of x-rays through the lesion to a phosphorimager plate as previously described by others. Volume measurements were taken at the lesion and contralateral side and the fraction of healing was calculated for each case. One-sided ANOVA followed by Tukey post test was performed to determine significance of results.

Micro computer aided tomography (µCT) briefly included scanning of identical calvaria over 360° using a 50 kV beam with a camera resolution of 12 µm. Images were captured every 0.4° with flat field correction and frame averaging enabled. Using mock specimens, grayscale ranges were calibrated over intact bone, partially formed bone and radiolucent tissue over a fixed linear range (corresponding to approximately −100 to +1000 Hounsfield units). Axial reconstructions were generated from the scans and quantified using a appropriate CT software. Once again, each reconstruction parameter was identical and performed over a fixed and linear intensity range in each case so as to reproducibly distinguish bone, partial bone and radiolucent tissue. In each case, ring artifact, smoothing, and beam hardening corrections were enabled. Three dimensional renderings for qualitative appraisal were generated using one or more volume software. Measurements of recovered matrix volume were performed using similar parameters, but the beam power was lowered to 30 kV.

For extracellular matrix (ECM) production, hMSC monolayers were treated for 8 days with GW9662 or control OBM media in the usual manner described previously. Mineralizing osteogenic media was then added for a further 10 days with changes every 2 days. Hereafter, all volumes refer to a single 150 cm² monolayer culture. Monolayers were washed in PBS and frozen at −80° C. to disrupt cell membranes, thawed to ambient temperature and scraped from the culture plate. Recovered cells and ECM were then pelleted by centrifugation (1,800 G) and suspended in 10 mL of lysis buffer consisting of PBS containing 0.1% (v/v) Triton X100, 1 mM $MgCl_2$, 10 µg $mL^{-1}$ DNAse I and 10 µg $mL^{-1}$ RNAseA. The lysis was allowed to proceed with incubation with shaking at 60 revolutions per minute for 4 hours h at 37° C. The lysis was allowed to proceed for a further 16 h in the presence of 0.125% (v/v) trypsin. The remaining ECM was then recovered by centrifugation (1,800 G), washed twice in 20 mL $dH_2O$, twice in 15 mL chloroform, then twice more in deionized $H_2O$. Finally, ECM was rinsed in 15 mL acetone and allowed to air-dry.

For X-ray diffraction for matrix characterization, hMSC derived ECM was prepared as above, then digested with 20 µg $mL^{-1}$ proteinase K at 50° C. for 24 h in 50 mM TrisHCl pH8.0. The remaining precipitate was washed 3 times with excess deionized $H_2O$ and then freeze dried. X-ray diffraction analysis was carried out on the residue at the Department of Earth and Environmental Sciences, University of New Orleans, La. in the standard way using an X-ray diffractometer.

For scanning electron microscopy (SEM), samples were washed through an escalating series of ethanol concentrations (50%-100% (v/v)) and air dried. A thin layer of carbon (~10 nm) was then coated onto samples by a vacuum evaporator and the samples were observed Calcium levels in matrices described were determined using an acid hydrolysis ArsenazoIII method previously described by others. Briefly, matrices were heated in 6N HCl until entirely dissolved, then neutralized to pH5.0-5.5 using a predetermined amount of 2.5 M TrisHCl adjusted to pH 10.0. Colorimetric determination of calcium was performed by addition of Arsenazo III compound and monitoring the change in absorbance at 595 nm using a plate reader.

ECM samples recovered from 170 cm² of monolayer were dissolved in 1 mL of sequencing grade 6 N HCl by incubation at 80° C. in a sealed 15 mL polypropylene tube for 4 hour or until complete. Amino acid composition was performed by the Protein Biochemistry Laboratory at Texas A & M University Department of Biochemistry and Biophysics, College Station, Tex. Briefly, the samples were completely hydrolyzed under vacuum at 105-110° C. for 16-24 hours. Free amino acids were derivatized with o-phthalaldehyde and 9-fluoromethyl-chloroformate prior to separation and quantitation.

Immunoblotting was performed in the usual manner using suitable reagents. Antibodies used included mouse anti-GAPDH, mouse anti-β-actin, goat anti-type I collagen, goat anti-mouse IgG, rabbit anti-goat IgG.

For histology, immediately following euthanasia, calvaria were harvested and placed in 10% neutral buffered formalin (VRW International) for 24 hours at room temperature, after which it was washed in PBS and stored in Carson's fixative (1.86% (w/v) sodium phosphate monobasic, 0.42% (w/v) sodium hydroxide, 10% (v/v) formaldehyde) at 4° C. until decalcifaction. Calvarial tissue were washed again with fresh PBS and decalcified in 1M dibasic EDTA at pH 8.0, with changes every two days until radioluscency was achieved. Processing and embedding of tissue involved manual dehydration through a ascending gradient of alcohols, clearing with suitable clearing agent and infiltration with paraffin wax type 6. Paraffin-embedded calvaria were cut in 15 micron thick sections, and then floated onto suitable microscope slides for hematoxylin and eosin (H&E) staining and immunohistology.

For staining, sections were baked onto slides at 60° C. for an 1 hour before being deparaffinized with citrus clearing agent, rehydrated to distilled water, stained with hematoxylin solution, rinsed with distilled water, counterstained with eosin Y, 1% (w/v) solution in water, dehydrated, and cleared. A mounting solution with toluene was used as a mounting medium to cover slip.

For immunocytochemistry, sections were deparaffinized and blocked for 16 hour in PBS containing 2% (v/v) donkey serum and 0.1% (v/v) Triton X100. Human cells were stained with a rabbit-anti-human β2-microglobulin antibody at 1 in 100 dilution in block buffer over 48 hour at 4° C. Controls were performed with non-specific rabbit IgG. Bound antibody was detected by donkey-anti-rabbit IgG conjugated to a dye that emits at about 488 nm (one that emits similar to fluorescein isothiocyanate). Sections were mounted with 4',6-diamidino-2-phenylindole containing mounting media and visualized with an upright fluorescent microscope running digital imaging software. Due to the high incidence of autofluorescence in bone tissue, true green fluorescence was detected using a 475-490/540-565 nm dual-band filter.

All statistical tests and data plotting were performed using a suitable program.

To gain more insight into the superior healing potential of GW-hMSCs and also what might be accounting for their extended engraftment, microarray analyses on the RNA extracted from the calvarial tissue recovered after day 5 and 14 were performed (FIGS. 11, 12). Because RNA yields from calvaria that received hMSCs were 4-8 fold higher than controls that received no cells, it appeared that most of the RNA was human in origin, thus suggesting that background cross-hybridization from murine transcripts would be low. Microarray data from day 5 and 14 were similar, sharing most of the differentially expressed genes and although the lists were surprisingly short, there was a striking prevalence of up-regulated transcripts coding for ECM proteins, particularly collagens. Primarily, up-regulation of collagens XI, XII, XV and XXI by GW-hMSCs was detected in vivo. Given that this list represented the top collagens up-regulated in cultured GW-hMSCs as well, it was believed that the remaining collagens identified in the in vitro study performed by others would be detectable by a more specific and sensitive quantitative RT-PCR. When the RNA samples were analyzed in this manner, collagens I, III, V, VI, XI, XII, XIV, XV and XXI were found to be up-regulated by GW-hMSCs in vivo, as depicted in TABLE 1.

TABLE 1

Mesenchymal stem cell derived collagen transcripts as regulated by treatment after reconstruction.

| Collagen transcript | Microarray data | | | Chain designation | Week 1 Fold up | Week 2 Fold up |
|---|---|---|---|---|---|---|
| | Microarray probe and chain designation | Week 1 Fold up | Week 2 Fold up | | | |
| COL I | 217430_x_at (α1) | 3* | NM | α1 | 27.8 ± 19.5 | 8.2 ± 3.9 |
| | 202311_s_at (α1) | 2.25* | NM | | | |
| COL III | 232458_at (α1) | 2.25* | NM | α1 | 7.1 ± 1.03 | 3.08 ± 1.04 |
| COL V | 52255_s_at (α3) | 3.34* | NM | α1 | 13.53 ± 8.74 | 11.69 ± 6.23 |
| | 218975_at (α3) | 2.17* | NM | | | |
| COL VI | 212937_s_at (α1) | 3.23* | NM | α2 | 14.94 ± 10.5 | 3.24 ± 2.73 |
| | 212091_s_at (α1) | 3.22* | NM | | | |
| | 212940_at (α1) | 2.99* | NM | | | |
| | 209156_s_at (α2) | 2.71* | NM | | | |
| | 213290_at (α2) | 2.29* | NM | | | |
| COL XI | 37892_at (α1) | 3.75 | 4.16 | α1 | 24.73 ± 3.79 | 11.04 ± 8.42 |
| | 204320_at (α1) | 3.32 | 3.95 | | | |
| | 229271_x_at (α1) | 2.23 | 3.13 | | | |
| COL XII | 231766_s_at (α1) | 2.47 | ndet | α1 | 10.95 ± 6.18 | 4.82 ± 1.82 |
| | 225664_at (α1) | 2.37 | 2.07 | | | |
| COL XIV | 203477_at (α1) | 2.98 | ndet | α1 | 4.7 ± 2.3 | 2.17 ± 1.12 |
| COL XV | 203477_at (α1) | 2.98 | 3.00 | α1 | 11.8 ± 4.73 | 5.27 ± 1.79 |
| COL XXI | 208096_s_at (α1) | 4.63 | 4.1 | α1 | 6.99 ± 6.6 | 4.03 ± 1.82 |

In TABLE 1, (*) were those detected in vitro after 8 days, but not by in vivo microarrays. NM is not measured. ndet is measured but not detected. Units are mean fold-changes compared with DMSO (control) MSCs with standard deviations (n=4 animals). Statistical comparisons of week 1 and 2 data were performed by one-sided t-test on arcsine transformed data. PCR fold changes were derived using the delta-delta CT method normalized to the human GAPDH transcript.

In view of the above findings, increased secretion of particular collagen types at the lesion by GW-hMSCs during the healing process appeared to be responsible in part for their enhanced efficacy and the increased number of GW-hMSCs persisting at week 3. The notion that the collagens identified above are up-regulated during the rapid stage of calvarial bone repair was supported in part by meta-analysis of existing data submitted by others to the NCBI's Gene Expression Omnibus (GEO). These data, accessible through GEO Series accession number GSE20980, indicated that type V, VI, XII and XV collagen chains were robustly up-regulated at day 5 of calvarial repair when compared to the remodeling phase at day 21. This is further depicted in TABLE 2. Taken together, it appeared that hMSC-derived collagens may enhance repair of calvarial lesions by providing an osteogenic retention signal for both exogenous hMSCs and host-derived cells.

TABLE 2

Meta-analysis of tissue healing over time.

| Agilent accession number | Transcript | Intensity (day 5) | SD day 5 (n = 8) | Intensity (day 21) | SD day 21 (n = 6) | Day 5 vs day 21 p-value |
|---|---|---|---|---|---|---|
| A_44_P419137 | Col1a1 | 0.955396 | 0.16519 | 1.605216 | 0.41348 | 0.001538 up |
| A_44_P458851 | Col1a2 | 0.767368 | 0.154011 | 1.896181 | 0.45571 | $2.55E^{-05}$ up |
| A_44_P146518 | Col3a1 | 0.718811 | 0.144286 | 2.505413 | 0.295402 | $3.82E^{-09}$ up |
| A_43_P13273 | *Col5a1 | 2.141828 | 0.682257 | 0.211388 | 0.000183 | $5.73E^{-05}$ down |
| A_44_P392845 | *Col5a2 | 0.961477 | 0.17281 | 0.697207 | 0.333898 | $1.2E^{-06}$ down |
| A_44_P197290 | *Col5a3 | 2.038541 | 0.464403 | 0.285323 | 0.122854 | $5.73E^{-05}$ down |
| A_44_P349553 | *Col6a1 | 1.555223 | 0.281883 | 0.681838 | 0.227207 | $4.53E^{-05}$ down |
| A_44_P515888 | *Col6a2 | 2.090137 | 0.661577 | 0.702657 | 0.13942 | 0.0003 down |
| A_44_P243887 | Col6a3 | 1.391074 | 0.759111 | 0.735812 | 0.470026 | ns |
| A_44_P123636 | Col11a1 | 1.224911 | 0.794598 | 0.458349 | 0.34299 | ns |
| A_44_P272045 | Col11a1 | 1.784576 | 0.764435 | 2.340665 | 2.303095 | ns |
| A_44_P473153 | *Col12a1 | 2.354913 | 0.852047 | 0.695539 | 0.343796 | 0.00077 down |
| A_44_P171271 | Col14a1 | 1.121793 | 0.302666 | 1.234578 | 0.692541 | ns |
| A_44_P208699 | *Col15a1 | 2.380867 | 0.666232 | 0.554075 | 0.165146 | $5.32E^{-05}$ down |

Figure 3:
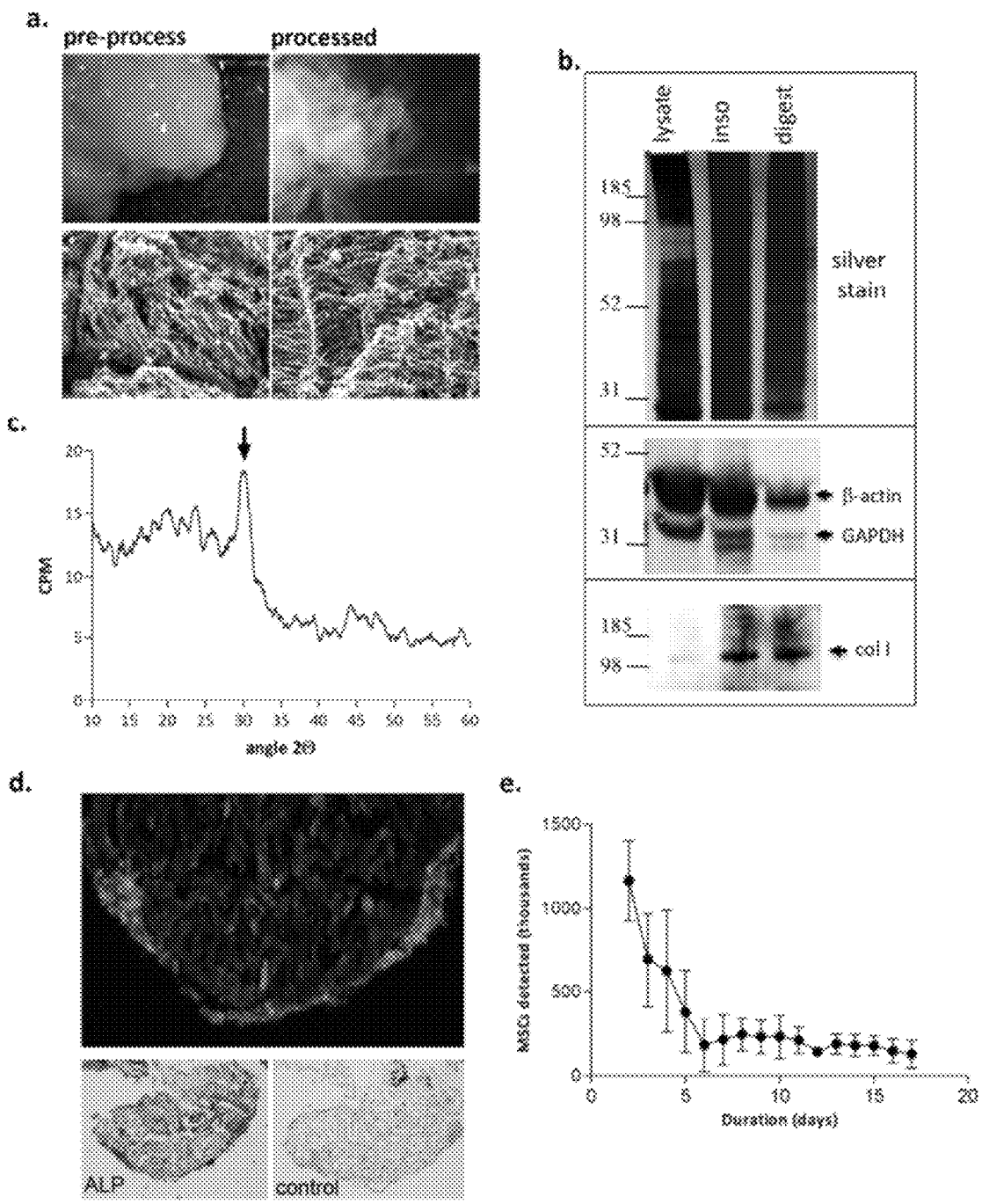
FIG. 3A depicts representative characterization of an ECM, as described, before and after processing as described herein, including decellularized insoluble components recovered from osteogenic cultures of MSCs, wherein the general appearance of unprocessed ECM (top left) and by electron micrograph (bottom left) with debris were associated with random orientation of fibrils as compared with enzymatically and solvent processed ECM as described (right panels) that were associated with fibrillar appearance (top right) and regularly-oriented, more defined fibrillar structure when visualized by electron microscopy (bottom right)
FIG. 3B depicts representative characterization of ECM, as described, before (left) after processing (right) as described herein, wherein immunoblotting demonstrated that processing depleted cellular proteins such as GAPDH and β-actin, but preserved cellular matrix proteins such as collagen type I.
FIG. 3C depicts a further characterization of ECM after processing as described herein, showing X-ray diffraction analysis of the inorganic component of the recovered ECM showing brushite as a major form of calcium phosphate.
FIG. 3D depicts additional characterization of ECM, obtained as described, after processing and then seeding with GFP expressing hMSCs showing the seeded cells (top) inhabited the external surface, mimicking a periosteal distribution and hMSCs exhibited high levels of alkaline phosphatise activity (bottom left) as compared with the control (bottom right)
FIG. 3E depicts still further characterization of ECM, obtained as described, after processing and seeding initially with 1 million GFP-positive cells, which stabilized to about 200,000 cells, wherein the stabilized cells often favoured surface attachment sites illustrated in FIG. 3D.

To generate hMSC-derived ECM, which include the collagens just described, cells were cultured as a monolayer and subjected to a 2-stage osteogenic protocol empirically optimized for ECM-yield (as described above). This included a pre-osteogenic, non-mineralizing stage where the cells were exposed to osteogenic media in the absence of dexamethasone but in the presence of GW9662 (e.g. which may be for about 1 week or for 10 days or as needed with suitable media changes), then a mineralizing stage, where the hMSCs received osteogenic media with dexamethasone, but GW9662 was withdrawn (e.g., which may be for another few weeks, 2 weeks or 3 weeks of up to 6 weeks or more with suitable media changes). The monolayers were then recovered and subjected to a series of lyses, enzymatic digestions, solvent extractions and wash steps so as to remove cells and contaminating proteins while maintaining collagen-rich components of the ECM. For example, cells were removed or scraped off and the ECM recovered by enzyme digestion, followed by a trypsin digestion followed by a chloroform extraction followed by drying, e.g., in acetone). After processing, the material had a fibrous appearance at low magnification and consisted of distinct, regularly oriented fibrils when examined by scanning electron microscopy (FIG. 3A). Immunoblotting confirmed that the process depleted contaminating intracellular proteins such as GAPDH and β-actin but enriched the collagen-containing component (FIG. 3B). Complete proteolytic digestion of the ECM resulted in an inorganic residue that could be identified as brushite, a simple form of calcium phosphate ($CaHPO_4 \cdot 2H_2O$) when analyzed by x-ray diffraction (FIG. 3C). When the purified ECM was co-cultured with GFP-labeled hMSCs, the cells oriented themselves on the surface of the material in a manner that resembled a periosteal surface. The resemblance to osteoblasts was also supported by the presence of high ALP activity (FIG. 3D). The additional of ECM provided a setting for accelerating repair and/or retention of the cells to a later phase of repair. Although the cultures were viable for 15 days, initial cell-loss was observed until an equilibrium was achieved, suggesting that binding sites favoring long-term survival are present, but saturable (FIG. 3E).

Figure 4:
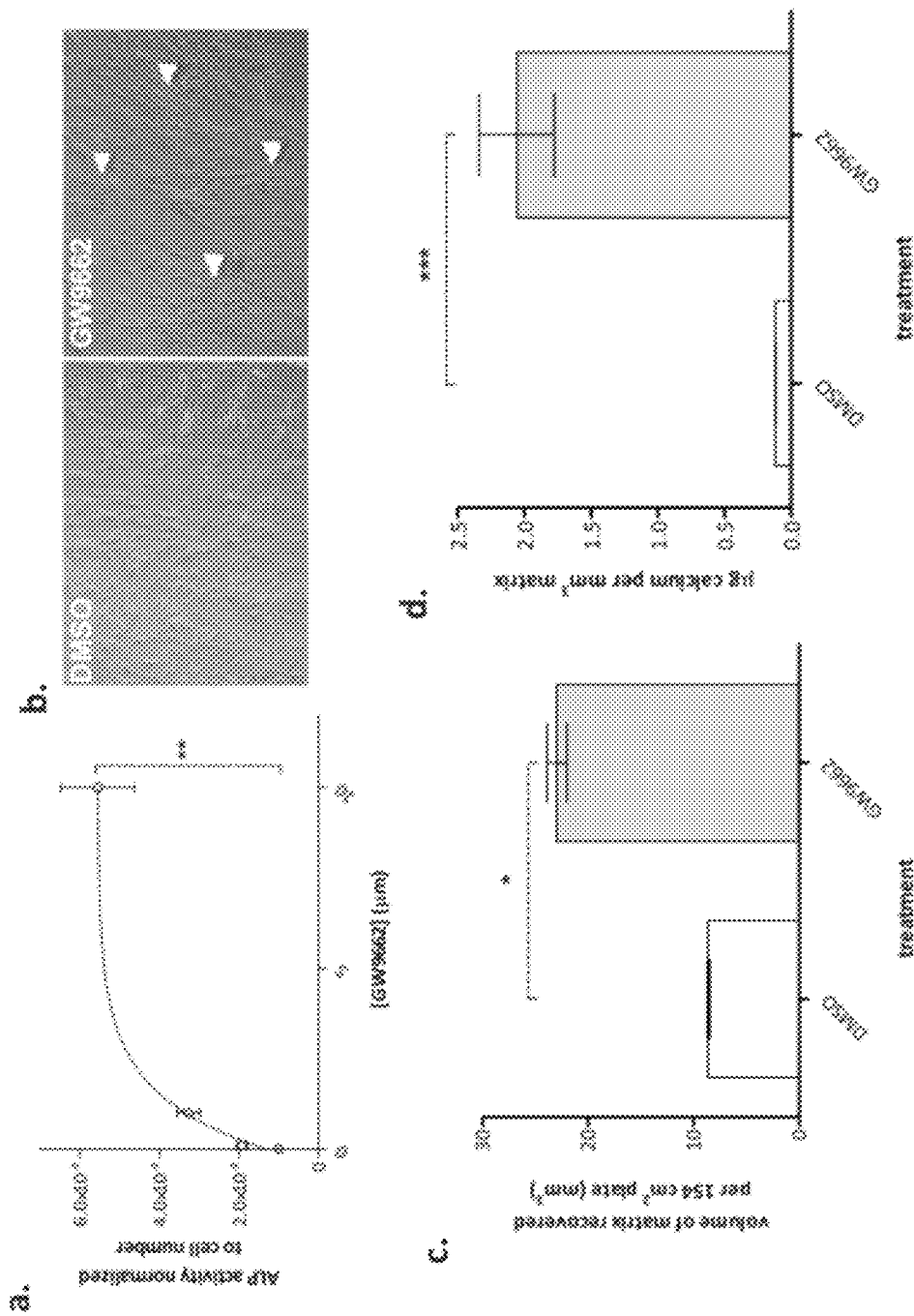
FIGS. 4A-4B depict representative treatment effects as described, in which after GW9662 treatment, ALP activity was substantially up-regulated (FIG. 4A) and the number of ECM nodules detectable by phase microscopy was increased (FIG. 4B, magnification, 10×)
FIG. 4C illustrates a representative volume of ECM recovered after treatment as described, in which there was a substantial increase in the yield with GW9662 treatment.
FIG. 4D depicts representative effect on calcium content in ECM recovered after treatment as described herein, in which the recoverable ECM presented with substantially more calcium mineral than controls (DMSO treatment)

The effect of GW9662 in generating superior ECM preparations was also determined. It was found that the majority of hMSC cultures were highly responsive to GW9662 treatment and this effect was robustly predicted by a dose-dependent increase in ALP activity (FIG. 4A) and distinct formation of nodules when inspected by phase contrast microscopy (FIG. 4B). When ECM was extracted, purified, and analyzed, GW9662 treatment caused a greater volume of ECM to be formed (FIG. 4C) with elevated calcium levels (FIG. 4D) as compared to vehicle treated cells. Therefore, the data clearly indicated that GW9662 had a positive effect on ECM yield, but it was unclear whether the ECM composition had been affected. Conventional proteomic analysis proved impossible due to the physical characteristics of the ECM and its lack of solubility even under common denaturing conditions. Amino acid analysis (AAA) was used in view of the findings suggesting that significant changes in the composition of ECM preparations would be detectable by shifts in the various proportions of amino acids present. In terms of collagen content, these changes would be expected to manifest themselves as variations in amino acids such as glycine, proline and hydroxyproline (hypro) levels.

AAA revealed that ECMs generated from GW9662-treated and control hMSCs were remarkably similar in terms of their amino acid composition with the exception of hypro, which was slightly reduced (14-28% of controls) in GW9662 treated ECM (TABLE 3). These reductions occurred without an associated change in non-hydroxylated proline levels. Although past studies by others have indicated that proline hydroxylase activity is not rate-limiting when collagen synthesis is stimulated, it is possible that the additive influence of GW9662 may inflict a load on the collagen post-translational machinery that accounted for the reduced proportion of hypro in the resultant ECM. There was also a slight but reproducible increase in lysine content. The AAA data, therefore suggested that the effect of GW9662 on hMSC-derived ECM was predominantly on yield rather than composition.

TABLE 3

Amino acid analysis data of cells after reconstruction with and without treatment.

| Residue | DONOR A | | | DONOR B | | |
|---|---|---|---|---|---|---|
| | DMSO proportion | GW9662 proportion | D/G ratio | DMSO proportion | GW9662 proportion | D/G ratio |
| ASX | 0.085221 | 0.08654 | 0.984757 | 0.073121 | 0.077836 | 0.939418 |
| GLX | 0.10935 | 0.107632 | 1.015959 | 0.097774 | 0.107688 | 0.907936 |
| SER | 0.062179 | 0.062954 | 0.987676 | 0.053841 | 0.059299 | 0.907957 |
| HIS | 0.014418 | 0.0153 | 0.94239 | 0.008582 | 0.010154 | 0.845235 |
| GLY | 0.140712 | 0.127937 | 1.099854 | 0.187451 | 0.167353 | 1.120092 |
| THR | 0.046483 | 0.049108 | 0.946545 | 0.04628 | 0.047723 | 0.96976 |
| ALA | 0.109567 | 0.11351 | 0.965258 | 0.114983 | 0.107614 | 1.068474 |
| ARG | 0.051171 | 0.052487 | 0.974922 | 0.049823 | 0.048915 | 1.018547 |
| TYR | 0.02127 | 0.02308 | 0.921605 | 0.01434 | 0.016813 | 0.85289 |
| VAL | 0.055455 | 0.057931 | 0.957273 | 0.051676 | 0.054316 | 0.951388 |
| MET | 0.018695 | 0.021369 | 0.874852 | 0.015943 | 0.015793 | 1.00948 |
| PHE | 0.030288 | 0.031072 | 0.974769 | 0.028127 | 0.02953 | 0.952492 |
| ILE | 0.032222 | 0.034015 | 0.947274 | 0.030528 | 0.032562 | 0.937559 |
| LEU | 0.068791 | 0.072094 | 0.954178 | 0.060033 | 0.063145 | 0.950726 |
| LYS | 0.055017 | 0.058642 | 0.938184 | 0.038591 | 0.042825 | 0.901136 |
| OH-PRO | 0.027883 | 0.020598 | 1.35369 | 0.059729 | 0.05267 | 1.13401 |
| PRO | 0.07128 | 0.065732 | 1.084407 | 0.069178 | 0.065762 | 1.051941 |

To test the effects of the hMSC-derived ECM in vivo, calvarial lesions were generated in nude mice as described previously. During surgery, one group of animals received only pretreated hMSCs (GW-hMSC, which are pretreated with GW9662), one group received ECM only and the final group received both GW-hMSCs and ECM in combination (also referred to as composite). Subsequent cell doses were administered 1 and 2 weeks thereafter by injection and at week 3, mice were euthanized for analysis. Groups that received only ECM or GW-hMSCs exhibited marginal and 60% healing respectively. In contrast, mice that received ECM with GW-hMSCs had substantially healed, with some animals generating levels of bone in excess of the contralateral side (FIGS. 5A, B). When cell engraftment was assayed by RT-PCR, lesions that received only cells had generally low engraftment, reflecting about 2% of the original final dose. In one instance, engraftment was substantially higher than mean levels, but this was not accompanied by increased efficacy. Overall, cell engraftment was substantially higher at week 3 in animals that received the cell-ECM composite (FIG. 5C) reaching levels equivalent to engraftment measured at week 1 in experiment 1. Histologically, GW-hMSCs alone became elongated and clustered sparsely in groups adjacent to the bone tissue (FIG. 5D, left). In contrast, when co-administered with its own ECM, GW-hMSCs were matrix-localized, engrafting in much larger clusters that did not appear to be associated with the remodeling bone surface but nearby, which others have suggested is a preference during healing (FIG. 5D, right). Since the ECM provided additional cell binding sites that are not directly associated with the repairing bone, the mechanism of action appears to be through trophic support rather than direct tissue contribution.

Integrins at the cell surface appeared to be directly regulated by GW9662, in synergy with the differentially expressed collagens. Yet, immunophenotyping demonstrated that integrins commonly associated with osteoblasts, such as beta-1 (CD29), alpha-1 (CD49a), alpha-2 (CD49b), alpha-5 (CD49e) and alpha-v (CD51) were presented at equally high levels on the membranes of GW-hMSCs and untreated hMSCs (TABLE 4). No substantial expression of CD36 (glycoprotein 3b) on the surface of hMSCs could be detected on the membranes of hMSCs irrespective of GW9662 treatment. CD36 is a known ligand of type V collagen, originally discovered as part of the platelet aggregation pathway. Taken together, the lack of integrin and CD26 expression does not support GW9662-mediated receptor-matrix synergy for the most likely candidate collagen receptors.

TABLE 4

Membrane integrin expression of treated and untreated cells by flow cytometric analysis.

| | Control (DMSO treatment) | | GW-treatment | |
|---|---|---|---|---|
| | % pos | x-mean | % pos | x-mean |
| CD29 | 99.89 | 127 | 99.97 | 135 |
| CD36 | 0.60 | 1.95 | 0.68 | 1.89 |
| CD44 | 98.39 | 8.16 | 96.24 | 7.84 |
| CD49a | 89.02 | 3.57 | 87.07 | 3.28 |
| CD49b | 61.63 | 7.78 | 43.09 | 5.69 |
| CD49c | 99.89 | 20.30 | 99.93 | 21.80 |
| CD49e | 99.99 | 85.20 | 99.99 | 81.50 |
| CD51 | 99.91 | 18.20 | 99.92 | 15.30 |

Overall, treatment of hMSCs with a PPARγ inhibitor (e.g., GW9662), not only improved osteogenic differentiation by hMSCs themselves, but also increased the output of ECM, which has excellent cell retention and osteo-inductive properties and therefore useful for cellular-based bone regeneration strategies.

Bone healing is a multi-stage process involving the temporal regulation of a number of distinct phases that have been well characterized in rodent models. Over the 21 day time-course for healing, it was found that retention of pretreated hMSCs at the site of injury was confined to the first two weeks of repair and rapidly dwindled between 2 and 3 weeks (FIG. 2A-C) resulting in up to 60% closure of the lesions (FIG. 2D) when pretreated cells alone were administered to a tissue defect site. Because injections of fresh (pretreated) hMSCs were administered at each week following surgery (FIG. 6B), the reduction in engraftment seemed attributable to the microenvironment rather than the inherent longevity of the cells. Given that the rapid repair phase of IO occurs for about two weeks post injury it seemed that engraftment was coincident with this rapid phase and was attenuated during remodeling. One explanation for these results arises from reports by others of strong mitotic cues persisting for 2 weeks post lesion that cause a rapid expansion of local osteoprogenitor cells. It is however, unlikely that this process entirely explains the observed engraftment kinetics since the addition of hMSC-derived ECM components substantially improved engraftment a week after the predicted end of mitotic burst and thus extended the retention signal for hMSCs at the defect site for prolonged repair and reconstruction.

The extended hMSC retention signal described herein appears beneficial in view of the following: (i) that irrespective of the relatively low level of engraftment at week 3, it remained 2-fold higher with GW-hMSCs, (ii) GW-hMSCs secrete higher levels of ECM collagens when compared to untreated controls, and (iii) GW-hMSCs exhibit greater efficacy in bone repair. Thus, as described, ECM collagens themselves contribute to a retention signal and this in turn, explains the enhanced efficacy observed.

This was confirmed when purified ECM from pretreated hMSCs was co-administered with GW-hMSCs and retention was extended throughout week 3, resulting in substantially improved lesion closure that was complete in most cases (FIG. 5A). Based on the near-exclusive distribution of GW-hMSCs on the ECM, rather than at the surface of the remodeling bone, it is reasonable that at later stages of healing, the GW-hMSCs adopt a bystander or trophic role rather than direct contribution to tissue repair when co-administered with its ECM.

Pretreated hMSCs might generate ECM of a distinct composition that favored retention but biochemical data strongly indicated that pretreatment of hMSCs affected yield of particular ECM components rather than composition (FIGS. 4C, 4D, TABLE 3). Yet, ECM composition changes may still occur because practical constraints limited compositional characterization to AAA and qualitative immunoblotting. Transcriptomic assays of calvarial samples containing untreated and pretreated hMSCs identified a shortlist of up-regulated collagen genes that could represent retention signal candidates including type I, III, V, VI, XI, XII, XIV, XV and XXI collagen (TABLE 1, FIGS. 11, 12, TABLE 2). With the exception of type I and type III collagen that are ubiquitously abundant in bone, type V, VI, XI, XII, XIV, XV collagens have been reported by others to play a role in skeletal development and/or accelerated osteoblast activity. Furthermore, meta-analysis of a transcriptome array dataset presented on the NCBI Gene Expression Omnibus (GSE20980) identified collagen types V, VI, XII and XV to be up-regulated in early rather than late healing of a calvarial defect in rats (TABLE 2). Collagen type XXI was also found to be highly up-regulated with pretreatment of hMSCs with the inhibitor of PPARγ. Since others have found expression of this collagen to be highest in highly vascularized tissues such as heart, stomach and placenta, it may play a role here in supporting angiogenesis.

ECM generated by osteogenic pretreated hMSCs as described herein provides a biologically complex extracellular microenvironment that mimics repairing rather than homeostatic bone tissue, making it distinct from common bone repair scaffolds. Pretreatment of hMSCs was important for the extended healing effect described. The pretreatment effects were observed when hMSCs were initially pretreated for anywhere from about 5 days to about two weeks. Improvements in healing were also observed when hMSCs were pretreated from between about days 7 and 10. The ECM produced after pretreatment was sufficient to extend the retention of the differentiated cells as well as osteoblasts and their progenitors at the defect site, resulting in substantially improved osteogenesis when administered with an appropriate cellular component. As such, hMSC-derived ECM may be employed for surface "bio-conditioning" of commonly used synthetic orthopedic materials to improve osteogenesis and bio-integration MSC-derived ECM is an answer to the allograft biocompatibility issue. The MSC-derived ECM may be allowed to adhere or otherwise interact with a three dimensional scaffold used for repair and reconstruction of tissue. The ECM is allowed to adhere or interact with the scaffold in the absence or presence of the pretreated MSC. In the absence of pretreated MSCs, immune responses should not arise. When combining pretreated MSC with the scaffold in order for the ECM (secreted from the MSCs) to interact with the scaffold, the MSCs may be subsequently removed, may remain or even further cells may be seeded to the scaffold before use at a repair or defect site. In some embodiments, the MSCs may be derived from the same patient to eliminate compatability issues. The final scaffolds when formed (also referred to as bioconditioned scaffolds) may be used immediately or stored by freezing as further described herein.

Figure 13:
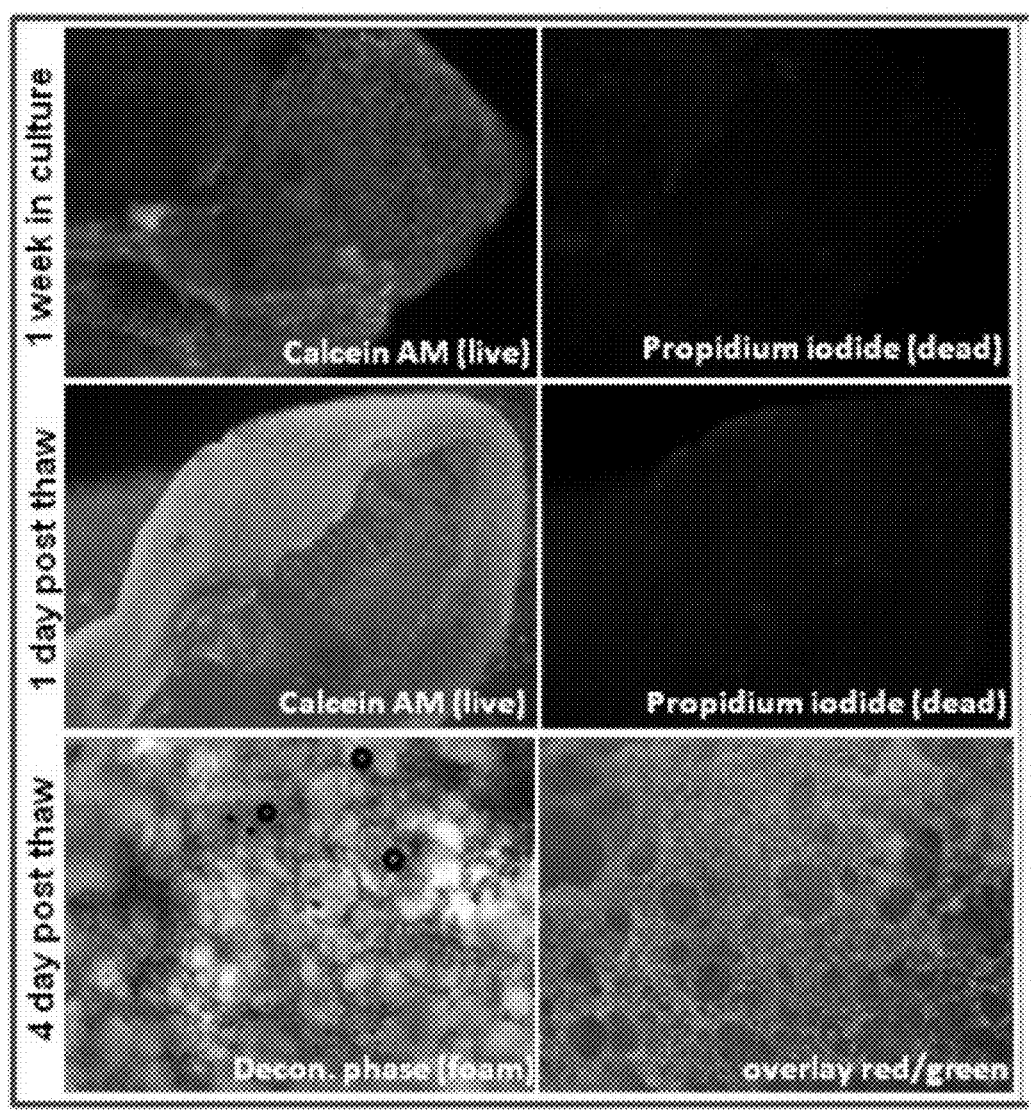
FIG. 13 depicts representative live MSCs in a frozen support as described herein.

In one example one example, scaffolds were loaded with GW9662-treated allogeneic hMSCs. Representative images are depicted in FIG. 13 (top), in which MSCs were initially pre-treated with the PPARγ inhibitor as previously described and cultured with osteogenic media in the presence of a scaffold of type I collagen foam to provide a bioconditioned scaffold after 1 week. The bioconditioned scaffold was then cryopreserved and 1 day after thawing (FIG. 13 middle) or 4 days after thawing (FIG. 13 bottom), the scaffold was imaged. Representative scaffolds include bone (e.g., cadaveric cancellous bone) or collagen type I foam or other suitable three-dimensional network that offers some support, such as polyetheretherketone (PEEK, data not shown).

With FIG. 13, the treated MSCs and scaffold were cultured for 1 week (top images), then frozen. After cryopreserving for 24 hours (at about −80° C. with a DMSO cryomedia), the embedded scaffold was washed and recultured and imaged as depicted in FIG. 13 (middle and bottom). Live and dead cells were visualized by calcein/propidium iodide staining. The bottom images in FIG. 13 show deconvolved phase micrographs of foam with an even distribution of live MSC cells throughout.

Thus, as described herein is a robust and biocompatibile as well as conductive system for numerous repair or reconstruction applications. In one form, the described scaffolding provides an osteogenic and osteoconductive environment for bone tissue repair, reconstruction or replacement. For example, pre-cultured hMSCs can be loaded onto bioconditioned scaffolds such as bone or collagen I foam for efficient in situ cryopreservation. When the live scaffolds are thawed, the cells remain viable (FIG. 13). The bioconditioned scaffold may also be reseeded with new cells prior to use. In some embodiments, the initial MSCs used to prepare the bioconditioned scaffold may be removed prior to cryopreserving.

The described solves a major issue regarding the use of pre-cultured cells in tissue engineering, effectively dismissing the need for a good local clinical manufacturing practice facility. The frozen bioconditioned constructs described herein are a ready to use therapeutic device. Furthermore there is an increasing body of data by others demonstrating that the cells used herein are immune-modulatory, inhibit lymphocyte surveillance, and do not stimulate rejection like other adult tissues. In addition, histocompatibility-matched hMSC libraries may not be necessary with materials and methods described herein.

As described are supports or scaffolds with favorable physical qualities such as, but not limited to, cadaveric cancellous bone, collagen I foam, PEEK that are made more biocompatible by coating the surface with the extracellular matrix components secreted by pre-treated mesenchymal stem cells.

Figure 14:
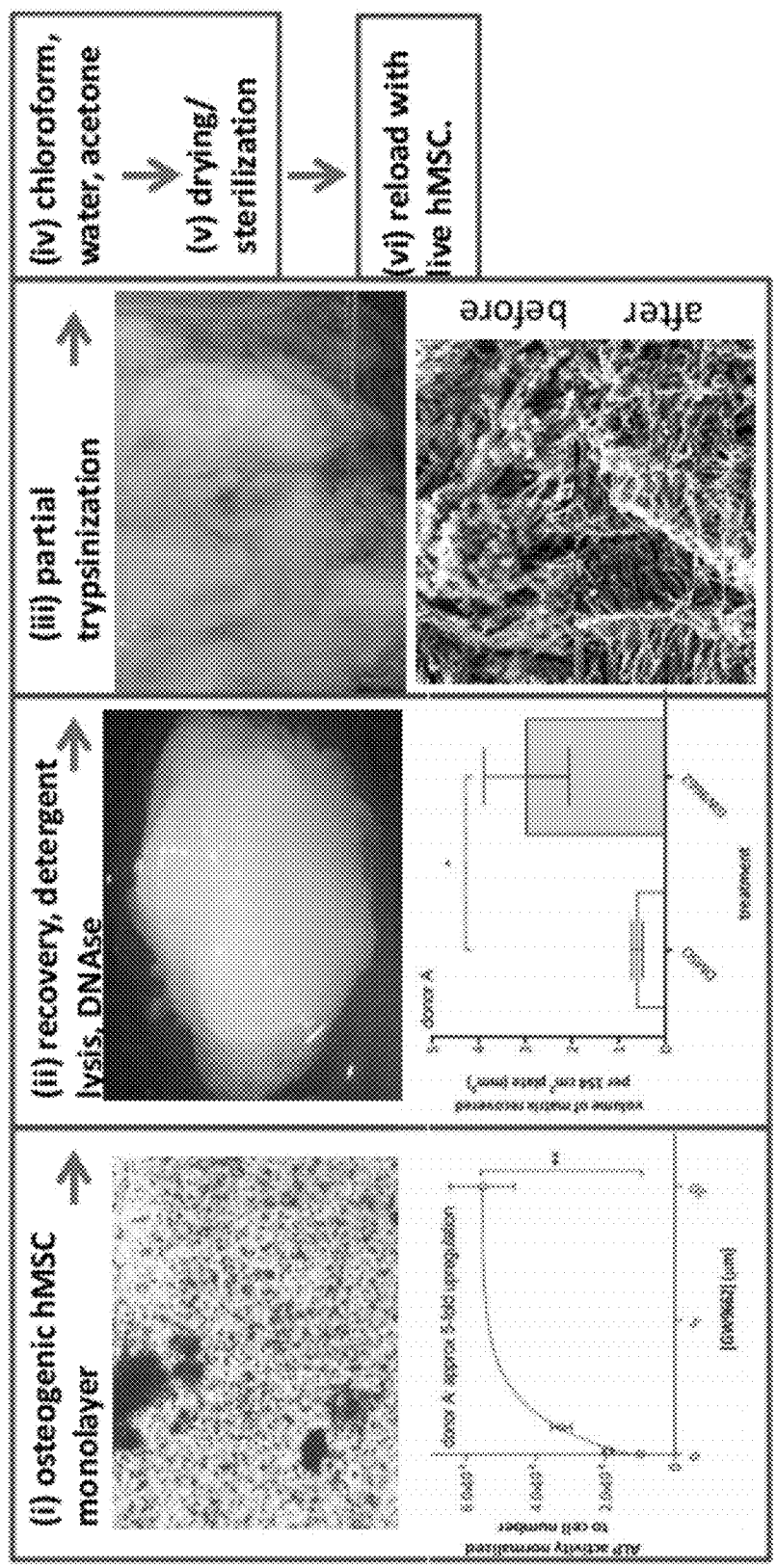
FIG. 14 depicts a representative process for conditioning a scaffold as described herein.

FIG. 14 depicts a representative method described and used for preparing a biocompatible material, in which the biocompatible material was initially seeded with hMSCs (in the presence of additional supplements that promote bone cell type differentiation), which may also include a cell-type specific or protein specific inhibitor, such as an inhibitor of one or more alternative differentiation pathways). Thus, for promoting osteogenic cells, MSCs were seeded on the biocompatible material in an osteogenic-promoting media (as is understood in the art or as discussed previously), and pretreated with an inhibitor of adipogenesis regulation (e.g., PPARγ) before seeding (pre-treatment may occur before or during osteogenic supplementation). The pretreated cells were propagated on the support or scaffold for several days, such as 3 days, or 4 days, or 5 days or 6 days or 7 days or 8 days or 10 days or two weeks or longer. Cells may be cultured for a further set of days (e.g., 3 days, or 4 days or 5 days or 1 week or 8 days or more) with an additive to accelerate further differentiation. With bone cells, the cells may be treated with an additive that promotes a hydroxyapatite or a calcification process, such as calcium phosphate deposition. A suitable example of an additive for hydroxyapatite formation is dexamethasone. Thereafter, the material would generally be decellularized while leaving intact the ECM that was secreted by the cells. Decellularization is generally performed by a series of enzymatic treatments (e.g., trypsin or other suitable compounds) and washes. Thereafter, a bioconditioned material with enhanced cell-retention and biocompatibility properties would be provided that permits an optimal setting for the addition of new cells, such as additional (e.g., differentiated), including pre-treated hMSCs (pretreated in a similar manner as described when initially seeding on the biocompatible support). Bioconditioned matrices seeded with a new preparation of cells (e.g., pre-treated hMSCs) may be immediately used, or supplemented for further growth before use and/or cyropreserved for later use (e.g., immersed in DMSO-containing cryopreservation media and preserved for long periods at a temperature lower than −80° C.). At point-of-care, the stored material can be recovered from cryopreservation and used for implantation, repair or reconstruction. Examples of use include but are not limited to osteo-reconstructive surgeries, such as long bone repair and spine arthrodesis, as representative examples.

Referring again to FIG. 14, box (i) illustrates a monolayer of hMSCs that were grown in vitro in the presence of an osteogenic supplemented media and the PPARγ-inhibitor, GW9662 (see above image). The monolayer of hMSCs when pretreated with GW9662 (in this example, cultured in presence of GW9662), the ALP activity of the cells was substantially upregulated (see bottom image). In box (ii), after culturing, the cell-ECM mixture was recovered (top image) and subjected to a series of detergent extractions and DNAse treatments. The volume of extracted ECM as compared with that from control (DMSO) treated hMSCs is depicted in the bottom of box (ii). In box (iii), the recovered cell-ECM mixture was treated with trypsin and cell binding sites on heterotypic collagen fibrils were observed. In box (iv), the scaffold with ECM was purified and cellular components were removed by a series of washes in chloroform, water and acetone. In box (v), the scaffold with ECM was sterilized and dried chemically and then ready for use, for additional cells or for freezing (box vi).

As described herein, are material and methods to improve tissue healing, such as at a lesion site, defect or site of reconstruction. For bone tissue, osteo-repair capacity of hMSCs can be substantially improvement or augmented, as described and shown, by treatment with an inhibitor of peroxisome proliferator-activated receptor gamma. Efficacy is extended as described herein into the bone remodeling phase, where normally stem cell retention signals are lost and hMSC-mediated healing is generally absent.

As described, a biocompatible scaffold that includes extra cellular matrix components derived from pretreated MSCs are provided that now contain biomolecules (e.g., rich in certain collagen types) for extending healing. In addition, treating MSCs with a targeted inhibitor and co-administering the treated cells with the ECM mixture, retained MSCs at a site of injury well into the remodeling phase of healing. Complete healing was evidenced thereafter. Accordingly, composite materials containing MSC-derived ECM components and inhibitor-treated MSCs improved tissue repair and healing in bone tissue.

As described herein is also a composition comprising MSC pre-cultured in the presence of an agent that activates canonical Wnt signaling therein. There remains a need for compositions of MSCs effective to stimulate osteogenesis at a site of tissue degeneration or injury. Such a deficiency is fulfilled by that described herein.

In one embodiment, the composition further comprises a biocompatible lattice. In one embodiment, the biocompatible lattice is a clotted plasma.

In one embodiment, the agent that activates canonical Wnt signaling therein is an inhibitor of glycogen synthetase kinase-3-beta. In one embodiment, the inhibitor of glycogen synthetase kinase-3-beta selected from the group consisting of bromo-indirubin-oxime, bromo-indirubin-3'-mono-oxide (BIO), 7-azaindolylpyrazinylmaleimide (7AIPM), and a combination thereof.

In one embodiment, the agent that activates canonical Wnt signaling therein is an inhibitor of peroxisome proliferator-activated receptor gamma. In one embodiment, the inhibitor of peroxisome proliferator-activated receptor gamma is 2-chloro-5-nitro-N-phenyl-benzamide (GW9662).

In one embodiment, the pre-cultured MSC exhibits at least one characteristic of a bone cell.

In one embodiment, pre-cultured MSC is partially differentiated into a primitive osteoblast.

The invention also provides a composition comprising a mesenchymal stem cell (MSC) and an agent that activates canonical Wnt signaling therein.

The invention provides a method of treating bone degeneration or injury associated with a pathophysiological condition in a mammal. The method comprises administering to the mammal in need thereof an effective amount of a composition comprising a mesenchymal stem cell (MSC) pre-cultured in the presence of an agent that activates canonical Wnt signaling therein, thereby treating the bone degeneration or injury in the mammal. Preferably, the mammal is a human.

In one embodiment, the method further comprises readministering a composition comprising a mesenchymal stem cell (MSC) pre-cultured in the presence of an agent that activates canonical Wnt signaling therein.

In one embodiment, the composition comprising a mesenchymal stem cell (MSC) pre-cultured in the presence of an agent that activates canonical Wnt signaling therein is readministered about every two weeks.

In one embodiment, the step of administering the composition comprising a mesenchymal stem cell (MSC) pre-cultured in the presence of an agent that activates canonical Wnt signaling therein comprises injecting or implanting the cell into the site of bone degeneration or injury.

In one embodiment, the bone degeneration or injury is associated with a cancer. In one embodiment, the cancer is an osteosarcoma, multiple myeloma or a breast or prostate cancer metastasizing to the bone.

In one embodiment, the bone degeneration or injury is associated with osteoporosis, osteogenesis imperfecta, or severe cranial injury. In one embodiment, the bone injury is a bone fracture or break.

The present invention provides a method of accelerating repair of a skeletal injury in a mammal. The method comprises directly contacting the site of the skeletal injury with an effective amount of a composition comprising a mesenchymal stem cell (MSC) pre-cultured in the presence of an agent that activates canonical Wnt signaling therein thereby accelerating bone repair. Preferably, the mammal is human.

The invention provides a mesenchymal stem cell (MSC) pre-cultured in the presence of an agent that activates canonical Wnt signaling therein, wherein the MSC exhibits an elevated osteogenic characteristic compared to an otherwise identical MSC not pre-cultured in the presence of said agent.

The invention provides an MSC-derived lattice comprising extracellular matrix secreted from an MSC pre-cultured in the presence of an agent that activates canonical Wnt signaling therein that has been induced to differentiate to exhibit at least one characteristic of a bone cell.

In one embodiment, the invention provides an osteogenic composition comprising MSCs pre-cultured in the presence of an agent that accelerates canonical Wnt signaling therein. In some instances, the osteogenic composition comprises a biocompatible gel to incorporate the MSCs therein. An example of a biocompatible gel is clotted plasma. In some instances, the pre-cultured MSC may be partially differentiated into primitive osteoblasts.

In one embodiment, the agent that accelerates canonical Wnt signaling is an inhibitor of glycogen synthetase kinase-3-beta (GSK3β). An example of a GSK3β inhibitor includes but is not limited to bromo-indirubin-oxime, bromo-indirubin-3'-mono-oxide (BIO), 7-azaindolyl-pyrazinylmaleimide (7AIPM), and the like.

In one embodiment, the agent that accelerates canonical Wnt signaling is an inhibitor of peroxisome proliferator-activated receptor gamma (PPARγ). An example of a PPARγ inhibitor is 2-chloro-5-nitro-N-phenyl-benzamide (GW9662).

The present invention provides methods for treating bone degeneration or injury associated with a pathophysiological condition in a mammal by administering to the mammal or contacting the site of injury with the osteogenic composition of the invention.

The invention also provides methods of accelerating repair of a skeletal injury in a mammal by administering to the mammal or contacting the site of injury with the osteogenic composition.

MSCs treated according to the invention can significantly accelerate the repair of bone without the necessity for prosthetic reconstruction, or the requirement for donor bone tissue. The method of the invention therefore has great utility in simplifying the treatment of traumatic bone injury. Furthermore, this method can dramatically accelerate the healing of less severe fractures, allowing recipients to regain mobility after a shorter duration.

As used herein, the following terms have meanings associated with them.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used.

"Alloantigen" is an antigen that differs from an antigen expressed by the recipient.

As used here, "biocompatible" refers to any material, which, when implanted in a mammal, does not provoke an adverse response in the mammal. A biocompatible material, when introduced into an individual, is not toxic or injurious to that individual, nor does it induce immunological rejection of the material in the mammal.

As used herein, the term "biocompatible lattice," is meant to refer to a substrate that can facilitate formation into three-dimensional structures conducive for tissue development. Thus, for example, cells can be cultured or seeded onto such a biocompatible lattice, such as one that includes extracellular matrix material, synthetic polymers, cytokines, growth factors, etc. The lattice can be molded into desired shapes for facilitating the development of tissue types. Also, at least at an early stage during culturing of the cells, the medium and/or substrate is supplemented with factors (e.g., growth factors, cytokines, extracellular matrix material, etc.) that facilitate the development of appropriate tissue types and structures.

"Bioactive agents," as used herein, can include one or more of the following: chemotactic agents; therapeutic agents (e.g., antibiotics, steroidal and non-steroidal analgesics and anti-inflammatories (including certain amino acids such as glycine), anti-rejection agents such as immunosuppressants and anti-cancer drugs); various proteins (e.g., short term peptides, bone morphogenic proteins, collagen, hyaluronic acid, glycoproteins, and lipoprotein); cell attachment mediators; biologically active ligands; integrin binding sequence; ligands; various growth and/or differentiation agents and fragments thereof (e.g., epidermal growth factor (EGF), hepatocyte growth factor (HGF), vascular endothelial growth factors (VEGF), fibroblast growth factors (e.g., bFGF), platelet derived growth factors (PDGF), insulin derived growth factor (e.g., IGF-1, IGF-II) and transforming growth factors (e.g., TGFP I-III), parathyroid hormone, parathyroid hormone related peptide, bone morphogenic proteins (e.g., BMP-2, BMP-4; BMP-6; BMP-7; BMP-12; BMP-13; BMP-14), sonic hedgehog, growth differentiation factors (e.g., GDF5, GDF6, GDF8), recombinant human growth factors (e.g., MP52, and MP-52 variant rhGDF-5), cartilage-derived morphogenic proteins (CDMP-1; CDMP-2, CDMP-3)); small molecules that affect the upregulation of specific growth factors; tenascin-C; hyaluronic acid; chondroitin sulfate; fibronectin; decorin; thromboelastin; thrombin-derived peptides; heparin-binding domains; heparin; heparan sulfate. Suitable effectors likewise include the agonists and antagonists of the agents described above.

The growth factor can also include combinations of the growth factors described above. In addition, the growth factor can be autologous growth factor that is supplied by platelets in the blood. In this case, the growth factor from platelets will be an undefined cocktail of various growth factors. If other such substances have therapeutic value in the orthopedic field, it is anticipated that at least some of these substances will have use in the present invention, and such substances should be included in the meaning of "bioactive agent" and "bioactive agents" unless expressly limited otherwise. Preferred examples of bioactive agents include culture media, bone morphogenic proteins, growth factors, growth differentiation factors, recombinant human growth factors, cartilage-derived morphogenic proteins, hydrogels, polymers, antibiotics, anti-inflammatory medications, immunosuppressive mediations, autologous, allogenic or xenologous cells such as stem cells, chondrocytes, fibroblast and proteins such as collagen and hyaluronic acid. Bioactive agents can be autologus, allogenic, xenogenic or recombinant.

The term "biologically compatible carrier" or "biologically compatible medium" refers to reagents, cells, compounds, materials, compositions, and/or dosage formulations which are suitable for use in contact with the tissues of human beings and animals without excessive toxicity, irritation, allergic response, or other complication commensurate with a reasonable benefit/risk ratio.

As used herein, the term "bone condition (or injury or disease)" refers to disorders or diseases of the bone including, but not limited to, acute, chronic, metabolic and non-metabolic conditions of the bone. The term encompasses conditions caused by disease, trauma or failure of the tissue to develop normally. Examples of bone conditions include, but are not limited, a bone fracture, a bone/spinal deformation, osteosarcoma, myeloma, bone dysplasia, scoliosis, osteoporosis, osteomalacia, rickets, fibrous osteitis, renal bone dystrophy, and Paget's disease of bone.

As used herein, the term "bone marrow stromal cells," "stromal cells," "mesenchymal stem cells," "mesenchymal stromal cells" or "MSCs" are used interchangeably and refer to a cell derived from bone marrow (Prockop, 1997), peripheral blood (Kuznetsov et al., 2001), adipose tissue (Guilak et al., 2004), umbilical cord blood (Rosada et al., 2003), synovial membranes (De Bari et al., 2001), and periodontal ligament (Seo et al., 2005). MSCs are characterized by their ability to adhere to plastic tissue culture surfaces (Friedenstein et al.; Owen & Friedenstein, 1988), and by being an effective feeder layers for hematopoietic stem cells (Eaves et al., 2001). In addition, MSCs can be differentiated both in culture and in vivo into osteoblasts and chondrocytes, into adipocytes, muscle cells (Wakitani et al., 1995) and cardiomyocytes (Fukuda and Yuasa, 2006), into neural precursors (Woodbury et al., 2000; Deng et al., 2001, Kim et al., 2006; Mareschi et al., 2006; Krampera et al., 2007). Mesenchymal stem cells (MSCs) may be purified using methods known in the art (Wakitani et al., 1995; Fukuda and Yuasa, 2006; Woodbury et al., 2000; Deng et al., 2001; Kim et al., 2006; Mareschi et al., 2006; Krampera et al., 2007).

"Differentiation medium" is used herein to refer to a cell growth medium comprising an additive or a lack of an additive such that a stem cell, adipose derived adult stromal cell or other such progenitor cell, that is not fully differentiated when incubated in the medium, develops into a cell with some or all of the characteristics of a differentiated cell.

As used herein "endogenous" refers to any material from or produced inside an organism, cell or system.

"Exogenous" refers to any material introduced from or produced outside an organism, cell, or system.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, a "graft" refers to a cell, tissue or organ that is implanted into an individual, typically to replace, correct or otherwise overcome a defect. A graft may further comprise a scaffold. The tissue or organ may consist of cells that originate from the same individual; this graft is referred to herein by the following interchangeable terms: "autograft," "autologous transplant," "autologous implant" and "autologous graft". A graft comprising cells from a genetically different individual of the same species is referred to herein by the following interchangeable terms: "allograft," "allogeneic transplant," "allogeneic implant" and "allogeneic graft". A graft from an individual to his identical twin is referred to herein as an "isograft", a "syngeneic transplant," a "syngeneic implant" or a "syngeneic graft". A "xenograft," "xenogeneic transplant" or "xenogeneic implant" refers to a graft from one individual to another of a different species.

By "growth factors" is intended the following non-limiting factors including, but not limited to, growth hormone, erythropoietin, thrombopoietin, interleukin 3, interleukin 6, interleukin 7, macrophage colony stimulating factor, c-kit ligand/stem cell factor, osteoprotegerin ligand, insulin, insulin like growth factors, epidermal growth factor (EGF), fibroblast growth factor (FGF), nerve growth factor, ciliary neurotrophic factor, platelet derived growth factor (PDGF), and bone morphogenetic protein at concentrations of between picogram/ml to milligram/ml levels.

As used herein, the term "growth medium" is meant to refer to a culture medium that promotes growth of cells. A growth medium will generally contain animal serum. In some instances, the growth medium may not contain animal serum.

An "isolated cell" refers to a cell which has been separated from other components and/or cells which naturally accompany the isolated cell in a tissue or mammal.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

As used herein, the term "multipotential" or "multipotentiality" is meant to refer to the capability of a stem cell of the central nervous system to differentiate into more than one type of cell.

As used herein, the term "modulate" is meant to refer to any change in biological state, i.e. increasing, decreasing, and the like.

The terms "precursor cell," "progenitor cell," and "stem cell" are used interchangeably in the art and herein and refer either to a pluripotent, or lineage-uncommitted, progenitor cell, which is potentially capable of an unlimited number of mitotic divisions to either renew itself or to produce progeny cells which will differentiate into the desired cell type. Unlike pluripotent stem cells, lineage-committed progenitor cells are generally considered to be incapable of giving rise to numerous cell types that phenotypically differ from each other. Instead, progenitor cells give rise to one or possibly one or more lineage-committed cell types.

As used herein, "scaffold" refers to a structure, comprising a biocompatible material, that provides a surface suitable for adherence and proliferation of cells. A scaffold may further provide mechanical stability and support. A scaffold may be in a particular shape or form so as to influence or delimit a three-dimensional shape or form assumed by a population of proliferating cells. Such shapes or forms include, but are not limited to, films (e.g. a form with two-dimensions substantially greater than the third dimension), ribbons, cords, sheets, flat discs, cylinders, spheres, 3-dimensional amorphous shapes, etc.

The term "stromal cell medium" as used herein, refers to a medium useful for culturing ADAS cells. An example of a stromal cell medium is a medium comprising DMEM/F 12 Ham's, 10% fetal bovine serum, 100 U penicillin/100 µg streptomycin/0.25 Fungizone. Typically, the stromal cell medium comprises a base medium, serum and an antibiotic/antimycotic. However, ADAS cells can be cultured with stromal cell medium without an antibiotic/antimycotic and supplemented with at least one growth factor. Preferably the growth factor is human epidermal growth factor (hEGF). The preferred concentration of hEGF is about 1-50 ng/ml, more preferably the concentration is about 5 ng/ml. The preferred base medium is DMEM/F12 (1:1). The preferred serum is fetal bovine serum (FBS) but other sera may be used including horse serum or human serum. Preferably up to 20% FBS will be added to the above media in order to support the growth of stromal cells. However, a defined medium could be used if the necessary growth factors, cytokines, and hormones in FBS for stromal cell growth are identified and provided at appropriate concentrations in the growth medium. It is further recognized that additional components may be added to the culture medium. Such components include but are not limited to antibiotics, antimycotics, albumin, growth factors, amino acids, and other components known to the art for the culture of cells. Antibiotics which can be added into the medium include, but are not limited to, penicillin and streptomycin. The concentration of penicillin in the culture medium is about 10 to about 200 units per ml. The concentration of streptomycin in the culture medium is about 10 to about 200 µg/ml. However, the invention should in no way be construed to be limited to any one medium for culturing stromal cells. Rather, any media capable of supporting stromal cells in tissue culture may be used.

"Transplant" refers to a biocompatible lattice or a donor tissue, organ or cell, to be transplanted. An example of a transplant may include but is not limited to skin cells or tissue, bone marrow, and solid organs such as heart, pancreas, kidney, lung and liver. Preferably, the transplant is a human neural stem cell.

A "vector" is a composition of matter which comprises an isolated nucleic acid and which can be used to deliver the isolated nucleic acid to the interior of a cell.

Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Wnt proteins form a family of highly conserved secreted signaling molecules that regulate cell-to-cell interactions during embryogenesis. The terms "Wnts" or "Wnt gene product" or "Wnt polypeptide" when used herein encompass native sequence Wnt polypeptides, Wnt polypeptide variants, Wnt polypeptide fragments and chimeric Wnt polypeptides.

The term "agonist" refers to an agent or analog that binds productively to a receptor and mimics its biological activity. The term "antagonist" refers to an agent that binds to receptors but does not provoke the normal biological response. Thus, an antagonist potentiates or recapitulates, for example, the bioactivity of patched, such as to repress transcription of target genes. The term "Wnt antagonist" as used herein refers not only to any agent that may act by directly inhibiting the normal function of the Wnt protein, but also to any agent that inhibits the Wnt signaling pathway, and thus recapitulates the function of Wnt. The term "Wnt agonist" likewise refers to an agent which antagonizes or blocks the bioactivity of Wnt, such as to increase transcription of target genes.

As now further described are materials and methods for treating MSCs with an agent that enhances Wnt signaling in the MSC so that the treated MSC exhibit an enhanced osteogenic characteristic compared to an otherwise identical MSC not treated with the agent. The treated MSC produced by the methods of the invention are useful in providing a source of cells for research or transplantation. Thus, in one embodiment, the invention provides a method of treating MSCs to enhance the capacity of the MSCs for osteogenic cytotherapy comprising contacting the cells with an agent that enhances Wnt signaling in the cell.

The present invention relates to the discovery that contacting an MSC with an agent that enhances Wnt signaling in the cell enhances the osteogenic characteristic of the MSC. Preferably, the MSC is human MSC. In some instances, the agent can be contacted with any desirable cell having the ability to differentiate into a bone cell to increase the osteogenic characteristic of the cell.

The cells of the invention are useful for treating a bone degeneration or bone injury in a mammal. In some instances, the bone degeneration or injury may be associated with a cancer. The cancer may be a solid cancer, for example osteosarcoma, or a disseminated cancer, e.g., multiple myeloma, or a cancer that metastasizes to the bone, such as, breast cancer or prostate cancer. Also, the bone degeneration or injury may be associated with or may result from osteoporosis, osteogenesis imperfecta, or severe cranial injury. In addition, the bone injury may result from a fracture or a break from trauma resulting from osteoporosis, osteogenesis imperfecta or cranial injury or may result from another trauma.

Pre-treatment. The invention comprises the treatment of a cell having the potential to differentiate into a bone cell to enhance the osteogenic characteristic of the cell. Preferably, the cell having the differentiation potential is an MSC. While the invention is not bound by any theory of operation, it is believed that treatment of the MSC with an agent that enhances Wnt signaling in the cell enhances the osteogenic characteristic of the cell.

Accordingly, the present invention provides osteogenic compositions or formulations of mesenchymal stem cells (MSC) that are conditioned into becoming predominantly osteogenic upon administration in humans or animals. In one embodiment, the MSCs are pre-cultured in the presence of an agent that enhances Wnt signaling in the cell. In another embodiment, the agent that enhances Wnt signaling in a cell is an inhibitor of, for example, glycogen synthetase kinase-3-beta (GSK3β), peroxisome proliferator-activated receptor gamma (PPARγ), or a combination thereof. An example of a GSK3β inhibitor includes but is not limited to bromo-indirubin-oxime, bromo-indirubin-3'-mono-oxide (BIO), 7-azaindolyl-pyrazinylmaleimide (7AIPM), and the like. An example of a PPARγ inhibitor is 2-chloro-5-nitro-N-phenyl-benzamide (GW9662).

In some instances, the MSC is contacted with an agent that enhances Wnt signaling in the cell in a culturing medium. The culturing medium generally comprises a base media. Non-limiting examples of base media useful in the methods of the invention include Minimum Essential Medium Eagle, ADC-1, LPM (Bovine Serum Albumin-free), F1O (HAM), F12 (HAM), DCCM1, DCCM2, RPMI 1640, BGJ Medium (with and without Fitton-Jackson Modification), Basal Medium Eagle (BME-with the addition of Earle's salt base), Dulbecco's Modified Eagle Medium (DMEM-without serum), Yamane, IMEM-20, Glasgow Modification Eagle Medium (GMEM), Leibovitz L-15 Medium, McCoy's 5A Medium, Medium M199 (M199E-with Earle's sale base), Medium M199 (M199H-with Hank's salt base), Minimum Essential Medium Eagle (MEM-E-with Earle's salt base), Minimum Essential Medium Eagle (MEM-H-with Hank's salt base) and Minimum Essential Medium Eagle (MEM-NAA with non essential amino acids), among numerous others, including medium 199, CMRL 1415, CMRL 1969, CMRL 1066, NCTC 135, MB 75261, MAB 8713, DM 145, Williams' G, Neuman & Tytell, Higuchi, MCDB 301, MCDB 202, MCDB 501, MCDB 401, MCDB 411, MDBC 153. A preferred medium for use in the present invention is DMEM. These and other useful media are available from GIBCO, Grand Island, N.Y., USA and Biological Industries, Bet HaEmek, Israel, among others. A number of these media are summarized in Methods in Enzymology, Volume LVIII, "Cell Culture," pp. 62-72.

Additional non-limiting examples of media useful in the methods of the invention can contain fetal serum of bovine or other species at a concentration of at least 1% to about 30%, preferably at least about 5% to 15%, mostly preferably about 10%. Embryonic extract of chicken or other species can be present at a concentration of about 1% to 30%, preferably at least about 5% to 15%, most preferably about 10%.

In another embodiment, the invention provides a method for differentiating an MSC that has been pre-treated with an agent that enhances Wnt signaling in the cell to express at least one characteristic of a cell of the bone lineage. In some instances, the MCSs are plated to a useful density, including but not limited to a density of about 1,000 to about 500,000 cells/cm$^2$; incubating the cells in a chemically defined culture medium. In one embodiment, the MSCs are differentiated to express at least one protein characteristic of a bone cell. In another embodiment, the MSCs are differentiated to exhibit a morphological characteristic of a bone derived cell.

Differentiation media useful in the methods of the invention may contain one or more compounds of interest, including, but not limited to, antibiotics, compounds that are osteoinductive, osteoconductive, or promote growth or differentiation, such as bone morphogenetic proteins or other growth factors. Examples of bone morphogenetic proteins include, but are not limited to, osteogenic protein-1, BMP-5, osteogenin, osteoinductive factor and bone morphogenetic protein-4 (Asahina et al. (1996) Exp Cell Res 222:38-47; Takuwa (1991) Biochem Biophys Res Com 174:96-101; Chen (1991) J Bone M M Res 6:1387-1390; Sampath (1992) J Biol Chem 267:20352-20362; Wozney et al. 1988 Science 242:1528-1534, the contents of which are incorporated herein by reference), and the like.

The presence of the differentiated cells of the invention may be detected by a variety of techniques including, but not limited to, flow cytometric, immunohistochemical, in situ hybridization, and/or other histologic or cellular biologic techniques. See, e.g., Kopen et al., 1999, Proc Natl Acad Sci 96:10711-10716.

Cells exhibiting at least one characteristic of a bone cell of the invention may be introduced into the bone of a human or animal subject at the site of surgery or fracture. Introduction of an osteogenic cell of the invention to bone is useful in the treatment of bone fractures and bone disorders, including osteoporosis. Thus, in another embodiment, the invention is directed to a method of improving a mammal's bone structure, comprising: a) culturing MSCs in a composition which comprises a medium capable of supporting the growth of MSCs and differentiation inducing amounts a differentiation agent in combination with an agent that enhances Wnt signaling in a cell; b) introducing the treated MSC into a surgery or fracture site of a mammal in need thereof mammal.

Preferably, the MSCs are isolated from the mammal into which the treated MSC are to be introduced. However, the MSCs may also be isolated from an organism of the same or different species as the mammal. The mammal may be any organism having bone tissue. Preferably the mammal is a human.

Genetic Modification. The cells of the invention may be stably or transiently transformed with a nucleic acid of interest prior to introduction into a surgery or fracture site of the mammal. Nucleic acid sequences of interest include, but are not limited to those encoding gene products that enhance the growth, differentiation and/or mineralization of bone cells. For example, an expression system for bone morphogenetic protein 4, can be introduced into the MSCs in a stable or transient fashion for the purpose of treating non-healing fractures or osteoporosis. Methods of transformation of MSCs are known to those skilled in the art, as are methods for introducing cells into a bone at the site of surgery or fracture.

In cases in which a gene construct is transfected into a cell, the heterologous gene is operably linked to regulatory sequences required to achieve expression of the gene in the cell. Such regulatory sequences typically include a promoter and a polyadenylation signal.

The gene construct is preferably provided as an expression vector that includes the coding sequence for a heterologous protein operably linked to essential regulatory sequences such that when the vector is transfected into the cell, the coding sequence will be expressed by the cell. The coding sequence is operably linked to the regulatory elements necessary for expression of that sequence in the cells. The nucleotide sequence that encodes the protein may be cDNA, genomic DNA, synthesized DNA or a hybrid thereof, or an RNA molecule such as mRNA. The gene construct includes the nucleotide sequence encoding the beneficial protein operably linked to the regulatory elements and may remain present in the cell as a functioning cytoplasmic molecule, a functioning episomal molecule or it may integrate into the cell's chromosomal DNA. Exogenous genetic material may be introduced into cells where it remains as separate genetic material in the form of a plasmid. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Alternatively, RNA may be introduced into the cell.

The regulatory elements for gene expression include: a promoter, an initiation codon, a stop codon, and a polyadenylation signal. It is preferred that these elements be operable in the cells of the present invention. Moreover, it is preferred that these elements be operably linked to the nucleotide sequence that encodes the protein such that the nucleotide sequence can be expressed in the cells and thus the protein can be produced. Initiation codons and stop codons are generally considered to be part of a nucleotide sequence that encodes the protein. However, it is preferred that these elements are functional in the cells. Similarly, promoters and polyadenylation signals used must be functional within the cells of the present invention. Examples of promoters useful to practice the present invention include but are not limited to promoters that are active in many cells such as the cytomegalovirus promoter, SV40 promoters and retroviral promoters. Other examples of promoters useful to practice the present invention include but are not limited to tissue-specific promoters, i.e. promoters that function in some tissues but not in others; also, promoters of genes normally expressed in the cells with or without specific or general enhancer sequences. In some embodiments, promoters are used which constitutively express genes in the cells with or without enhancer sequences. Enhancer sequences are provided in such embodiments when appropriate or desirable.

The cells of the present invention can be transfected using well known techniques readily available to those having ordinary skill in the art. Exogenous genes may be introduced into the cells using standard methods where the cell expresses the protein encoded by the gene. In some embodiments, cells are transfected by calcium phosphate precipitation transfection, DEAE dextran transfection, electroporation, microinjection, liposome-mediated transfer, chemical-mediated transfer, ligand mediated transfer or recombinant viral vector transfer.

In some embodiments, recombinant adenovirus vectors are used to introduce DNA with desired sequences into the cell. In some embodiments, recombinant retrovirus vectors are used to introduce DNA with desired sequences into the cells. In other embodiments, standard CaPO4, DEAE dextran or lipid carrier mediated transfection techniques are employed to incorporate desired DNA into dividing cells. In some embodiments, DNA is introduced directly into cells by microinjection. Similarly, well-known electroporation or particle bombardment techniques can be used to introduce foreign DNA into the cells. A second gene is usually co-transfected or linked to the therapeutic gene. The second gene is frequently a selectable antibiotic-resistance gene. Standard antibiotic resistance selection techniques can be used to identify and select transfected cells. Transfected cells are selected by growing the cells in an antibiotic that will kill cells that do not take up the selectable gene. In most cases where the two genes co-transfected and unlinked, the cells that survive the antibiotic treatment contain and express both genes.

In another embodiment, the cells of the invention can be genetically modified, e.g., to express exogenous genes or to repress the expression of endogenous genes. In accordance with this embodiment, the cell is exposed to a gene transfer vector comprising a nucleic acid including a transgene, such that the nucleic acid is introduced into the cell under conditions appropriate for the transgene to be expressed within the cell. The transgene generally is an expression cassette, including a coding polynucleotide operably linked to a suitable promoter. The coding polynucleotide can encode a protein, or it can encode biologically active RNA, such as antisene RNA or a ribozyme. Thus, the coding polynucleotide can encode a gene conferring, for example, resistance to a toxin, a hormone (such as peptide growth hormones, hormone releasing factor, sex hormones, adrenocorticotrophic hormones, cytokines such as interferons, interleukins, and lymphokines), a cell surface-bound intracellular signaling moiety such as cell-adhesion molecules and hormone receptors, and factors promoting a given lineage of differentiation, or any other transgene with known sequence.

The expression cassette containing the transgene should be incorporated into the genetic vector suitable for delivering the transgene to the cell. Depending on the desired end application, any such vector can be so employed to genetically modify the cells (e.g., plasmids, naked DNA, viruses such as adenovirus, adeno-associated virus, herpesvirus, lentivirus, papillomavirus, retroviruses, etc.). Any method of constructing the desired expression cassette within such vectors can be employed, many of which are well known in the art, such as by direct cloning, homologous recombination, etc. The desired vector will largely determine the method used to introduce the vector into the cells, which are generally known in the art. Suitable techniques include protoplast fusion, calcium-phosphate precipitation, gene gun, electroporation, and infection with viral vectors.

It should be understood that the methods described herein may be carried out in a number of ways and with various modifications and permutations thereof that are well known in the art. It should also be appreciated that any theories set forth as to modes of action or interactions between cell types should not be construed as limiting this invention in any manner, but are presented such that the methods of the invention can be more fully understood.

Scaffold. The cells of the invention may be introduced alone or in admixture with a composition useful in the repair of bone wounds and defects. Such compositions include, but are not limited to bone morphogenetic proteins, hydroxyapatite/tricalcium phosphate particles (HA/TCP), gelatin, poly-L-lysine, and collagen.

MSCs can be derived in great quantities from the recipient's bone marrow and, using the novel culture conditions, can be induced to differentiate into an osteoprogenitor cell with great capacity to regenerate bone. Confined in biocompoatible gels such as, but not limited to, clotted plasma, the cells build new bone at the site and induce the infiltration of new blood vessels which is a critical requirement for bone growth). The treated MSCs also produce a countless number of secreted growth factors, cytokines and structural proteins, including, but not limited to collagen I and BMP2. Since the new material is real bone, and the cells are from the recipient or a compatible donor, rejection and maintenance is not an issue.

The present invention includes using a scaffold to deliver cells to the desired tissue. The cells can be seeded onto or into a three-dimensional scaffold and administered in vivo in a mammal, where the seeded cells proliferate on the framework and form a replacement tissue in vivo in cooperation with the cells of the mammal.

In some embodiments of the invention, the scaffold comprises extracellular matrix, cell lysate (e.g., soluble cell fractions), or combinations thereof, of the desired cells. In some embodiments, the scaffold comprises an extracellular matrix protein secreted by the cells of the invention. Alternatively, the extracellular matrix is an exogenous material selected from the group consisting of calcium alginate, agarose, fibrin, collagen, laminin, fibronectin, glycosaminoglycan, hyaluronic acid, heparin sulfate, chondroitin sulfate A, dermatan sulfate, and bone matrix gelatin. In some embodiments, the matrix comprises natural or synthetic polymers.

The invention includes biocompatible scaffolds, lattices, self-assembling structures and the like, whether biodegradable or not, liquid or solid. Such scaffolds are known in the art of cell-based therapy, surgical repair, tissue engineering, and wound healing. Preferably the scaffolds are pretreated (e.g., seeded, inoculated, contacted with) with the cells, extracellular matrix, conditioned medium, cell lysate, or combination thereof. In some embodiments of the invention, the cells adhere to the scaffold. The seeded scaffold can be introduced into the mammal in any way known in the art, including but not limited to implantation, injection, surgical attachment, transplantation with other tissue, injection, and the like. The scaffold of the invention may be configured to the shape and/or size of a tissue or organ in vivo. For example, but not by way of limitation, the scaffold may be designed such that the scaffold structure supports the seeded cells without subsequent degradation; supports the cells from the time of seeding until the tissue transplant is remodeled by the host tissue; and allows the seeded cells to attach, proliferate, and develop into a tissue structure having sufficient mechanical integrity to support itself. Scaffolds of the invention can be administered in combination with any one or more growth factors, cells, drugs or other and/or components described elsewhere herein that stimulate tissue formation or otherwise enhance or improve the practice of the invention. The cells to be seeded onto the scaffolds may be genetically engineered to express growth factors or drugs.

In another preferred embodiment, the cells of the invention are seeded onto a scaffold where the material exhibits specified physical properties of porosity and biomechanical strength to mimic the features of natural bone, thereby promoting stability of the final structure and access and egress of metabolites and cellular nutrients. That is, the material should provide structural support and can form a scaffolding into which host vascularization and cell migration can occur. In this embodiment, the desired cells are first mixed with a carrier material before application to a scaffold. Suitable carriers include, but are not limited to, calcium alginate, agarose, types I, II, IV or other collagen isoform, fibrin, poly-lactic/poly-glycolic acid, hyaluronate derivatives, gelatin, laminin, fibronectin, starch, polysaccharides, saccharides, proteoglycans, synthetic polymers, calcium phosphate, and ceramics (i.e., hydroxyapatite, tricalcium phosphate).

The external surfaces of the three-dimensional framework may be modified to improve the attachment or growth of cells and differentiation of tissue, such as by plasma coating the framework or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate), a cellular matrix, and/or other materials such as, but not limited to, gelatin, alginates, agar, and agarose.

In some embodiments, it is important to re-create in culture the cellular microenvironment found in vivo. In addition, growth factors, osteogenic inducing agents, and angiogenic factors may be added to the culture medium prior to, during, or subsequent to inoculation of the cells to trigger differentiation and tissue formation by the cells following administration into the mammal.

Therapy. Disclosed herein is the induction of canonical Wnt signaling in an MSC to enhance the osteogenic characteristic of the cell. Induction of Wnt signaling can be accomplished by inhibition of GSKβ, inhibition of PPARγ, or a combination thereof. Indication of Wnt signaling accelerates osteogenic differentiation by MSCs in vivo and in vitro and partially differentiates them into primitive osteoblasts. It is contemplated that these drugs increase bone mineral levels in a variety of bone degenerative diseases including osteoporosis, some forms of malignant bone disease, some forms of osteogenesis imperfecta and also in the treatment of serious skeletal injuries.

The present invention provides compositions and methods for enhancing the osteogenic characteristic of MSCs. Accordingly, the MSCs treated using the methods of the invention can significantly accelerate the repair of a bone injury, disease, or disorder. In some instances, the MSCs of the invention can treat a bone injury, disease, or disorder without the necessity for prosthetic reconstruction, or the requirement for donor bone tissue. Thus, the invention has a great utility in simplifying the treatment of bone injury. Furthermore, the methods can dramatically accelerate the healing of less severe fractures, allowing recipients to regain mobility after a shorter duration.

The invention also provides a method of treating bone degeneration or injury associated with a pathophysiological condition in a mammal, comprising administering to the mammal an effective amount of the osteogenic composition of the invention to accelerate bone repair, thereby treating the bone degeneration or injury. In one embodiment, the method comprises readministering the osteogenic composition periodically. Particularly the osteogenic composition may be readministered about every two weeks.

Administration of the osteogenic composition of the invention may comprise injecting or implanting the same into the site of bone degeneration or injury. In one embodiment the bone degeneration or injury may be associated with a cancer. Examples of a cancer are an osteosarcoma, multiple myeloma or a breast or prostate cancer metastasizing to the bone. In another embodiment the bone degeneration or injury may be associated with osteoporosis, osteogenesis imperfecta, or severe cranial injury. In yet another embodiment the bone injury may be a bone fracture or break.

In yet another embodiment of the present invention there is provided a method for accelerating repair of a skeletal injury in a mammal, comprising directly contacting the site of the skeletal injury with an effective amount of the osteogenic composition described herein to accelerate bone repair. In one embodiment, the method comprises recontacting the site of injury with the osteogenic composition periodically. An example of periodic recontact is about every two weeks. In one embodiment, the step of directly contacting the site of injury comprises injecting or implanting the osteogenic composition directly therein. Also, the skeletal injury may be a bone fracture or break.

In addition, the skeletal injury may be associated with osteoporosis, osteogenesis imperfecta, or severe cranial injury.

Also, the present invention also provides methods of treating bone degeneration or injury associated with a pathophysiological condition using the osteogenic compositions provided herein. The cells comprising the composition are mixed with plasma and administered into a site of bone wound or site of bone degeneration by injection or surgical implantation. If desired, cells are re-administered about every 14 days by injection. This procedure accelerates angiogenesis and bone healing faster than untreated MSCs.

Based upon the present disclosure, MSCs can be isolated and expanded in culture in vitro to obtain sufficient numbers of cells for use in the methods described herein provided that the MSCs are cultured in a manner that enhances Wnt signaling in the cells thereby enhancing osteogenic characteristic of the cell. For example, MSCs can be isolated from human bone marrow and cultured in complete medium (DMEM low glucose containing 4 mM L-glutamine, 10% FBS, and 1% penicillin/streptomycin) in hanging drops or on non-adherent dishes. However, the invention should in no way be construed to be limited to any one method of isolating and culturing medium. Rather, any method of isolating and culturing medium should be construed to be included in the present invention provided that the MSCs are cultured in a manner that promotes Wnt signaling in the cell thereby enhancing osteogenic characteristic of the cell.

Any medium capable of supporting MSCs in vitro may be used to culture the MSCs. Media formulations that can support the growth of MSCs include, but are not limited to, Dulbecco's Modified Eagle's Medium (DMEM), alpha modified Minimal Essential Medium (alphaMEM), and Roswell Park Memorial Institute Media 1640 (RPMI Media 1640) and the like. Typically, 0 to 20% fetal bovine serum (FBS) or 1-20% horse serum is added to the above medium in order to support the growth of MSCs. However, a defined medium can also be used if the growth factors, cytokines, and hormones necessary for culturing MSCs are provided at appropriate concentrations in the medium. Media useful in the methods of the invention may contain one or more compounds of interest, including but not limited to antibiotics, mitogenic or differentiation compounds useful for the culturing of MSCs. The cells may be grown at temperatures between 27° C. to 40° C., preferably 31° C. to 37° C., and more preferably in a humidified incubator. The carbon dioxide content may be maintained between 2% to 10% and the oxygen content may be maintained between 1% and 22%. However, the invention should in no way be construed to be limited to any one method of isolating and culturing MSCs. Rather, any method of isolating and culturing MSCs should be construed to be included in the present invention provided that Wnt signaling is enhanced in the cells.

Another embodiment of the present invention encompasses the route of administering MSCs to the recipient of the transplant. MSCs can be administered by a route which is suitable for the placement of the transplant, i.e. a biocompatible lattice or a donor tissue, organ or cell, to be transplanted. MSCs can be administered systemically, i.e., parenterally, by intravenous injection or can be targeted to a particular tissue or organ, such as bone marrow. MSCs can be administered via a subcutaneous implantation of cells or by injection of the cells into connective tissue, for example, muscle.

The cells of the invention may be administered into a host in order in a wide variety of ways. Preferred modes of administration are parenteral, intraperitoneal, intravenous, intradermal, epidural, intraspinal, intrasternal, intra-articular, intra-synovial, intrathecal, intra-arterial, intracardiac, intramuscular, intranasal, subcutaneous, intraorbital, intracapsular, topical, transdermal patch, via rectal, vaginal or urethral administration including via suppository, percutaneous, nasal spray, surgical implant, internal surgical paint, infusion pump, or via catheter. In one embodiment, the agent and carrier are administered in a slow release formulation such as a direct tissue injection or bolus, implant, microparticle, microsphere, nanoparticle or nanosphere. MSCs can be suspended in an appropriate diluent. Suitable excipients for injection solutions are those that are biologically and physiologically compatible with the MSCs and with the recipient, such as buffered saline solution or other suitable excipients. The composition for administration can be formulated, produced and stored according to standard methods complying with proper sterility and stability.

The dosage of the MSCs varies within wide limits and may be adjusted to the individual requirements in each particular case. The number of cells used depends on the weight and condition of the recipient, the number and/or frequency of administrations, and other variables known to those of skill in the art.

The cells described herein can be used in combination with any known technique of tissue engineering, including but not limited to those technologies described in patents and publications including U.S. Pat. Nos. 5,902,741 and 5,863,531 as well as, but not limited to U.S. Pat. No. 6,139,574; U.S. Pat. No. 5,759,830; U.S. Pat. No. 5,741,685; U.S. Pat. No. 5,736,372; U.S. Pat. No. 5,804,178; U.S. Pat. No. 5,770,417; U.S. Pat. No. 5,770,193; U.S. Pat. No. 5,709,854; U.S. Pat. No. 5,516,532; U.S. Pat. No. 5,855,610; U.S. Pat. No. 5,041,138; U.S. Pat. No. 6,027,744; U.S. Pat. No. 6,123,727; U.S. Pat. No. 5,536,656; U.S. Pat. No. 5,144,016; U.S. Pat. No. 5,944,754; U.S. Pat. No. 5,723,331; U.S. Pat. No. 6,143,501; all of which are incorporated herein by reference in their entirety.

Transplantation. The invention provides an osteogenic composition comprising MSCs pre-cultured in the presence of an agent that accelerates canonical Wnt signaling therein. In using the osteogenic compositions of the invention, one of ordinary skill in this art is well able to formulate the composition with a suitable pharmaceutical carrier, if necessary, for injection or implantation and to determine whether injection or implantation is the most effective means of introducing the osteogenic composition to the site of bone degeneration or injury. Also, one of ordinary skill in the art is well able to determine a sufficient dosage of the osteogenic composition to inject or implant into a mammal. Dosage would be based on at least the location, extent and severity of bone degeneration or injury and on the pathophysiological condition associated therewith.

Embodiments described encompass methods for administering cells of the invention to an animal, including a human, in order to treat a disease where the introduction of new, undamaged cells will provide some form of therapeutic relief.

The skilled artisan will readily understand that MSCs can be transplanted into a recipient whereby upon receiving signals and cues from the surrounding milieu, the cells can further differentiate into mature cells in vivo dictated by the neighboring cellular milieu. Alternatively, the MSCs can be differentiated in vitro into a desired cell type and the differentiated cell can be administered to an animal in need thereof.

The invention also encompasses grafting MSCs in combination with other therapeutic procedures to treat disease or trauma in the body. Thus, MSCs can be co-grafted with other cells, both genetically modified and non-genetically modified cells which exert beneficial effects on the patient. Therefore the methods disclosed herein can be combined with other therapeutic procedures as would be understood by one skilled in the art once armed with the teachings provided herein.

The MSCs of this invention can be transplanted into a patient using techniques known in the art such as i.e., those described in U.S. Pat. Nos. 5,082,670 and 5,618,531, each incorporated herein by reference, or into any other suitable site in the body.

Transplantation of the cells of the present invention can be accomplished using techniques well known in the art as well as those described herein or as developed in the future. The present invention comprises a method for transplanting, grafting, infusing, or otherwise introducing the cells into a mammal, preferably, a human. Exemplified herein are methods for transplanting the cells into bone tissue of various mammals, but the present invention is not limited to such anatomical sites or to those mammals. Also, methods that relate to bone transplants are well known in the art and are described for example, in U.S. Pat. No. 4,678,470 and U.S. Pat. No. 5,571,083, teaches methods for transplanting cells to any anatomical location in the body.

The cells may also be encapsulated and used to deliver biologically active molecules, according to known encapsulation technologies, including microencapsulation (see, e.g., U.S. Pat. Nos. 4,352,883; 4,353,888; and 5,084,350, herein incorporated by reference), or macroencapsulation (see, e.g., U.S. Pat. Nos. 5,284,761; 5,158,881; 4,976,859; and 4,968,733; and International Publication Nos. WO 92/19195; WO 95/05452, all of which are incorporated herein by reference). For macroencapsulation, cell number in the devices can be varied; preferably, each device contains between $10^3$ to $10^9$ cells, most preferably, about $10^5$ to $10^7$ cells. Several macroencapsulation devices may be implanted in the patient. Methods for the macroencapsulation and implantation of cells are well known in the art and are described in, for example, U.S. Pat. No. 6,498,018.

The dosage of the MSCs varies within wide limits and may be adjusted to the individual requirements in each particular case. The number of cells used depends on the weight and condition of the recipient, the number and/or frequency of administration, and other variables known to those of skill in the art.

The number of MSCs administered to a patient may be related to, for example, the cell yield after processing. A portion of the total number of cells may be retained for later use or cyropreserved. In addition, the dose delivered depends on the route of delivery of the cells to the patient. In one embodiment of the invention, a number of cells to be delivered to the patient is expected to be about $5.5 \times 10^4$ cells or greater. However, this number can be adjusted by orders of magnitude to achieve the desired therapeutic effect.

The mode of administration of the cells of the invention to the patient may vary depending on several factors including the type of disease being treated, the age of the mammal, whether the cells are differentiated or not, whether the cells have heterologous DNA introduced therein, and the like. The cells may be introduced to the desired site by direct injection, or by any other means used in the art for the introduction of compounds administered to a patient suffering from a particular disease or disorder.

The MSCs may also be applied with additives to enhance, control, or otherwise direct the intended therapeutic effect. For example, in one embodiment, the cells may be further purified by use of antibody-mediated positive and/or negative cell selection to enrich the cell population to increase efficacy, reduce morbidity, or to facilitate ease of the procedure. Similarly, cells may be applied with a biocompatible matrix which facilitates in vivo tissue engineering by supporting and/or directing the fate of the implanted cells.

Prior to the administration of the MSCs into a patient, the cells may be stably or transiently transfected or transduced with a nucleic acid of interest using a plasmid, viral or alternative vector strategy. The cells may be administered following genetic manipulation such that they express gene products that intended to promote the therapeutic response (s) provided by the cells.

The use of MSCs for the treatment of a disease, disorder, or a condition provides an additional advantage in that the MSCs can be introduced into a recipient without the requirement of an immunosuppressive agent. Successful transplantation of a cell is believed to require the permanent engraftment of the donor cell without inducing a graft rejection immune response generated by the recipient. Typically, in order to prevent a host rejection response, nonspecific immunosuppressive agents such as cyclosporine, methotrexate, steroids and FK506 are used. These agents are administered on a daily basis and if administration is stopped, graft rejection usually results. However, an undesirable consequence in using nonspecific immunosuppressive agents is that they function by suppressing all embodiments of the immune response (general immune suppression), thereby greatly increasing a recipient's susceptibility to infection and other diseases.

The present invention provides a method of treating a disease, disorder, or a condition of bone by introducing MSCs or differentiated MSCs of the invention into the recipient without the requirement of immunosuppressive agents. The present invention includes the administration of an allogeneic or a xenogeneic MSCs, or otherwise an MSC that is genetically disparate from the recipient, into a recipient to provide a benefit to the recipient. The present invention provides a method of using MSCs or differentiated MSCs of the invention to treat a disease, disorder or condition without the requirement of using immunosuppressive agents when administering the cells to a recipient. There is therefore a reduced susceptibility for the recipient of the transplanted MSC or differentiated MSC of the invention to incur infection and other diseases, including cancer relating conditions that is associated with immunosuppression therapy.

The following further illustrate various representative embodiments. However, they are in no way a limitation of the teachings or disclosure of the present invention as set forth herein. The invention is now described with reference to the following Examples. These Examples are provided for the purpose of illustration only, and the invention is not limited to these Examples, but rather encompasses all variations which are evident as a result of the teachings provided herein.

To investigate the role of Wnt signaling and osteogenesis by human MSCs. An inhibitor of GSK3β that would be predicted to mimic Wnt signaling through direct stabilization of β-catenin (bromo-indirubin-3'-mono-oxime, BIO) and an inhibitor of PPARγ (GW9662, or GW) that would be predicted to attenuate inhibitory crosstalk from the adipogenic axis and therefore also enhance Wnt signaling (Farmer, 2005, Int J Obes (Lond). 29:13-16; Akune et al., 2004, J Clin Invest 113:846-855; Liu et al., 2004, J Biol Chem 279:45020-45027) were compared. It was observed that both BIO and GW increased in vitro mineralization, but expression of early osteogenic markers was biphasic, with higher doses becoming inhibitory. When implanted into mice harboring calvarial defects, hMSCs pre-treated with GW substantially accelerated healing. It was observed that GW treatment significantly reduced expression of chemokines that may exacerbate neutrophil and macrophage mediated cell rejection. These data suggest that use of PPARγ inhibitors during the preparation of hMSCs substantially and reliably enhances the capacity of hMSCs for osteogenic cytotherapy.

Example 1

Pharmaceutical Modulation of Canonical Wnt Signaling in Multipotent Stromal Cells for Improved Osteoinductive Therapy Human mesenchymal stem cells (hMSCs) from bone marrow are regarded as putative osteoblast progenitors in vivo and differentiate into osteoblasts in vitro. Positive signaling by the canonical wingless (Wnt) pathway is critical for the differentiation of MSCs into osteoblasts. In contrast, activation of the peroxisome proliferator-activated receptor-γ (PPARγ) mediated pathway results in adipogenesis. Experiments were designed to compare the effects of glycogen-synthetase-kinase-βp (GSK3β) inhibitors and PPARγ inhibitors on osteogenesis by hMSCs. Both compounds altered the intracellular distribution of β-catenin and GSK3r3 in a manner consistent with activation of Wnt signaling. With osteogenic supplements, the GSK3β inhibitor bromoindirubin-3'-monooxime (BIO) and the PPARγ inhibitor GW9662 (GW) enhanced early osteogenic markers, alkaline phosphatase (ALP) and osteoprotegerin (OPG) by hMSCs and transcriptome analysis demonstrated upregulation of genes encoding bone-related structural proteins. At higher doses of the inhibitors, ALP levels were attenuated, but dexamethasone-induced biomineralization was accelerated. When hMSCs were pretreated with BIO or GW and implanted into experimentally induced non-self healing calvarial defects, GW treatment substantially increased the capacity of the cells to repair the bone lesion. Furthermore, it was observed that GW treatment significantly reduced expression of chemokines that may exacerbate neutrophil and macrophage mediated cell rejection. These data suggest that use of PPARγ inhibitors during the preparation of hMSCs may enhance the capacity of the cells for osteogenic cytotherapy.

The materials and methods employed in further examples disclosed herein are described below.

Tissue culture. Iliac crest bone marrow aspirates (2 mL) were drawn in accordance with institutional review board approval. Mesenchymal stem cells were prepared from the mononuclear fraction of the aspirates as previously described (Colter et al., 2000, Proc Natl Acad Sci USA 96:7294-7299; Sekiya et al., 2002, Stem Cells 20:530-541).

Human MSCs were cultured in a-MEM containing 20% (vol/vol) FBS, 100 units·mL$^{-1}$ penicillin, 1 µg·mL$^{-1}$ streptomycin, and 4 mM L-glutamine. For expansion, cells were plated at an initial seeding density of 100 cells/cm$^2$ and allowed to divide for six to eight doublings until 40-50% confluent. For repassage and experiments, MSCs were recovered with trypsin/EDTA mixture.

Early osteogenic differentiation and alkaline phosphatase assays. MSCs were plated in 6-well plates at an initial plating density of 100 cells per cm$^2$ and cultured in standard complete media for 6 days until semi-confluence (approximately 5,000 cells per cm$^2$). Osteogenic base media consisting of complete media containing 5 mM β-GP and 50 µg mL$^{-1}$ ascorbate-2-phosphate and the appropriate inhibitor or vehicle was then used to induce early osteogenic differentiation. Assays were allowed to proceed for 8-10 days with changes of media every 2 days. ALP assays were performed as previously described (Gunn et al., 2006, Stem Cells 24:986-991).

Cell cycle. Profiles were generated by fluorescence activated cell sorting and analyzed with software.

Array analysis. Transcriptome arrays were performed using Affimetrix apparatus and HG-U133 Plus 2.0 chips. Cytokine arrays on conditioned media were performed using a human cytokine array and analyzed using a digital imager.

ELISAs. ELISA for CXCL6, Dkk-1, GROa, GRO13, and OPG were carried out by using nonbiotinylated polyclonal capture antibodies and biotinylated detection antibodies that were commercially acquired on coated 96-well plates The biotinylated capture antibodies were detected by using horseradish peroxidase-conjugated streptavidin and TMB substrate. ELISA for IL-lb were performed by using commercially acquired kits.

Protein extraction, gel electrophoresis and western blotting. Nuclear extracts were performed by Triton extraction and differential centrifugation as previously described (Gregory et al., 2003, J Biol Chem 278:2806728078). Proteins were electrophoresed and blotted onto nitrocellulose using an electrophoresis system.

Late stage osteogenesis and ARS staining. Mature osteogenic assays were performed in 6 well format as previously described (Gregory et al., 2004, Anal Biochem 329:77-84).

Clotted plasma co-culture. Confluent monolayers of MSCs were generated in wells of a 12 well tissue culture plate. Human plasma was added to each well so as to cover approximately 30% of the surface area. After the plasma had clotted osteogenic assays were then performed using standard media preparations.

Calvarial lesions. MSCs were cultured in the presence of osteogenic base media containing the appropriate inhibitor or vehicle. After 8 days, they were suspended in human plasma and administered to nude mice that had received a circular lesion in the cranium. Subsequent doses of cells were administered by direct injection in plasma/thromboplastin mix.

X-ray imaging and quantification. Cranial bones were imaged by x-ray under anaesthesia. Digital images were be captured on a digital plate and processed on a phosphorimager reader and processed by volume analysis software.

Histochemistry and immunocytochemistry. For β-catenin localization studies, hMSCs were stained with a cy-3 conjugated anti-β-catenin antibody and nuclei were counterstained with pico-green dye. Specimens were processed as paraffin blocks and 8 longitudinal sections were prepared, deparaffinized and rehydrated, then stained with hematoxylin and eosin. For immunocytochemistry, sections were probed with an anti-human β-2-microglobulin antibody. An upright fluorescent microscope fitted with a high performance camera (and image analysis software was employed for imaging.

Tetracycline tracing of in vivo calcium deposition. The tetracycline was imaged using an upright fluorescent microscope fitted with a high performance camera and analyzed using software. Embedding, sectioning and mounting was carried out on non-decalcified material.

Semi-quantitative blood vessel measurements. Calvaria were fixed, decalcified and sectioned in paraffin and stained with hematoxylin and eosin as described. Using NIS-Elements image analysis software, the surface area of blood vessels in a defined ROI was calculated and totaled. The values were expressed as the mean of total blood vessel area from 3 animals per group.

Calvaria were fixed, decalcified, and sectioned in paraffin and stained with hematoxylin and eosin as described. Two-dimensional regions of interest (ROI) were carefully defined and normalized for all specimens. For this purpose, 6 µm-thick longitudinal serial sections were prepared, and those sections containing tissue up to and including 0.5 mm above and below the diameter of the lesion. These were included in the measurements. A 6 µm section was counted every 30 µm (34 sections) within the entire region of interest, which consisted of the longitudinal thickness of the lesion (the thickness of the bone and adjacent fibrous tissue) by the original width of the lesion in one dimension (3 mm) and 0.5 mm above and below the original diameter of the lesion in the final dimension. Using NIS-Elements image analysis software, the surface area of blood vessels in the 2D ROI was calculated for each section and totaled. The values were expressed as the mean of total blood vessel area from three animals per group.

The results of these experiments are now described.

Figure 15:
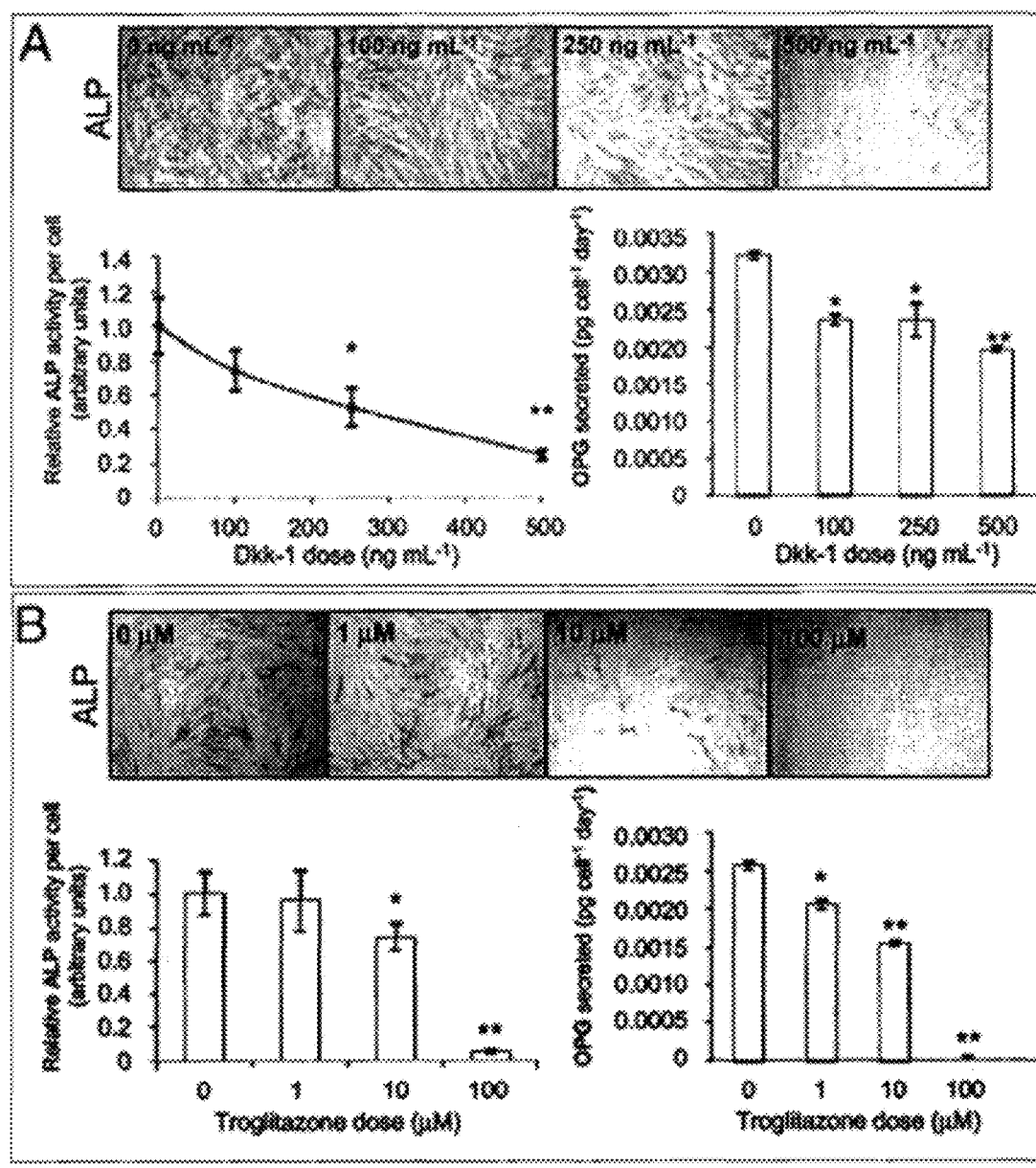
FIG. 15 comprising
Figure 16:
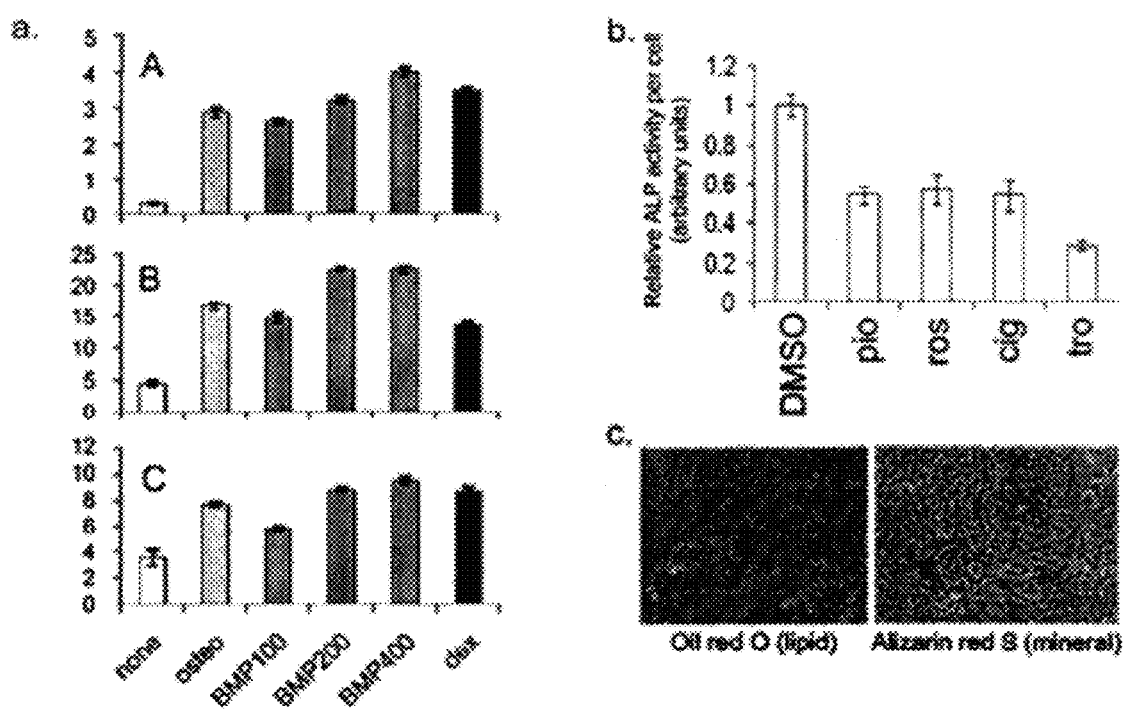
FIGS. 16A-16C depict a series of illustrations depicting the effects of β-glycerophosphate and ascorbic acid, BMP2, dexamethasone (dex), and various agonists on osteogenesis.

Effect of Dkk-1 and PPARγ agonists on the expression of ALP. To confirm that Wnt signaling is necessary for the differentiation of hMSCs into osteoblasts, MSCs were incubated in osteoinductive media containing no dexamethasone (dex), for 8 days and measured activity of alkaline phosphatase (ALP). Although it is conventional to add dexamethasone for osteogenesis, given its powerful pleiotropic effects and the observation that early osteogenic markers such as ALP can be activated without its presence (FIG. 16A), initial experiments were performed in the absence of dexamethasone. When the Wnt inhibitor Dldc-1 was added to block canonical Wnt signaling, ALP activity was attenuated (FIG. 15A). PPARγ activity was examined on osteogenesis since the PPARγ activity enhances adipogenesis whilst inhibiting the Wnt mediated osteogenic axis of differentiation (Boland et al., 2004, J Cell Biochem 93:1210-30; Farmer, 2005, Int J Obes (Lond). 29:13-16). ALP function was dose-dependently down-regulated upon incubation with troglitazone, and also other synthetic PPARγ agonists (FIG. 15B, FIG. 16).

Figure 17:
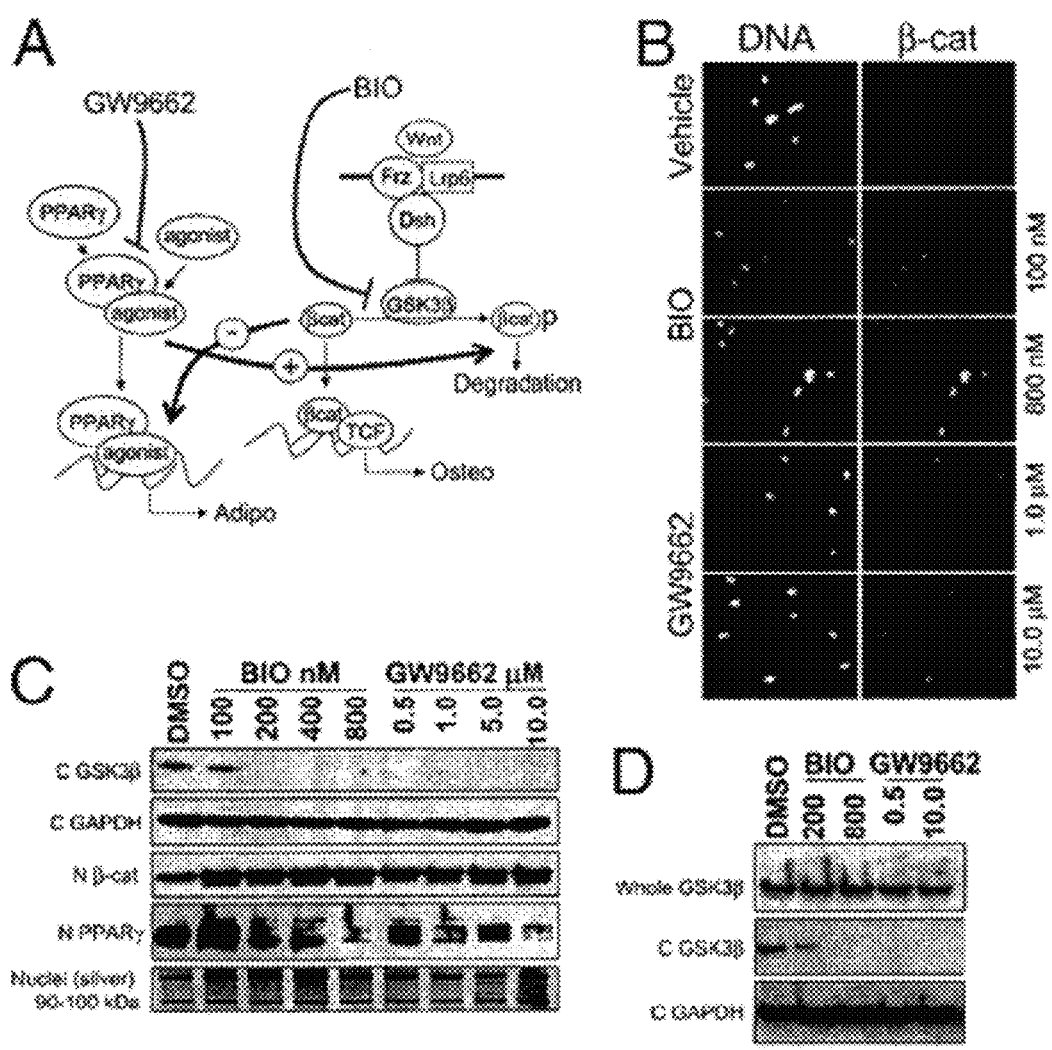
FIG. 17, comprising

Effect of GSK3β and PPARγ inhibition on intracellular redistribution of GSK3β and β-catenin. The next experiments were designed to examine whether inhibition of GSK3β would mimic Wnt signaling through direct stabilization of β-catenin, and inhibition of PPARγ that would blunt inhibitory crosstalk from the adipogenic axis therefore also resulting in enhancement Wnt signaling (FIG. 3A) (Farmer, 2005, Int J Obes (Lond). 29:13-16; Akune et al., 2004, J Clin Invest 113:846-855; Liu et al., 2004, J Biol Chem 279:45020-45027). The inhibitors BIO and GW were chosen due to their specificity for GSK3β and PPARγ respectively (FIG. 17A). Incubation of both inhibitors with MSCs under osteogenic conditions resulted in increased levels of nuclear β-catenin (FIG. 17B, 17C) and depletion of GSK3β from the cytoplasm (FIG. 17D). Interestingly, cytosolic depletion of GSKβ occurred, even though the proposed mechanism of BIO or GW does not predict up-regulation of a Wnt/Frz/LRP/Dsh receptor complex. Without wishing to be bound by any particular theory, both nuclear localization of β-catenin and depletion of cytosolic GSK3β are consistent with enhancement of canonical Wnt signaling. Furthermore, incubation of hMSCs in either BIO or GW reduced nuclear levels of PPARγ, also suggesting that the canonical Wnt axis was predominating in the treated cells.

Figure 18:
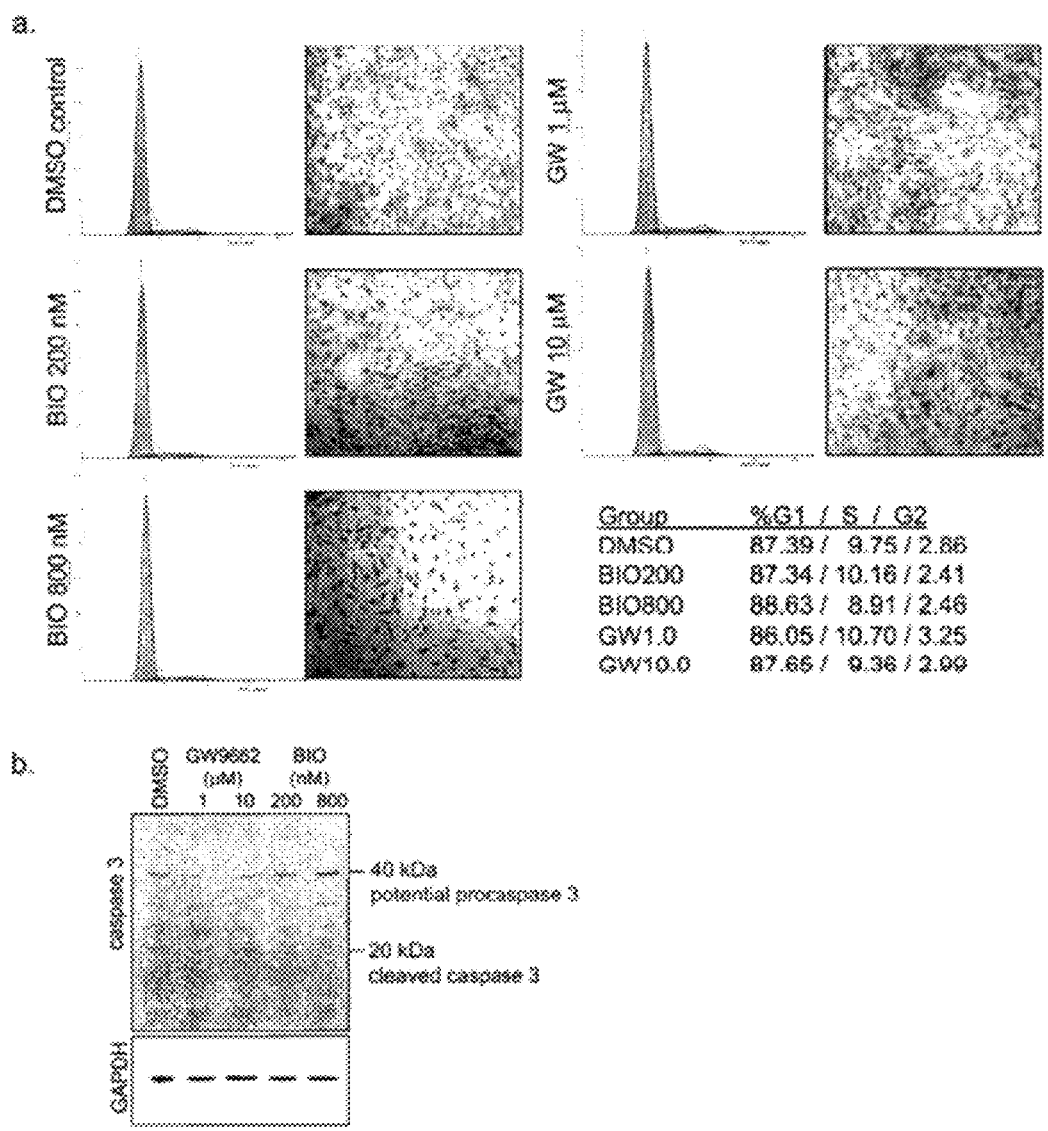
FIG. 18 comprising
Figure 19:
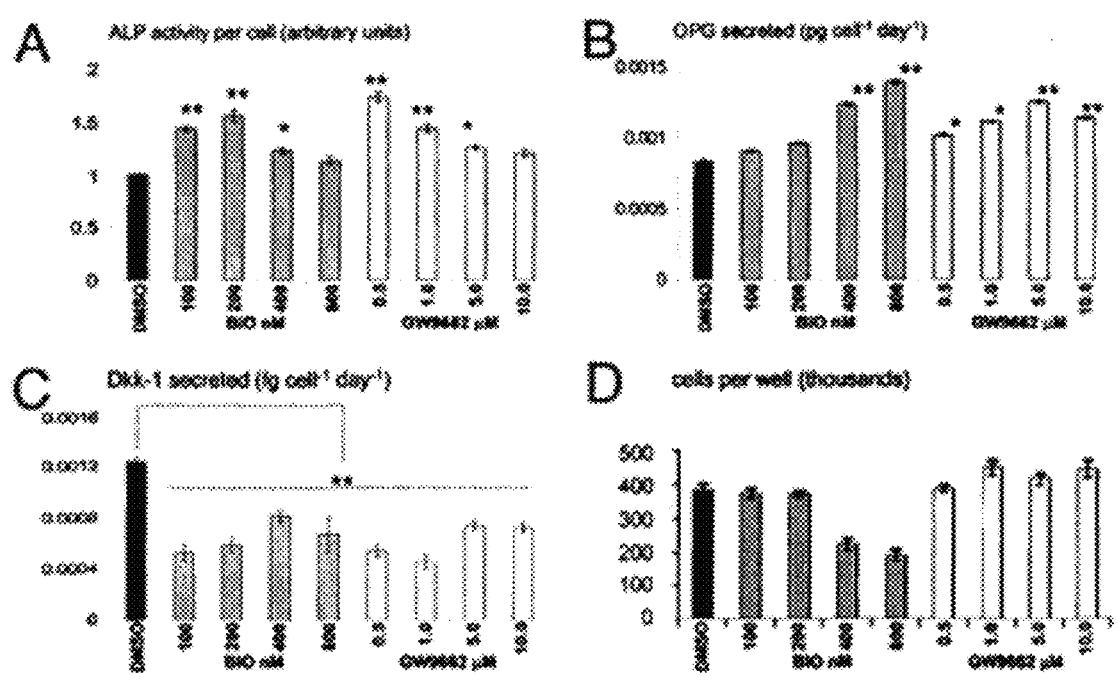
FIG. 19 comprising

Effect of GSK3β and PPARγ inhibition on the expression of ALP, OPG and Dkk-1. To examine whether the up-regulation of Wnt signaling by the inhibitors affected early stage osteogenesis by MSCs, they were incubated in osteogenic medium lacking dex but containing BIO or GW. After 8 days of culture, ALP activity and the secretion of OPG were measured. Both inhibitors induced the ALP activity, but this was observed at low doses of inhibitor; in the case of BIO, the maximal effect was observed between 100-200 nM and for GW, the effect occurred at doses between 0.5 and 1.0 μM. At higher doses, exceeding 400 nM BIO or 1.0 μM GW, ALP activity dropped back to control levels (FIG. 19A). Secretion of OPG rose in a dose dependent manner upon incubation with BIO, but reached maximal stimulation at 0.5 μM GW (FIG. 19B). It has been speculated that arrest of canonical Wnt signaling occurs during terminal differentiation of osteoprogenitor cells and Dkk-1 has been implicated in this process (van der Horst et al., 2005, J Bone Miner Res 20:1867-1877; Liu et al., 2009, J Cell Biol 185:67-75). Dkk-1 secretion was reduced in all cases, with maximal inhibition occurring at concentrations that induced highest ALP activity (FIG. 19C). Even though Dkk-1 levels were slightly elevated GW and BIO doses, they remained significantly lower than the control. A substantial reduction of hMSC yield was evident when exposed to concentrations greater than 400 nM of BIO. This effect did not seem to arise from canonical Wnt signaling since GW elicited the same effects on β-catenin, GSK3β redistribution and stimulation of early osteogenic markers without reduction in cellular yield. Although BIO is highly specific for GSK3P, (Meijer et al., 2003, Chem Biol 10:1255-1266) the parent molecule; indirubin monooxime has been shown to inhibit cyclin dependent kinases at high concentrations (Damiens et al., 2001, Oncogene 20:3786-3797). Cell cycle analysis demonstrated that hMSCs treated with 800 nM BIO exhibited a similar DNA profile to those that are heavily contact inhibited, suggesting that high doses of BIO inhibit mitosis (FIG. 18A). The absence of apoptotic morphology, a pre-G1 peak (FIG. 18B) and no detectable levels of cleaved caspase 3 confirmed apoptosis was also not responsible for the reduced cell yield.

Effects of GSK3β and PPARγ inhibition on the transcriptome of hMSCs. Inhibition of GSK3β and PPARγ appeared to increase the level of Wnt signaling concomitantly with increased OPG secretion and ALP activity. These observations suggested that inhibitors had enhanced the early stages of osteogenesis through acceleration of canonical Wnt signaling at the expense of PPARγ activity. To examine this in more detail, hMSCs were incubated in osteogenic media lacking dex, but containing high (800 nM BIO and 10 μM GW) and low (200 nM BIO and 1.0 μM GW) doses of the inhibitors. After 8 days of culture, RNA microarrays were performed on the hMSCs. Initial inspection of the datasets demonstrated that they shared similarities with a study involving human fibroblasts and Wnt3a suggesting that canonical Wnt signaling had been accelerated. It was observed that Klf-6, caldesmon-1, gamma-aminobutyric acid B receptor-2, synaptotagmin like-2 were significantly up-regulated in Wnt3a treated fibroblasts and both BIO and GW treated hMSCs. Protocadherin-7, PR domain containing-1, gremlin-1, collectin subfamily member-12, stanniocalcin-2 were significantly up-regulated in Wnt3a treated fibroblasts and BIO treated hMSCs only (GW, no change). Fibroblast growth factor-7, high mobility group AT-hook 2, Cdk5 and Abl enzyme substrate-1, amyloid beta precursor protein-binding family B2 were significantly up-regulated in Wnt3a treated fibroblasts GW treated hMSCs only (BIO, no change). Transducin-like enhancer of split-1 was significantly up-regulated in Wnt3a treated fibroblasts but down-regulated in both BIO- and GW treated hMSCs.

Figure 20:
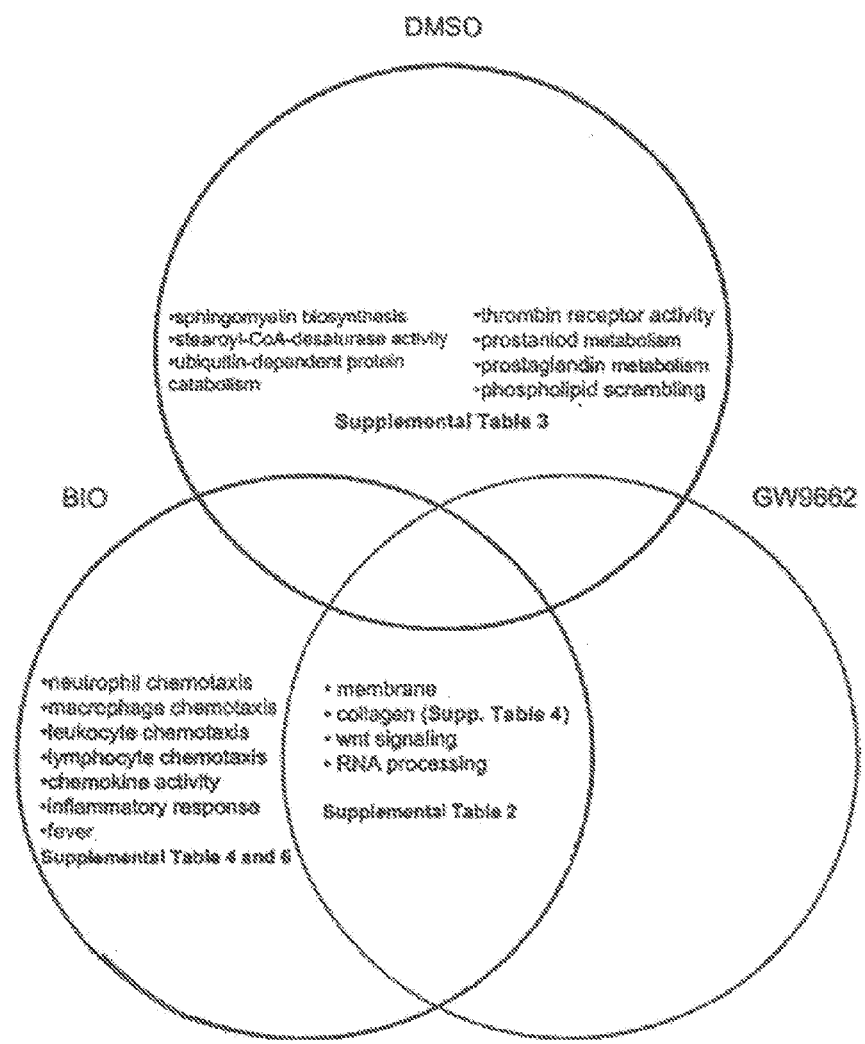
FIG. 20 is a Venn diagram summarizing the major microarray analysis results. Human MSCs were treated with 200 or 800 nM BIO or 1.0 or 10.0 p.M GW9662 in osteogenic media for 8 days. RNA was then extracted and subjected to Affimetrix microarray analysis. Results were subjected to hierarchical clustering, and three main clusters were evident—up-regulated in GW9662 and BIO when compared to controls, up-regulated in control cells when compared to BIO and GW9662 groups, and profoundly down-regulated in GW9662 treated cells, but modestly up-regulated in BIO-treated cells when compared to controls. The genes within each cluster were then sorted based on their gene ontology tags (GO tags). The Venn diagram represents the clusters, and the text represents the major GO tag designations within the clusters. Details are presented in supplemental tables. Note that the P values for the clustering were extremely low (in the order of $1\times10^{-6}$ to $1\times10^{-100}$) demonstrating that the probability of a given set of genes clustering due to random occurrence was virtually zero.

Irrespective of dose, differentially transcribed genes clustered into 2 general groups with strong statistical significance (p<0.0001 for all cases, FIG. 20); up-regulated in GW and BIO treated cells compared to the vehicle control (I) and up-regulated in the vehicle control compared to BIO and GW (II). Gene clusters were sorted into gene ontology (GO) tags based on known function. The majority of GO tags in cluster I (FIG. 35) consisted of membrane, mRNA processing, and intracellular rearrangement-related functions as well as collagen and extracellular matrix (ECM) groups. The Wnt/13-catenin GO group was also significantly represented in this cluster. Upon examination of individual fold-changes for differentially expressed ECM genes it was evident that collagens and ECM proteins found in bone tissue were up-regulated whereas those found in other tissues were reduced or unchanged (FIG. 38). Of interest was the downregulation of matrix metalloproteinase I, matrix gla-protein and oncostatin M, all associated with inhibition of osteogenesis or bone catabolism. Cluster II consisted mainly of genes responsible for steroid and lipid processing (FIG. 37). Of note was the prevalence of prostaglandin and lipid modifying enzymes in this cluster because these processes often provide ligands for PPARγ (Kota et al., 2005, Pharmacol Res 51:85-94) as well as enrichment of sphingomyelin and ceramide related genes, which are strongly associated with lipid and steroid homeostasis (Lucki et al., 2008, Subcell Biochem 49:387-412; Worgall, 2008, Subcell Biochem 49:371-385).

Effect of GSK3β and PPARγ inhibition on late stage osteogenesis. Extended periods of incubation in BIO and GW in the absence of dex did not induce biomineralization, so therefore experiments were designed to measure the effect of the inhibitors in its presence. Initially, experiments were conducted to examine whether pre-treatment of hMSCs with inhibitors BIO (200 and 800 nM) and GW (1.0 and 10.0 µM) in the presence of β-glycerophosphate (β-GP) and ascorbate for 8 days followed by 15 days in the same media supplemented with dex affected mineralization of the cultures. If BIO or GW function to accelerate the cells through the immature stages of osteogenesis and partially to maturity, hMSCs exposed to these conditions would be expected to respond more rapidly to the steroid-dependent mature osteoblast transition. After differentiation, calcium content was visualized by Alizarin Red S (ARS) staining and the dye was extracted and quantified. At the doses tested, and in a dose-dependent manner, BIO and GW enhanced dex-induced differentiation into biomineralizing osteoblasts (FIG. 21).

Figure 22:
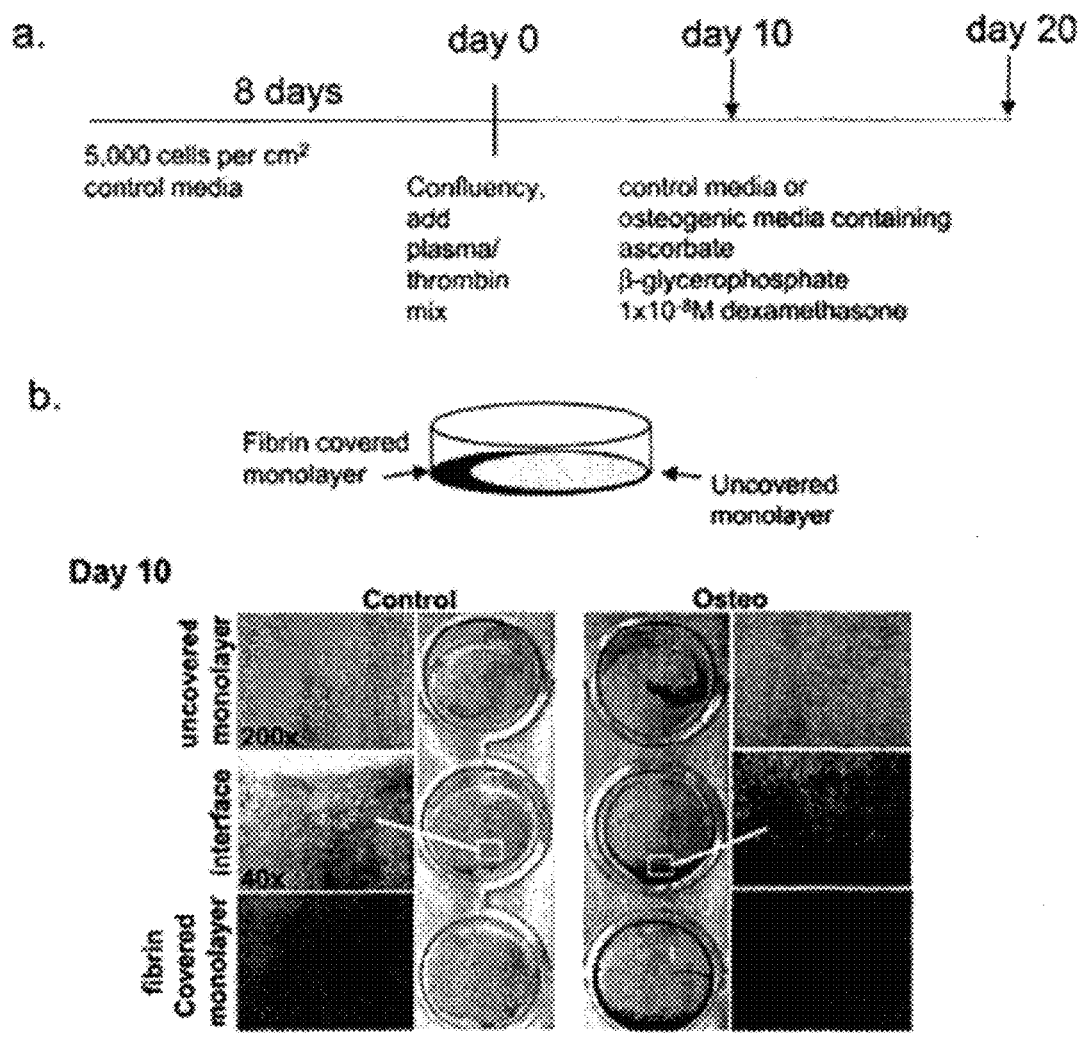
FIG. 22 comprising

The next experiments were performed to examine whether withdrawal of the Wnt stimulus caused by BIO and GW was necessary for the hMSCs to progress to a dex-dependent biomineralizing phenotype. Human MSCs were pre-cultured with BIO and GW in the presence of β-GP, ascorbate and dex for 17 days. Once again, inhibitor treatment enhanced dex-induced biomineralization (FIG. 23) suggesting that the action of BIO and GW enhances the early stages of osteogenesis and removal of the stimulus is not required to complete the process. Data from both experiments suggest that Wnt modulation is necessary to induce an early osteoprogenitor-like phenotype in hMSCs and this process can occur simultaneously with terminal differentiation. Clotted human plasma is a biocompatible and osteoinductive vector for administration of hMSCs In anticipation of in vivo experiments testing the potential efficacy of the inhibitor treated hMSCs for the repair of bone, a number of matrices for cell administration was examined. It was observed that clotted human plasma sustained the survival and proliferation of hMSCs in, vitro and also accelerated steroid-induced biomineralization. When monolayers of hMSCs are partially covered with a meniscus of clotted human plasma, the cells in contact with the plasma mineralize faster than the uncovered portion of the monolayer when dex-containing osteogenic media is provided (FIG. 22).

Effects of GSKβ and PPARγ inhibition on repair of an induced cranial defect in mice. Given that BIO and GW accelerated osteogenic differentiation by human MSCs in vitro, experiments were conducted to test whether the treated hMSCs could repair a critical bone defect in vivo. Human MSCs were cultured in the presence of osteogenic medium lacking dex, but containing BIO (200 and 800 nM) or GW (1.0 and 10.0 µM). Calvarial lesions were generated in nude mice and $1 \times 10^6$ hMSCs, mixed with human plasma were applied followed by thromboplastin to initiate gelling. The scalp was sutured and the animals were allowed to heal. Initially, short-duration experiments were performed to monitor distribution of the hMSCs, and to ensure the cells had survived the implantation process. GFP-labeled hMSCs were administered and mice were sacrificed after 24 h. Upon histological analysis, a substantial number of GFP-labeled, healthy hMSCs had formed a thick layer over the injury and adjacent bone tissue (FIG. 24A, 24B). The hMSCs could be readily detected with an antibody for membrane localized human β-2 microglobulin (FIG. 24C, 24D). Robust antibody-detection of unmanipulated hMSCs, rather than lentiviral labeling was favored in long term experiments because very low passage hMSCs could be utilized, rather than genetically tagged preparations that had undergone a number of passages. Long term experiments were performed for 50 days with further doses of hMSCs administered at day 14, 28 and 42 by direct injection of a plasma:hMSC mixture under the scalp (FIG. 25A). At day 50, the crania were explanted and x-ray images of the calvarial lesions were taken. The digitized images were then analysed densitometrically to quantify the degree of bone accrual (FIG. 25B). The lesioned side was compared with the contralateral side and data were expressed as the ratio of radio-opacity on the lesioned side to the contralateral side. Surprisingly, GW, significantly improved the ability of MSCs to repair cranial lesions when compared to MSCs that were not drug treated. Upon histological analysis, new bone formation was detected in the GW groups and in the case of the 1011M GW group, marrow sinusoids were evident in the newly formed bone (FIG. 27A) which could be identified by tetracycline incorporation (FIG. 27B). In contrast, there was no significant sign of bone repair in the mock groups that received plasma alone, and control hMSC groups, that received cells treated with DMSO or BIO. When the sections were stained with anti-β-2 microglobulin, isolated clusters of hMSCs from only control and GW groups were detected (FIGS. 27C and 27D). However, no more than a few hundred cells could be counted throughout the entire lesion, suggesting that the majority of cells had either died or migrated away. In both control groups and in the GW treated groups, blood vessels were detected, demonstrating that GW treatment had not affected the ability of MSCs to initiate angiogenesis at trauma sites (FIG. 28A).

Enhanced compatibility of the GW-treated hMSCs for the osteogenic niche could explain the increased efficacy. However, upon further inspection of the microarray data, a minor cluster was identified where genes were profoundly down-regulated in GW-treated MSCs as compared to the control. This cluster was highly enriched for inflammatory mediators including IL1, IL8, and chemokines of the CXCL family (FIG. 39). These data could be validated by ELISA assay of supernatants from treated hMSC cultures (FIG. 40). Because nude mice are able to elicit a macrophage and neutrophil mediated response, it is probable that the GW treated MSCs were protected by reduced expression of chemoattractants.

MSCs for regenerating bone. Cultures of hMSCs are inherently heterogeneous, with the individuals of the population possessing different propensities for osteogenesis, chondrogenesis, adipogenesis or proliferation. Heterogeneity can arise from the nature of the donor, the number of past cell doublings, and cell density. Evidence suggests that the history of a given hMSC, with respect to the number of cell doublings, and past exposure to different levels of cell density can in most cases affect the propensity of a given cell to divide or differentiate (Sekiya et al., 2002, Stem Cells 20:530-541; Gregory et al., 2005, Sci STKE 294:pe37; Larson et al., 2008, Stem Cells 26, 193-201). This apparently stochastic distribution of cellular characteristics can be controlled in part by the addition of cytokines, growth factors and/or drugs. Given that both Wnt signaling and blunting of the adipogenic axis is necessary for the initiation of osteogenic processes in MSCs, experiments were designed to investigate the role of small molecule inhibitors in controlling the events. The results presented herein demonstrate that Wnt signaling could be increased in MSCs by either direct inhbition of GSK3β or by inhibiting the master regulator of adipogenesis, PPARγ. These observations supported the widespread notion that negative crosstalk occurs between the canonical Wnt and PPARγ axis, regulated in part by the transcription factor TAZ (Hong et al., 2005, Science 309: 1074-1078). At lower doses, expression of early osteogenic markers in hMSCs could be significantly enhanced by treatment with either inhibitor but this was attenuated at higher doses. In contrast, when hMSCs were pre-treated or simultaneously treated with BIO or GW, and subjected to dex-dependent osteogenesis, mineralization was upregulated in a dose-dependent manner. A simple interpretation of these results lead to the conclusion that endogenous canonical Wnt signaling can enhance osteogenesis. However, it is possible that the high-serum culture system used in the present experiments reflect a situation with modest osteogenic and adipogenic stimuli affecting a balanced steady state on the cells. The presence of GW and BIO therefore, disrupt the balance of the culture in favor of the osteogenic lineage. In contrast, high concentrations of PPARγ agonists in our osteogenic cultures containing dex initiate adipogenesis rather than osteogenesis.

When implanted into experimentally induced calvarial defects in mice, GW treated hMSCs profoundly improved healing and induced angiogenesis. Although vehicle treated hMSCs could not significantly enhance bone repair, angiogenesis was also induced suggesting that even vehicle treated hMSCs had survived at the site for a duration sufficient to initiate the process. Although the efficacy of GW treated hMSCs is probably due to enhanced osteogenic propensity and angiogenic properties, substantial down-regulation of immune-chemokines is also likely to extend their survival. In some instances, the survival of GW or BIO treated hMSCs was transient. Without wishing to be bound by any particular theory, it is believed that the transplanted cells provide a supporting role for host cells. In agreement with this observation, it has recently been demonstrated that a population of hMSCs with a enhanced endogenous canonical Wnt signaling serves to enhance synergistically the ostoegenic capacity of co-administered hMSCs with a lesser degree of Wnt signaling (Liu et al., 2009, J Cell Biol 185:67-75). hMSCs treated with GW, an inhibitor of PPARγ, had increased their osteogenic propensity without blunting viability or their ability to perform ancillary tasks such as angiogenic stimulation. The modified cultures are essentially a combination of stromal stem cells and osteoblasts, with properties of both. Therefore, hMSCs prepared in this manner are a unique and rationally designed cytotherapeutic with profoundly enhanced efficacy for bone repair.

Example 2

Novel Biocompatible Matrices for In Vivo Delivery of MSCs for Bone Repair

In the case of critical size defects, there is a need to regrow bone to reestablish stability and support in the area of injury. Current treatment involves the use of metallic implants, but this treatment sometimes carries with it serious side effects due to the foreign nature of the implant. The following experiments were designed to determine methods for the production of a biocompatible osteoinductive matrix that maintains viability and functionality when administered to the patient.

hMSCs are multipotent cells with the ability to differentiate into many cell types, including osteoblasts. These cells are usually extracted from adult bone marrow and easily expanded and differentiated in culture using established methods. The differentiation of hMSC's into osteoblasts has been shown to rely upon Wnt signaling and this information is important for their use in repairing bone. Secreted extracellular matrix (ECM) can be extracted from hMSC cultures that have been induced to differentiate into osteoblasts. Furthermore hMSC's can be successfully co-cultured with the extracted matrix and induced to become osteoblasts. Treatment with the Wnt-modulator, 7AIPM, was found to have increased osteoinductive characteristics.

The materials and methods employed in the experiments disclosed herein are now described. hMSCs from two different donors. This was done by growing hMSC's isolated from adult bone marrow as a monolayer on 15 cm dishes in complete culture medium (CCM) consisting of 80% a-minimal essential medium, 20% fetal bovine serum (FBS), 2 mM L-glutamine, 100 U/mL Penicillin, and 100 µg/mL Streptomycin. The dishes were kept at 37° C. and media changes were performed 3 times a week. After one week, the media was switch to an osteogenic media that is composed of CCM plus 5 mM β-glycerol phosphate, 50 µg/mL ascorbate-2-phosphate, and 1 nM dexamethasone. Cells were allowed to continue to grow for 3 or 6 additional weeks with media changes as described elsewhere herein. The ECM secreted by the hMSC's was then scraped off the culture dishes and extracted as set forth in FIG. 29.

The next experiments were designed to measure cell viability and differentiation ability of co-cultured hMSCs (e.g., GFP hMSCs) with the matrices collected elsewhere herein. Briefly, a total of 4 samples treated with trypsin and 5 untreated samples of matrix were placed in round bottom tubes. The GFP hMSCs were cultured as stated before for approximately 10 days. These cells were then washed with PBS and lifted from their dishes using trypsin. After counting, 1 million cells were added to each sample of matrix. Cells were co-cultured with matrix samples in CCM for 3 days. On day 4 the media was changed to an osteogenic media as described elsewhere herein except for the absence of dexamethasone. After 17 total days of culture, dexamethasone was added to the media and the cells were grown for an additional 25 days for a total of 42 days. Samples of the media were obtained each day for analysis. Fluorescence intensity of the constructs was measured for each of the first 17 days to determine cell numbers and viability (FIG. 31). Media samples from days 4-9 were analyzed for OPG using an enzyme-linked immunosorbent-assay (ELISA). Microscopic photographs of the constructs were taken on day 10. Portions of some of the constructs were frozen on day 17 and were then sectioned. Samples were screened for GFP-positive cells and analyzed for alkaline phosphatase activity.

In order to characterize the influence of 7AIPM on osteogenic differentiation, hMSC's from two donors were cultured as described elsewhere herein with the addition of varying concentrations of the compound or vehicle to the media. Samples of the media were collected daily for analysis. These samples were analyzed for the presence of OPG and Dkk-1 using ELISA. Alkaline phosphatase activity of the monolayers and cell numbers were measured using a spectrophotometer.

The results of these experiments are now described. The data suggests that hMSCs were successfully co-cultured with the extracted matrices. This is evidence by the stabilization of fluorescence intensity. Furthermore, results indicate that these cells were induced to become osteogenic. Indications of this include the increase in OPG concentration detected by ELISA as well as by the presence of ALP detected in the sections of the constructs. Based on the appearance of physical properties of the matrix it appears that 3 weeks of culture is optimal for producing useful samples. Finally, 7AIPM was found to have increased osteogenic characteristics as shown by the increased ALP activity and OPG concentration as well as the decrease of Dkk-1 concentration (FIG. 34).

In the claims, the word "comprising" does not exclude other elements or steps, and the indefinite article "a" or an does not exclude a plurality. The mere fact that certain measures are recited in mutually different dependent claims does not indicate that a combination of these measured cannot be used to advantage.

The foregoing description is of examples embodying, at least in part, certain teachings of the invention. The invention, as defined by the appended claims, is not limited to the described embodiments. Alterations and modifications to the disclosed embodiments may be made without departing from the invention. The meaning of the terms used in this specification are, unless expressly stated otherwise, intended to have ordinary and customary meaning and are not intended to be limited to the details of the illustrated structures or the disclosed embodiments. Although the foregoing description of embodiments have shown, described and pointed out certain novel features of the invention, it will be understood that various omissions, substitutions, and changes in the form of the detail as illustrated as well as the uses thereof, may be made by those skilled in the art, without departing from the scope of the invention. Particularly, it will be appreciated that the one or more embodiments may manifest itself in other configurations as appropriate for the end use of the material made thereby.

What is claimed includes:

1. A composition for repair or reconstruction of bone tissue, wherein the composition is produced by:
    A) culturing mesenchymal stem cells for 5 to 14 days in a culture medium lacking dexamethasone, the culture medium comprising an effective amount of a peroxisome proliferator-activated receptor gamma (PPAR-γ) inhibitor, the culturing so as:
        (i) to inhibit regulation of adipogenesis in the mesenchymal stem cells;
        (ii) to induce the mesenchymal stem cells to exhibit: (a) early or primitive osteogenic differentiation without terminal differentiation; (b) an upregulation in gene expression for collagen types I, III, V, VI, XI, and XII, and (c) downregulation or depletion of cytosolic glycogen synthase kinase 3β; and
        (iii) to not induce mineralization;
    B) seeding the mesenchymal stem cells onto a three-dimensional scaffold, wherein the three-dimensional scaffold is produced from living cells; and
    C) allowing the cultured mesenchymal stem cells to produce and secrete an extracellular matrix mixture comprising insoluble components onto the three-dimensional scaffold, the insoluble components including collagen types I, III, V, VI, XI, and XII.

2. The composition of claim 1, wherein producing the composition further comprises a step D) comprising decellularizing the composition to remove the cultured mesenchymal stem cells.

3. The composition of claim 2, wherein step D) comprises decellularizing with one or more detergents and one or more enzyme treatments.

4. The composition of claim 1, wherein the extracellular matrix mixture further comprises collagen type XXI.

5. The composition of claim 1, wherein the culturing according to step A) is for 10 days or less.

6. The composition of claim 1, wherein the culture medium further comprises ascorbic acid and beta-glycerol phosphate.

7. The composition of claim 1, wherein the composition is cryopreserved.

8. The composition of claim 2, wherein producing the composition further comprises a step E) whereby the composition is subsequently seeded with additional mesenchymal stem cells.

9. The composition of claim 8, wherein the additional mesenchymal stem cells are pre-treated for differentiation into osteogenic cells.

10. The composition of claim 8, wherein the additional mesenchymal stem cells are pretreated with a PPAR-γ inhibitor.

11. The composition of claim 10, wherein the PPAR-γ inhibitor is 2-chloro-5-nitro-N-phenyl-benzamide.

12. The composition of claim 1, wherein the mesenchymal stem cells exhibit increased alkaline phosphatase activity after culturing according to step A).

13. The composition of claim 1, wherein step A) and step B) are performed together.

14. The composition of claim 1, wherein the mesenchymal stem cells produce extracellular matrix nodules after culturing according to step A).

15. The composition of claim 1, wherein the composition includes the three-dimensional scaffold, and the extracellular matrix mixture produced and secreted onto the three-dimensional scaffold.

16. The composition of claim 1, wherein the composition includes the three-dimensional scaffold, the cultured mesenchymal stem cells, and the extracellular matrix mixture produced and secreted onto the three-dimensional scaffold.

* * * * *